(12) United States Patent
Collier et al.

(10) Patent No.: US 8,883,487 B2
(45) Date of Patent: Nov. 11, 2014

(54) MOLECULAR DIAGNOSTICS SYSTEM AND METHODS

(75) Inventors: Gordon Bruce Collier, Fitzroy Harbour (CA); John Allister Wood, Sittsville (CA); Jason Andrew MacLeod, Ottawa (CA); William Charles Dicke, Aylmer (CA); Attila Csaba Nemeth, Ottawa (CA); Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 2260 days.

(21) Appl. No.: 12/308,307

(22) PCT Filed: Dec. 21, 2005

(86) PCT No.: PCT/US2005/046772
§ 371 (c)(1),
(2), (4) Date: May 14, 2010

(87) PCT Pub. No.: WO2006/071770
PCT Pub. Date: Jul. 6, 2006

(65) Prior Publication Data
US 2010/0291666 A1    Nov. 18, 2010

Related U.S. Application Data

(60) Provisional application No. 60/638,177, filed on Dec. 23, 2004.

(51) Int. Cl.
| C12M 1/34 | (2006.01) |
| C12M 3/00 | (2006.01) |
| B01L 3/00 | (2006.01) |
| C12Q 1/68 | (2006.01) |
| B01L 7/00 | (2006.01) |

(52) U.S. Cl.
CPC ......... B01L 3/502715 (2013.01); C12Q 1/6844 (2013.01); C12Q 1/686 (2013.01); B01L 3/502761 (2013.01); B01L 3/502769 (2013.01); B01L 7/52 (2013.01); B01L 2200/027 (2013.01); B01L 2200/0647 (2013.01); B01L 2200/10 (2013.01); B01L 2300/0816 (2013.01); B01L 2400/0421 (2013.01); B01L 2400/0487 (2013.01)
USPC ........................................ 435/287.2; 435/6.1

(58) Field of Classification Search
CPC ...... C12Q 1/686; C12Q 1/6844; C12Q 1/689; C12Q 1/6853; C12Q 1/6848; C12Q 1/6883; C12Q 1/6827; C12Q 1/6816; C12Q 2600/156; C12Q 1/6869; C12M 41/14; C12M 23/48; B01L 7/52; B01L 7/00; B01L 2300/0829; B01L 3/502715; B01L 3/502761; B01L 3/502769; B01L 2200/10; B01L 2200/027; B01L 2200/0647; B01L 2300/0816; B01L 2400/0421; B01L 2400/0487
USPC ............................................... 435/287.2, 6.1
See application file for complete search history.

(56) References Cited

U.S. PATENT DOCUMENTS

| 4,683,195 A | 7/1987 | Mullis et al. |
| 4,840,893 A | 6/1989 | Hill et al. |

(Continued)

FOREIGN PATENT DOCUMENTS

| JP | 2002-542461 U | 12/2002 |
| JP | 2004-301767 A | 10/2004 |

(Continued)

OTHER PUBLICATIONS

Bonnet et al., 1999, Proc. Natl. Acad. Sci. USA, vol. 96:6171-6176.

(Continued)

Primary Examiner — Michael Hobbs

(57) ABSTRACT

The present invention relates to automated devices and methods for the extraction of nucleic acids from cells, the amplification of segments of nucleic acid and the detection of nucleic acids, all in a convenient and portable manner. The invention is particularly suited for use in point-of-care medical diagnostic testing.

21 Claims, 40 Drawing Sheets

(56) References Cited

U.S. PATENT DOCUMENTS

| | | |
|---|---|---|
| 4,876,187 A | 10/1989 | Duck et al. |
| 5,063,081 A | 11/1991 | Cozzette et al. |
| 5,096,669 A | 3/1992 | Lauks et al. |
| 5,200,051 A | 4/1993 | Cozzette et al. |
| 5,279,936 A | 1/1994 | Vorpahl |
| 5,333,675 A | 8/1994 | Mullis et al. |
| 5,447,440 A | 9/1995 | Davis et al. |
| 5,466,575 A | 11/1995 | Cozzette et al. |
| 5,525,494 A | 6/1996 | Newton |
| 5,527,670 A | 6/1996 | Stanley |
| 5,554,339 A | 9/1996 | Cozzette et al. |
| 5,573,906 A | 11/1996 | Bannwarth et al. |
| 5,607,832 A | 3/1997 | Stanley et al. |
| 5,609,824 A | 3/1997 | Lauks et al. |
| 5,639,423 A | 6/1997 | Northrup et al. |
| 5,645,801 A | 7/1997 | Bouma et al. |
| 5,656,430 A | 8/1997 | Chirikjian et al. |
| 5,656,493 A | 8/1997 | Mullis et al. |
| 5,660,988 A | 8/1997 | Duck et al. |
| 5,763,178 A | 6/1998 | Chirikjian et al. |
| 5,807,527 A | 9/1998 | Burgoyne |
| 5,814,450 A | 9/1998 | Stanley et al. |
| 5,824,477 A | 10/1998 | Stanley |
| 5,837,454 A | 11/1998 | Cozzette et al. |
| 5,837,466 A | 11/1998 | Lane et al. |
| 5,854,033 A | 12/1998 | Lizardi |
| 5,939,312 A | 8/1999 | Baier et al. |
| 5,945,286 A | 8/1999 | Krihak et al. |
| 5,952,172 A | 9/1999 | Meade et al. |
| 5,976,336 A | 11/1999 | Dubrow et al. |
| 6,054,277 A | 4/2000 | Furcht et al. |
| 6,117,398 A | 9/2000 | Bienhaus et al. |
| 6,168,922 B1 | 1/2001 | Harvey et al. |
| 6,168,948 B1 | 1/2001 | Anderson et al. |
| 6,197,508 B1 | 3/2001 | Stanley |
| 6,277,576 B1 | 8/2001 | Meade et al. |
| 6,303,288 B1 | 10/2001 | Furcht et al. |
| 6,326,145 B1 | 12/2001 | Whitcombe et al. |
| 6,346,387 B1 | 2/2002 | Stewart et al. |
| 6,372,484 B1 | 4/2002 | Ronchi et al. |
| 6,379,929 B1 | 4/2002 | Burns et al. |
| 6,391,558 B1 | 5/2002 | Henkens et al. |
| 6,436,355 B1 | 8/2002 | Lee et al. |
| 6,440,725 B1 | 8/2002 | Pourahmadi et al. |
| RE37,891 E | 10/2002 | Collins et al. |
| 6,485,915 B1 | 11/2002 | Keller et al. |
| 6,589,742 B2 | 7/2003 | Edman et al. |
| 6,750,053 B1 | 6/2004 | Widrig Opalsky et al. |
| 2003/0170881 A1 | 9/2003 | Graham et al. |
| 2003/0190608 A1* | 10/2003 | Blackburn ............ 435/6 |
| 2004/0058378 A1 | 3/2004 | Huimin et al. |
| 2004/0086870 A1* | 5/2004 | Tyvoll et al. ............ 435/6 |
| 2004/0223874 A1 | 11/2004 | Numajiri |
| 2005/0084424 A1* | 4/2005 | Ganesan et al. ........ 422/100 |
| 2005/0211559 A1 | 9/2005 | Kayyem |
| 2009/0246782 A1 | 10/2009 | Kelso et al. |

FOREIGN PATENT DOCUMENTS

| | | |
|---|---|---|
| WO | WO 96/09308 A1 | 3/1996 |
| WO | WO 97/02357 A1 | 1/1997 |
| WO | WO 0062931 A1 | 10/2000 |
| WO | WO 01/94572 A1 | 12/2001 |

OTHER PUBLICATIONS

Chartier-Harlin et al., 2004, Lancet, vol. 364(9440):1167.
Kaboev et al., 2000, Nucleic Acids Research, vol. 28(21):e94.
Rooney et al., 2004, J. Pathol. vol. 204(3):282.
Rychlik et al., 1989, Nucleic Acids Research, vol. 17(21):8543-8551.
Rychlik, 1995, Molecular Biotechnology, vol. 3(2): 129-134.
Sambrook and Russell, 2001, "Molecular Cloning: A Laboratory Manual", Ch. 5.
Takagi et al., 1997, Applied and Environmental Microbiology, vol. 63(11):4504.
Tsourkas et al., 2003, Nucleic Acids Research, vol. 31(4):1319-1330.
Vincent et al., 2004, EMBO Reports, vol. 5(8): 795-800.
Yamashita et al., 2004 European Neurology vol. 52(2):101.
Zhang et al., 2003, Laboratory Investigation, vol. 83(8):1147.
Canadian Office Action mailed Jul. 5, 2010 in corresponding Canadian Application No. 2,592,204.
Canadian Office Action mailed on Aug. 5, 2011 in corresponding Canadian Application No. 2,592,204.
International Preliminary Report and Written Opinion on Patentability mailed Jun. 26, 2007 in corresponding International Application No. PCT/US2005/046772.
European Search Report mailed on Feb. 24, 2012 in corresponding European Application No. 11171939.9-2403.
English language translation of Japanese Office Action for JP 2007-548516 dated Jun. 21, 2011.
Office Action for European Appl. No. 05 855 351.2 dated Jul. 8, 2014.
Tsang, et al., "Development of multiplex DNA electronic microarrays using a universal adaptor system for detection of single nucleotide polymorphisms", Drug Discovery and Genomic Technologies Introduction, 682 BioTechniques, Apr. 30, 2004.
Liu, et al., "Self-Contained, Fully Integrated Biochip for Sample Preparation, Polymerase Chain Reaction Amplificatio, and DNA Microarray detection", Anal. Chem. 2004, vol. 76, pp. 1824-1831.

* cited by examiner

| Enzyme | Substrate |
|---|---|
| beta-D-Galactopyranoside (beta-Galactosidase, E.C. 3.2.1.23) | 5-Bromo-4-chloro-3-indoyl |
| | 5-Bromo-6-chloro-3-indoyl |
| Beta-D-Glucuronide (beta-Glucronidase, GUS; E.C. 3.2.1.31) | 5-Bromo-4-chloro-3-indoyl |
| Alkaline Phosphatese | 5-Bromo-4-chloro-3-indoyl phosphate |
| | Nitroblue tetrazolium chloride |
| Horse Radish Peroxidase | 3',3',5,5' -tetramethylbenzidine |
| | 2,2'-azinobis[3-ethylbenzothiazoline-6-sulfonic acid]-diammonium salt |
| | o-phenylenediamine dihydrochloride |

FIG.22

Table of possible signal outcomes from the Hemochromatosis test

| Genotype/channel result | C282 | Y282 | H63 | D63 |
|---|---|---|---|---|
| C282/C282/H63/H63 | 2x | 0 | 2x | 0 |
| C282/Y282/H63/H63 | X | X | 2x | 0 |
| Y282/Y282/H63/H63 | 0 | 2x | 2x | 0 |
| C282/C282/H63/D63 | 2x | 0 | X | X |
| C282/C282/D63/D63 | 2x | 0 | 0 | 2x |
| C282/Y282/D63/D63 | X | X | 0 | 2x |
| Y282/Y282/H63/D63 | 0 | 2x | X | X |
| Y282/Y282/D63/D63 | 0 | 2x | 0 | 2x |
| C282/Y282/H63/D63 | X | X | X | X |

FIG.27

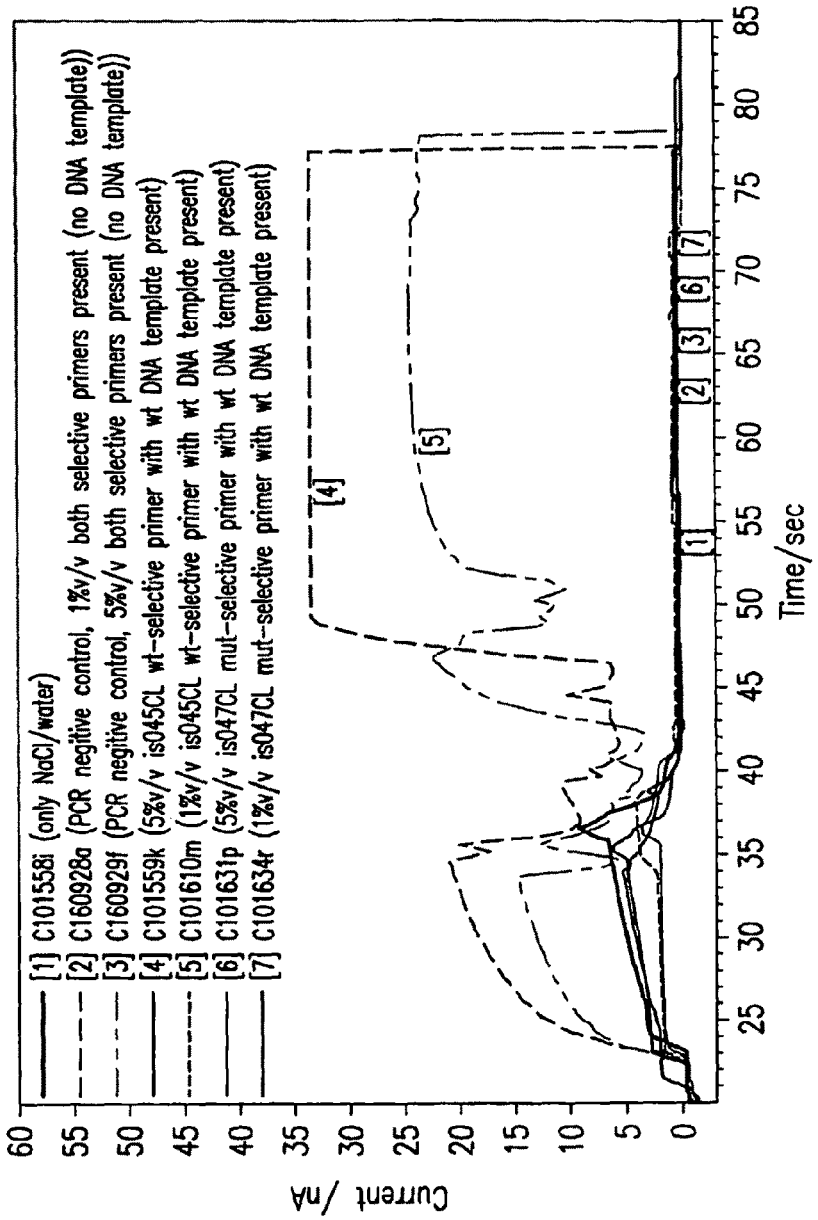

MOLECULAR DIAGNOSTICS SYSTEM AND METHODS

CROSS-REFERENCE TO RELATED APPLICATION

This application is a US national stage application of PCT/US2005/046772, filed on Dec. 21, 2005, which claims the benefit of U.S. provisional application No. 60/638,177 filed Dec. 23, 2004. Each of these applications is incorporated herein by reference in its entirety.

FIELD OF THE INVENTION

The present invention relates to an integrated nucleic acid test cartridge capable of performing extraction, amplification and detection together. It also relates to devices and methods for nucleic acid extraction alone, or extraction and amplification combined. Furthermore, it relates to devices and methods for amplification and detection combined. The cartridge may be equipped with a sensing means including enabling optical and electrochemical detection methods and it may also be equipped with a wax or absorbent filter extraction feature to separate target nucleic acid from the sample. The cartridge can perform various methods of amplification including polymerase chain reaction, rolling circle amplification and strand displacement amplification. The present invention also addresses novel amplification methods and reagents comprising single modified primers or pairs of modified primers, depending on the selected amplification method. Furthermore the present invention provides for integrated electrophoretic separation for primers from amplicons during a nucleic acid test.

BACKGROUND OF THE INVENTION

General Background on the Value of Nucleic Acid Testing

Applications of nucleic acid testing are broad. The majority of current commercial testing relates to infectious diseases including Chlamydia, gonorrhea, hepatitis and human immunodeficiency virus (HIV) viral load; genetic diseases including cystic fibrosis; coagulation and hematology factors including hemochromatosis; and cancer including genes for breast cancer. Other areas of interest include cardiovascular diseases and drug resistance screening, termed pharmacogenomics. The majority of testing currently occurs in centralized laboratories using non-portable and operationally complex instruments. Presently, tests generally require highly skilled individuals to perform the assays. As a result, the time taken between obtaining a sample suspected of containing a specific nucleic acid fragment and determining its presence or absence is often several hours and even days. However, as with other kinds of blood tests, physicians and others often require results more quickly and obtainable in a convenient user-friendly format. Consequently, there is a need for a portable analysis system capable of performing nucleic acid testing quickly and conveniently. A discussion of prior art relating to various aspects of nucleic acid testing is provided in the following sections.

Methods to Characterize Genetic Information

The clinical manifestation of a particular genetic characteristic can be different with different types or classes of genetic based diseases. This translates into different approaches to measure the genetic characteristic including SNP mutation detection, gene copy mutations and gene overexpression mutations. For example, some diseases such as hemochromatosis, cystic fibrosis or the oncogene p53, have one or a few very specific mutations which affect only a specific nucleotide. Considering hemochromatosis, there are two specific mutations. The clinical manifestation of this disease is an accumulation of iron in various tissues, which can be fatal if untreated. The most prevalent mutation is the G to A transition at nucleotide 845 in the gene, also known as (C282Y). See OMIM: Online Mendelian Inheritance in Man database, which can be found at the U.S. National Center for Biologic Information internet site. The second most prevalent mutation in the same hemochromatosis gene is a C to G transversion in exon 2, known as H63D. These are known as single nucleotide polymorphisms (SNPs). As every individual has two copies of each gene, the possible combinations of these genes are two wild type (homozygous wildtype), two mutated genes (homozygous mutant) or one wild type and one mutated gene (heterozygous). In the case of hemochromatosis, individuals who are homozygous mutant exhibit the disease state, heterozygous individuals can be susceptible for some aspects of the disease as they accumulate higher levels of iron than do homozygous wildtype individuals. Also, for the purpose of determining if an individual is a carrier of the disease to their offspring, the ability to determine that an individual is heterozygous can be useful.

As a result, in testing for a genetic disease like hemochromatosis, it is useful to be able to have at least four analytical means or channels for detection. Here, one channel detects the presence of wildtype C282, a second channel detects the presence of the mutant Y282 gene, a third channel detects the presence of the wildtype H63 gene and the fourth channel detects the presence of the mutant D63 gene. FIG. 12 provides a table of possible outcomes from a hemochromatosis test of this type and shows that it is possible to differentiate between homozygous or heterozygous, and that homozygous channels generate roughly twice the level of expression and thus signal in the test. Note that it is also useful to have one or more additional channels to use as positive and negative controls.

Some genetic mutations include multiple copies of the gene being present in the genome, causing a disease state in a patient. As an example the oncogene ZNF217 mapped within 20q13.2 has been found in multiple copies in individuals with colon cancer (Rooney et al., 2004, J. Pathol. Vol 204 (3):282). Genetic triplication of the alpha-synuclein gene (SNCA) has been reported to cause hereditary early-onset Parkinsonism with dementia (Chartier-Harlin et al., 2004, Lancet, vol 364 (9440):1167). Yamashita et al., 2004, European Neurology, vol 52 (2):101, have found that there is an increase in adult-onset Type III spinal muscular atrophy related to increased gene copies of the survival motor neuron (SMN2) gene. These gene copy mutations can be detected by using one or more required genes, such as the housekeeping genes (e.g. actin or glyceraldehyde-3-phosphate dehydrogenase). Overexpression mutations typically generate increased levels of mRNA and these can be detected.

Methods and Apparatuses for Extraction of Nucleic Acid

Nucleic acids found in cells can be deoxyribonucleic acid or ribonucleic acid and can be genomic DNA, extrachromosomal DNA (e.g. plasmids and episomes), mitochondrial DNA, messenger RNA and transfer RNA. Nucleic acids can also be foreign to the host and contaminate a cell as an infectious agent, e.g. bacteria, viruses, fungi or single celled organisms and infecting multicellular organisms (parasites). Recently, detection and analysis of the presence of nucleic acids has become important for the identification of single nucleotide polymorphisms (SNPs), chromosomal rearrangements and the insertion of foreign genes. These include infectious viruses, e.g. HIV and other retroviruses, jumping genes, e.g. transposons, and the identification of nucleic acids from recombinantly engineered organisms containing foreign genes, e.g. Roundup Ready™ plants.

The analysis of nucleic acids has a wide array of uses. For example, the presence of a foreign agent can be used as a medical diagnostic tool. The identification of the genetic makeup of cancerous tissues can also be used as a medical diagnostic tool, confirming that a tissue is cancerous, and determining the aggressive nature of the cancerous tissue. Chromosomal rearrangements, SNPs and abnormal variations in gene expression can be used as a medical diagnostic for particular disease states. Further, genetic information can be used to ascertain the effectiveness of particular pharmaceutical drugs, known as the field of pharmacogenomics. Genetic variations between humans and between domestic animals can also be ascertained by DNA analysis. This is used in fields including forensics, paternity testing and animal husbandry.

Methods of extracting nucleic acids from cells are well known to those skilled in the art. A cell wall can be weakened by a variety of methods, permitting the nucleic acids to extrude from the cell and permitting its further purification and analysis. The specific method of nucleic acid extraction is dependent on the type of nucleic acid to be isolated, the type of cell, and the specific application used to analyze the nucleic acid. Many methods of isolating DNA are known to those skilled in the art, see for example the general reference Sambrook and Russell, 2001, "Molecular Cloning: A Laboratory Manual". For example, the prior art contains examples of chemically-impregnated and dehydrated solid-substrates for the extraction and isolation of DNA from bodily fluids that employ lytic salts and detergents and which contain additional reagents for long-term storage of DNA samples e.g. U.S. Pat. No. 5,807,527 detailing FTA paper and U.S. Pat. No. 6,168,922 detailing Isocard Paper. The prior art also contains examples of particle separation methods, e.g. U.S. RE37,891.

Methods of isolating RNA, particularly messenger RNA (mRNA) are well known to those skilled in the art. Typically, cell disruption is performed in the presence of strong protein denaturing solutions, which inactivate RNAses during the RNA isolation procedure. RNA is then isolated using differential ethanol precipitation with centrifugation. As is well known, RNA is extremely labile and is sensitive to alkaline conditions, as well as RNAses, which degrade RNA. RNAses are ubiquitous within the environment and it has been found that they are difficult to remove from solutions and containers used to isolate RNA.

Methods and Apparatuses for Amplification of Nucleic Acid

Polymerase Chain Reaction (PCR) is inhibited by a number of proteins and other contaminants that follow through during the standard methods of purification of genomic DNA from a number of types of tissue samples. It is known that additional steps of organic extraction with phenol, chloroform and ether or column chromatography or gradient CsCl ultracentrifugation can be performed to remove PCR inhibitors in genomic DNA samples from blood. However, these steps add time, complexity and cost. This complexity limits incorporation into a simple disposable cartridge useful for nucleic acid analysis. Therefore, the development of new simple methods to overcome inhibitors found in nucleic acid samples used for nucleic acid amplification processes is desirable.

Nucleic acid hybridization is used to detect discernible characteristics about target nucleic acid molecules. Techniques like the "Southern analysis" are well known to those skilled in the art. Target nucleic acids are electrophoretically separated then bound to a membrane. Labeled probe molecules are then permitted to hybridize to the nucleic acids bound to the membrane using techniques well known in the art. This method is limited, because the sensitivity of detection is dependent on the amount of target material and the specific activity of the probe. As the probe's specific activity may be fixed, to improve the sensitivity of these assays, methods of amplifying nucleic acids are employed. Two basic strategies are employed for nucleic acid amplification techniques; either the number of target copies is amplified, which in turn increases the sensitivity of detection, or the presence of the nucleic acid is used to increase a signal generated for detection. Examples of the first approach are polymerase chain reaction (PCR), rolling circle (see U.S. Pat. No. 5,854,033), and nucleic acid system based amplification (NASBA). Examples of the second include, cycling probe reaction, termed CPR (see U.S. Pat. No. 4,876,187 and U.S. Pat. No. 5,660,988) and SNPase assays, e.g. the Mismatch Identification DNA Analysis System (see U.S. Pat. No. 5,656,430 and U.S. Pat. No. 5,763,178).

The PCR reaction is well known to those skilled in the art and was originally described in U.S. Pat. No. 4,683,195. The process involves denaturing nucleic acid, a hybridization step and an extension step in repeated cycles and is performed by varying the temperature of the nucleic acid sample and reagents. This process of subjecting the samples to different temperatures can be effected by placing tubes into different temperature water baths, or by using peltier-based devices capable of generating heating or cooling, dependent on the direction of the electrical current as described in U.S. Pat. No. 5,333,675 and U.S. Pat. No. 5,656,493. Many commercial temperature cycling devices are available, sold for example by Perkin Elmer, Applied Biosystems and Eppendorf. As these devices are generally large and heavy they are not generally amenable to use in non-laboratory environments, e.g. at the point-of-care.

A microfabricated device for performing the polymerase chain reaction is described in U.S. Pat. No. 5,639,423 though it is silent on providing an integrated means for extracting nucleic acids. A device for performing the polymerase chain reaction is described in U.S. Pat. No. 5,645,801 which has an amplification chamber that can be mated in a sealable manner to a chamber for detection. U.S. Pat. No. 5,939,312 describes a miniaturized multi-chamber polymerase chain reaction device. U.S. Pat. No. 6,054,277 describes a silicon-based miniaturized genetic testing platform for amplification and detection. A polymer-based heating component for amplification reactions is described in U.S. Pat. No. 6,436,355. U.S. Pat. No. 6,303,288 describes an amplification and detection system with a rupturable pouch containing reagents for amplification. U.S. Pat. No. 6,372,484 describes an apparatus for performing the polymerase chain reaction and subsequent capillary electrophoretic separation and detection in an integrated device.

There are several nucleic acid amplification technologies that differ from the PCR reaction in that the reaction is run at a single temperature. These isothermal methods include the cycling probe reaction, strand displacement, Invader™, SNPase, rolling circle reaction and NASBA. U.S. Pat. No. 6,379,929 describes a device for performing an isothermal nucleic acid amplification reaction.

More recently, a strategy for performing the polymerase chain reaction isothermally has been described by Vincent et al., 2004, EMBO Reports, vol 5 (8), see also US Application 20040058378. A DNA helicase enzyme is used to overcome the limitations of heating a sample to perform PCR DNA amplification.

Enzymes Used for the Polymerase Chain Reaction (PCR)

The polymerase chain reaction (PCR) is based on the ability of a DNA polymerase enzyme to exhibit several core features, which include its ability to use a primer sequence with a 3'-hydroxyl group and a DNA template sequence and to extend a newly synthesized strand of DNA using the template strand, all well known to those skilled in the art. In addition, DNA polymerases used in the PCR reaction must be able to withstand high temperatures (e.g. 90 to 99° C.) used to denature double stranded DNA templates, as well as be inactive at lower temperatures (e.g. 40 to 60° C.) at which DNA primers hybridize to the DNA template. Further, to have optimal DNA synthesis at a temperature near to the hybridization temperature (e.g. 60 to 80° C.).

In addition to these core characteristics, DNA polymerases also exhibit proofreading capabilities, which are due to the 3'-5' exonuclease activity inherent in most DNA polymerases. For the purpose of single nucleotide polymorphism (SNP) detection based on differential primer extension using PCR (also called 3'-allele specific primer extension), it is a disadvantage to use an enzyme that exhibits a 3'-5' exonuclease activity, as the terminal 3' nucleotide can be excised from a standard nucleic acid primer, permitting synthesis of both alleles.

Zhang et al., (2003, Laboratory Investigation, vol 83(8): 1147) describe the use of a terminal phosphorothioate bond to overcome the limitations of DNA polymerases used for 3'-5' exonuclease activity. The phosphorothioate bond is not cleaved by 3'-5' exonucleases. This prevents DNA polymerases with 3'-5' exonuclease activities from removing the terminal mismatch and proceeding with DNA elongation, alleviating the lack of discrimination observed with normal DNA.

Another characteristic of DNA polymerases is their elongation rate. Takagi et al., (1997, Applied and Environmental Microbiology, vol 63 (11): 4504) teach that *Pyrococcus* sp. Strain KOD1 (now *Thermococcus kodakaraensis* KOD1), *Pyrococcus furiosus*, Deep Vent (New England Biolabs, Beverly, Mass.), and *Thermus aquaticus* have elongation rates of 106 to 138, 25, 23 and 61 bases/second, respectively. The processivity rates of these enzymes are also described, and behave similarly to the elongation rates. Clearly, *Thermococcus kodakaerensis* KOD1 has much higher elongation and processivity rates compared to the other well-known enzymes, which would make this enzyme beneficial in applications where sensitivity and speed are an issue. Further, *Thermococcus kodakaerensis* KOD1 possesses an exonuclease activity which would be detrimental for use in a 3'-allele specific primer extention assay used for SNP analysis.

Design of Synthetic Oligonucleotides

Regarding the design of synthetic oligonucleotides for use in amplification reactions, Rychlik et al., (1989, Nucleic Acids Research, vol 17 (21):8543-8551) and Rychlik (1995, Molecular Biotechnology, vol 3: 129-134), describe selection criteria and computer programs to design probes and primers, including primers for in vitro amplification of DNA. Both teach that primers should not generate secondary structure or exhibit self-hybridization.

PCR primers designed as molecular beacons (Bonnet et al., 1999, Proc. Natl. Acad. Sci. USA, vol 96: 6171-6176) have a short region at both the 5' and 3' ends which are complementary generating what is known as hairpin loop structures, to quench the fluorescent signal by placing the donor and quencher molecules in close physical proximity to each other. After polymerization and incorporation into a newly synthesized double stranded molecule, the donor and quencher molecules are physically distant to each other, permitting the generation of a fluorescent signal. The region of complementarity is short and typically has only about 5 nucleotides which are complementary, preferably generating a hairpin stem. Tsourkas et al., 2003, Nucleic Acids Research, vol 31 (4):1319-1330, teaches that molecular beacons with longer stem lengths have an improved ability to discriminate between targets over a broader range of temperatures. However, this is accompanied by a decrease in the rate of molecular beacon-target hybridization. Molecular beacons with longer probe lengths tend to have lower dissociation constants, increased kinetic rate constants and decreased specificity. Therefore, having longer stem loops will have an impact on reducing the efficiency of hybridization kinetics, which in turn will reduce the levels of PCR amplification. Therefore, PCR using a stem loop structure is generally undesirable in the art. Kaboev et al., (2000, Nucleic Acids Research, vol 28 (21):e94) teaches that designing a PCR primer with a stem loop structure by adding additional sequences to the 5'-end of the primer, which are complementary to the 3'-end. This reference also teaches that adding this secondary structure increases the specificity of the PCR reaction, though it does use a PCR primer that permits the generation of single stranded tails. Further, Kaboev does not teach that the generation of the secondary structure prevents the hybridization of the single stranded regions to a capture moiety.

Detection Methods

Conventional detection methods for the final step in a nucleic acid analysis are well known in the art and include sandwich-type capture methods based on radioactivity, colorimetry, fluorescence, fluorescence resonance energy transfer (FRET) and electrochemistry. For example, jointly owned U.S. Pat. No. 5,063,081 covers a sensor for nucleic acid detection. The sensor has a permselective layer over an electrode and a proteinaceous patterned layer with an immobilized capture oligonucleotide. The oligonucleotide can be a polynucleotide, DNA, RNA, active fragments or subunits or single strands thereof. Coupling means for immobilizing nucleic acids are described along with methods where an immobilized nucleic acid probe binds to a complimentary target sequence in a sample. Detection is preferably electrochemical and is based on a labeled probe that also binds to a different region of the target. Alternatively, an immobilized antibody to the hybrid formed by a probe and polynucleotide sequence can be used along with DNA binding proteins. The '081 patent incorporates by reference the jointly owned patent U.S. Pat. No. 5,096,669 which covers a single-use cartridge for performing assays in a sample using sensors. These sensors can be of the type described in '081.

Other divisional patents related to '081 include U.S. Pat. No. 5,200,051 which covers a method of making a plurality of sensors with a permselective membrane coated with a ligand receptor that can be a nucleic component. U.S. Pat. No. 5,554,339 covers microdispensing, where a nucleic acid component is incorporated into a film-forming latex or a proteinaceous photoformable matrix for dispensing. U.S. Pat. No. 5,466,575 covers methods for making sensors with the nucleic component incorporated into a film-forming latex or a proteinaceous photoformable matrix. U.S. Pat. No. 5,837,466 covers methods for assaying a ligand using the sensor components including nucleic components. For example, a quantitative oligonucleotide assay is described where the target binds to a receptor on the sensor and is also bound by a labeled probe. The label is capable of generating a signal that is detected by the sensor, e.g. an electrochemical sensor. U.S. Pat. No. 5,837,454 covers a method of making a plurality of sensors with a permselective membrane coated with a ligand receptor that can be a nucleic component. Finally, jointly owned U.S. Pat. No. 5,447,440 covers a coagulation affinity-based assay applicable to nucleotides, oligonucleotides or polynucleotides. These jointly owned patents are incorporated herein by reference.

It is noteworthy that jointly owned U.S. Pat. No. 5,609,824 discloses a thermostated chip for use within a disposable cartridge applicable to thermostating a sample, e.g. blood, to 37° C. Jointly owned U.S. Pat. No. 6,750,053 and pending US 20030170881 address functional fluidic elements of a disposable cartridge relevant to various tests including DNA analyses. These additional jointly owned patents and applications are incorporated herein by reference.

Several other patents address electrochemical detection of nucleic acids, for example U.S. Pat. No. 4,840,893 discloses detection with an enzyme label that uses a mediator, e.g. ferrocene. U.S. Pat. No. 6,391,558 discloses single stranded DNA on the electrode that binds to a target, where a reporter group is detected by the electrode towards the end of a voltage pulse and uses gold particles on the electrode and biotin immobilization. U.S. Pat. No. 6,346,387 discloses another mediator approach, but with a membrane layer over the electrode through which a transition metal mediator can pass. U.S. Pat. No. 5,945,286 is based on electrochemistry with intercalating molecules. U.S. Pat. No. 6,197,508 discloses annealing single strands of nucleic acid to form double strands using a negative voltage followed by a positive voltage. Similar patents include U.S. Pat. No. 5,814,450, U.S. Pat. No. 5,824,477, U.S. Pat. No. 5,607,832 and U.S. Pat. No. 5,527,670 which disclose electrochemical denaturation of double stranded DNA. U.S. Pat. No. 5,952,172 and U.S. Pat. No. 6,277,576 disclose DNA directly labeled with a redox group.

Several patents address devising cartridge-based features or devices for performing nucleic acid analyses, these include for example a denaturing device U.S. Pat. No. 6,485,915, an integrated fluid manipulation cartridge U.S. Pat. No. 6,440,725, a microfluidic system U.S. Pat. No. 5,976,336 and a microchip for separation and amplification U.S. Pat. No. 6,589,742.

Based on the forgoing description there is a need for a convenient and portable analysis system capable of performing nucleic acid testing.

OBJECTS OF THE INVENTION

An object of the invention is to provide an integrated nucleic acid test cartridge capable of performing extraction, amplification and detection.

A further object of the invention is to provide an integrated nucleic acid test cartridge with optical and electrochemical detection.

A further object of the invention is to provide an integrated nucleic acid test cartridge with an extraction step based on filter extraction or on particle transit through a layer that is immiscible with an aqueous fluid.

A further object of the invention is to provide an integrated nucleic acid test cartridge capable of performing extraction and amplification.

A further object of the invention is to provide an integrated nucleic acid test cartridge capable of performing amplification and detection.

An object of the invention is to provide an integrated cartridge for nucleic acid testing that operates in conjunction with a reader instrument.

An object of the invention is to provide an integrated nucleic acid testing system and method suitable for analyses performed at the bedside, in the physician's office and other locations remote from a laboratory environment where testing is traditionally performed.

An object of the invention is to provide a device and method of nucleic acid extraction from a sample with a purification step involving particle transit through a layer that is immiscible with an aqueous fluid.

An object of the invention is to provide a device and method of filter-based nucleic acid extraction from a sample with an elution step prior to amplification.

An object of the invention is to provide a simple method and component for separating nucleic acid from a sample suitable for integration into a device for performing genetic analyses.

An object of the invention is to provide electrophoretic separation of primers from amplicons after amplification capable of integration with a nucleic acid testing cartridge.

An object of the invention is to provide a DNA polymerase enzyme that generates the most synthesis in the shortest time period, therefore a DNA polymerase with an elongation rate of over 100 bases per second or a processivity rate of over 300 bases.

It is another object of the invention to provide a DNA polymerase enzyme that functions in a miniaturized thermocycler device in a short time period.

SUMMARY OF THE INVENTION

The invention comprises an integrated single-use device for performing a nucleic acid analysis, comprising: (a) a housing; (b) an entry port for accepting a sample suspected of containing a target nucleic acid; (c) a first chamber operably connected to the entry port containing a reagent for extracting the target nucleic acid; (d) a first conduit permitting passage of extracted nucleic acid into an amplification chamber comprising a heating means and a temperature sensing means for controlling amplification conditions; (e) a second conduit operably linked to the amplification chamber and containing a sensing region with an immobilized capture oligonucleotide, wherein said housing comprises (i) an amplification reagent that is capable of incorporating a detectable label into an amplified nucleic acid target, and (ii) a means for moving the amplified nucleic acid target to the sensing region to permit binding of said amplified target to said capture oligonucleotide, and wherein said second conduit is operably attached to a holding chamber containing a fluid able to substantially displace uncaptured amplified target from the sensing region and permitting sensing of said detectable label retained in said sensing region.

In a preferred embodiment, the invention comprises an integrated single-use device for performing a nucleic acid analysis, comprising: (a) a housing; (b) an entry port for accepting a sample suspected of containing a target nucleic acid; (c) a first chamber operably connected to the entry port containing a reagent for extracting the target nucleic acid onto magnetic beads that are located in the first chamber, said first chamber also containing a wax or oil-filtering material for forming a substantially contiguous wax or oil-filtering layer in the region of the first chamber and a first conduit, wherein magnetic beads that are associated with extracted target nucleic acid may pass through the wax layer into the first conduit by means of an applied magnetic field; the first conduit permitting passage of target nucleic acid and beads into an amplification chamber, said housing containing an amplification reagent that is capable of incorporating a detectable label into an amplified nucleic acid target; the amplification chamber having a heating means and a temperature sensing means for controlling amplification conditions, (d) a second conduit operably linked to the amplification chamber and containing a sensing region with an immobilized capture oligonucleotide, wherein (i) said housing comprises a means for moving the amplified target to the sensing region to permit binding of said amplified target to said capture oligonucleotide, and (ii) said second conduit is operably attached to a holding chamber containing a fluid able to substantially displace uncaptured amplified target from the sensing region and permitting optical sensing of the detectable label retained in the sensing region.

The present invention demonstrates novel extraction procedure for removing known inhibitors of the PCR reaction from genomic DNA when using blood as the preferred tissue source. This procedure is of sufficient simplicity to enable integration into a device for performing genetic analyses outside of the typical laboratory environment. While this novel procedure can use components from commercially available kits, novel protocols are disclosed which significantly simplify and reduce the duration of the extraction process. The novel protocol can be readily adapted for the initial processing of whole blood for a rapid point-of-care nucleic acid diagnostic test.

The present inventive devices and processes significantly improves upon the existing state-of-the art by marrying chemically-impregnated solid-substrate technologies to a filtering apparatus to conveniently minimize the time and resources for extracting an amplifiable quantity of genomic DNA from low volumes of bodily fluids. As mentioned above, this technology is particularly amenable to use in a disposable cartridge device for DNA isolation, amplification and detection.

The present invention particularly addresses expanding opportunities for point-of-care diagnostic testing, i.e. testing that is rapid, inexpensive and convenient using small volumes of accessible bodily fluids such as blood or buccal cells.

Devices and processes for reliable and reproducible extraction and isolation of an amplifiable genomic DNA sample from a bodily fluid, preferably blood or buccal swab, preferably in 10-40 μL volumes are disclosed based on magnetic particle separation and filter binding. These devices and methods may be used individually for extraction alone, or integrated into testing devices.

In a particular embodiment, the present invention demonstrates a novel extraction procedure for removing known inhibitors of the PCR reaction from genomic DNA when using blood as the preferred tissue source. This procedure is of sufficient simplicity to enable integration into a device for performing genetic analyses outside of the typical laboratory environment. While this novel procedure can use components from commercially available kits, novel protocols are disclosed which significantly simplify and reduce the duration of the extraction process. The novel protocol can be readily adapted for the initial processing of whole blood for a rapid point-of-care nucleic acid diagnostic test.

BRIEF DESCRIPTION OF THE DRAWINGS

FIG. 22 shows examples of optical detection chemistries.

FIG. 27 provides a table of possible signal outcomes from a hemochromatosis test.

FIG. 32(b) shows the related chronoamperometry plot.

DETAILED DESCRIPTION OF THE PREFERRED EMBODIMENTS

Figure 1:
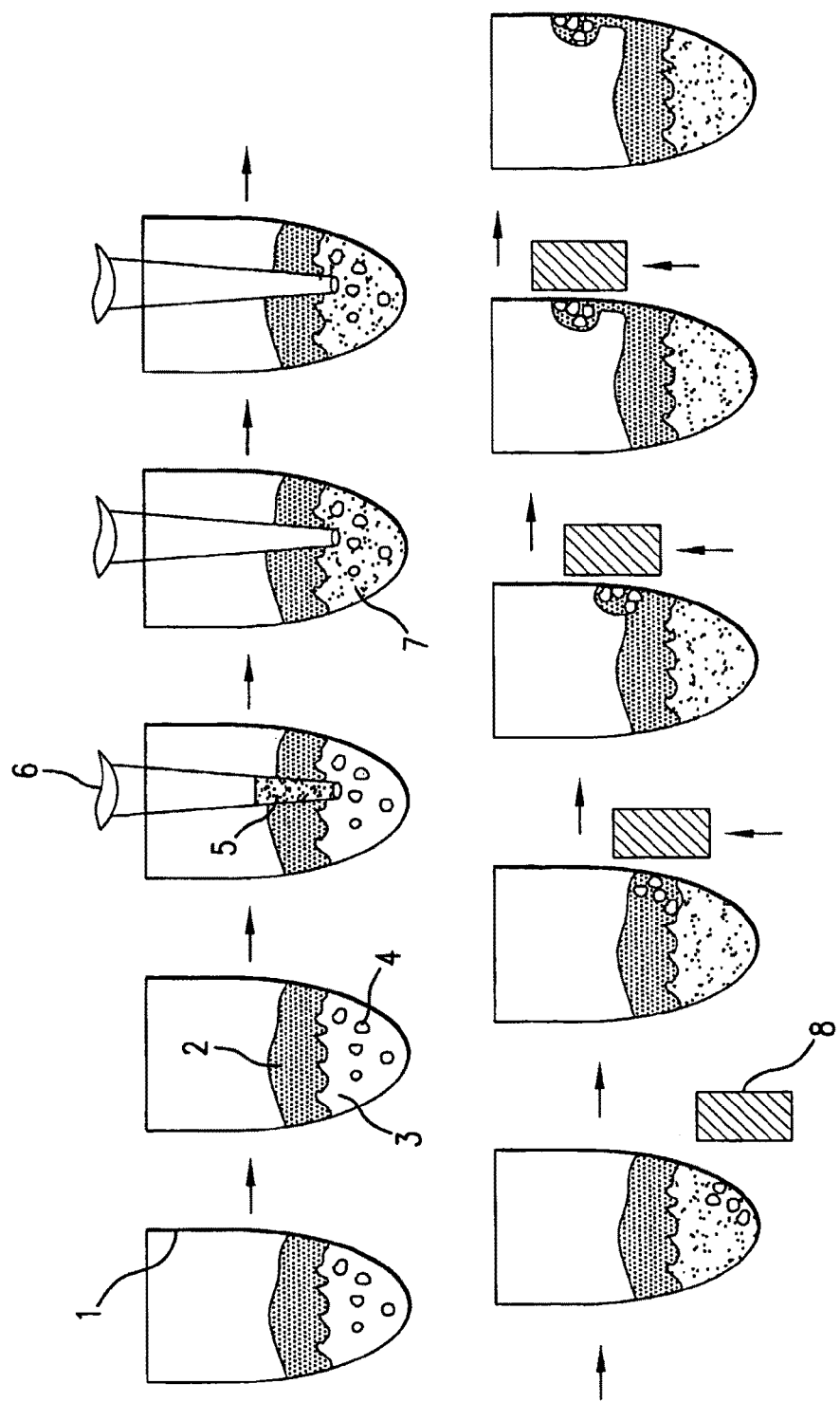
FIG. 1 shows nucleic acid purification in a tube using a lytic buffer layer, a wax layer and magnetic beads.

Nucleic Acid Separation Methods and Apparatuses Based on Magnetic Particles

The present disclosure demonstrates a rapid and simple protocol for isolating genomic DNA from whole blood for the primary purpose of performing an amplification reaction, e.g. polymerase chain reaction (PCR). The present method has the advantage of exhibiting a significant reduction in the common inhibitors of PCR, e.g. hemoglobin, found in prior art rapid DNA extraction protocols. In blood samples, added anticoagulation reagents such as chelating agents, heparin, EDTA and citrate can also act as inhibitors. The present method eliminates these inhibitors and other naturally occurring chelating agents as well as enzymes and proteins that can damage nucleic acid templates. It is important to note that this technique is also applicable to other sources of nucleic acid material, e.g. buccal swabs, urine, and other tissue samples, and can also be used in conjunction with other amplification methods.

By contrast with the prior art, for example that found in *Dynabeads Genomic DNA Blood* kit (Prod. No. 634.02, Dynal Biotech Corp.), and also US patent 2003/0180754A1 where nucleic acid extraction takes 30-40 minutes, the present method reduces the time required for reproducible DNA extraction to less than about 5 minutes and preferably and typically to about 2 minutes. This is a significant improvement when considering genetic analyses where the speed with which a result is obtained is crucial, e.g. the identification of highly infectious agents. It is also applicable to testing in the physician's office environment, or even at the bedside, where it is desirable to obtain a sample from a patient and deliver a result during a single physician visit.

The present method preferably uses coated beads, with an inner-core that is a paramagnetic material and a lysing and binding buffer. When a lysed cell solution containing genomic DNA is mixed with beads of the preferred embodiment, the surface chemistry on the beads weakly binds DNA with low specificity due to a strong negative surface charge, thus creating a bead-DNA complex. The preferred surface coating is a carboxylic acid coated surface and the paramagnetic beads typically have a 2.8 um diameter, though beads in the diameter range of about 0.1 to 100 um can be employed. Alternative anionic coatings for the beads include the following materials including very small diameter glass beads (e.g. Glass Milk), Whatman phosphocellulose and DEAE resin (e.g. DE52).

While non-magnetic beads may be used, it is certainly advantageous to use magnetic beads as these beads may be drawn to the side of a reaction vessel and held against the side by means of a magnet. This can occur within a short period of time, provides a means for concentrating the bead in one location and provides a means for moving and manipulating the beads. The magnetic field may be provided by a permanent magnet or by electromagnetic means, as is well known in the art.

In an example that uses a standard polypropylene PCR tube, a standard lytic buffer (Dynal Biotech Corp.) containing; water 60-100% wt, sodium chloride (NaCl) 10-30%, lithium chloride (LiCl) 5-10%, tris-HCl 1-5%, lithium dodecylsulfate (LiDS) 0.1-1%, EDTA 0-1%, and dithiothreitol (DTT) 0-0.1%; was modified to include NaOH reagent at a final alkaline concentration of 0.65M. Other lytic buffers known in the art may also be used with the appropriate addition of base, e.g. NaOH. Whole blood (10 uL) was then added directly to the alkaline-modified lytic buffer with Dynabeads (23 uL). This induced the lysis of blood cells in about 15 seconds of manual pipette mixing, followed by about 15 seconds of dwell time for the adsorption of genomic DNA onto the beads. The bead-DNA complex was then captured against the side of a tube with a permanent magnet, which takes less than about 15 seconds. The entire supernatant of lysed cells was then removed by pipette. A wash buffer (50 uL), e.g. Dynal wash buffer (from a Dynal kit) was introduced by pipette and used to rinse the bead-DNA pellet that was captured against the tube wall. The wash solution was then entirely removed by pipette while the pellet remained captured against the tube wall. The remaining bead-DNA pellet (1-2 uL equiv. volume) was then removed and added to a new tube with a PCR cocktail (~25 uL) comprising polymerase enzyme, primers, dNTPs and buffer along with a mineral oil overlay (~10 uL) and placed into a conventional thermocycler. The total duration of this extraction process was found to be about two minutes. Note that it is demonstrated below that this novel purification protocol overcomes the problem associated with inhibitors of a PCR reaction remaining in the extract.

In a preferred embodiment, the extraction method employs alkaline lytic buffer, magnetic beads and also a wax or oil-filtering medium. Again, the method can be performed as a manual procedure, as described here, or as the basis of an automated analysis in a disposable device. The use of wax or oil as a filtering medium overlaying the lysed-cell bead-DNA complex mixture eliminated the need for further fluid movement and assisted in purifying the bead-DNA complex. For instance, blood was combined with the lytic buffer and beads and the resulting DNA-bead complex was pelleted and drawn through an upper filtering layer with a permanent magnet, thus selectively separating the complex from the bulk of solution. This is illustrated in detail in FIG. 1.

FIG. 1 shows a tube 1 contains a wax filtering medium 2 above a lytic buffer 3 and magnetic beads 4. Typically the tube is stored at ambient temperature, so the tube is first heated to melt the wax. Generally, this is a temperature change to above about 35° C. Blood 5 is introduced with a pipette 6 and the blood is well mixed so that cells lyse in the buffer. Nucleic acid 7 then binds to the beads via non-specific surface bonds. A magnet 8 is then used to draw the beads and some extra lysed material and buffer to side of the tube to form a pellet. The magnet is then moved along side the tube to draw the pellet upwards through the wax layer. It has surprisingly been found that this effectively filters the pellet, as excess aqueous fluid is excluded by the greater surface tension of the wax. Optionally, after this step, the wax may be re-hardened by removing the heat. The resulting bead-nucleic acid pellet remains trapped in a thin layer of wax easily accessible at the side of the tube, while the lytic buffer and blood remains trapped below the wax. The bead-nucleic acid pellet can then be removed from the side of the tube and introduced to a new tube with the PCR cocktail present. The nucleic acid elutes off the bead during the first heating cycle of PCR, as it has been found that water at a temperature of above 80° C. is sufficient for elution. It has also been found that neither the beads nor the wax interfere with PCR.

Ideal characteristics of waxes for this application include waxes which melt from a solid to a liquid at between 25 to 45° C. Further, these preferred waxes do not significantly evaporate at temperatures in the range 60 to 90° C. When these waxes are solid they prevent movement of bead and other solutions that are trapped by their presence, however, when these waxes are in a liquid state their viscosity is sufficiently low to permit passage of magnetic beads under a magnetic field. The waxes also have the property of being compatible with reagents for DNA amplification. Four examples of waxes that can be used in the present invention are heneicosane (98%, m.p. 40-42° C., Sigma), docosane (99%, m.p. 43-45° C., Sigma), tricosane (99%, m.p. 48-50° C., Sigma) and tricosaheneicosane. The preferred wax is heneicosane. Other organic liquids that can be used to form the barrier layer through which the beads pass include silicone oil and mesitylene.

Figure 2:
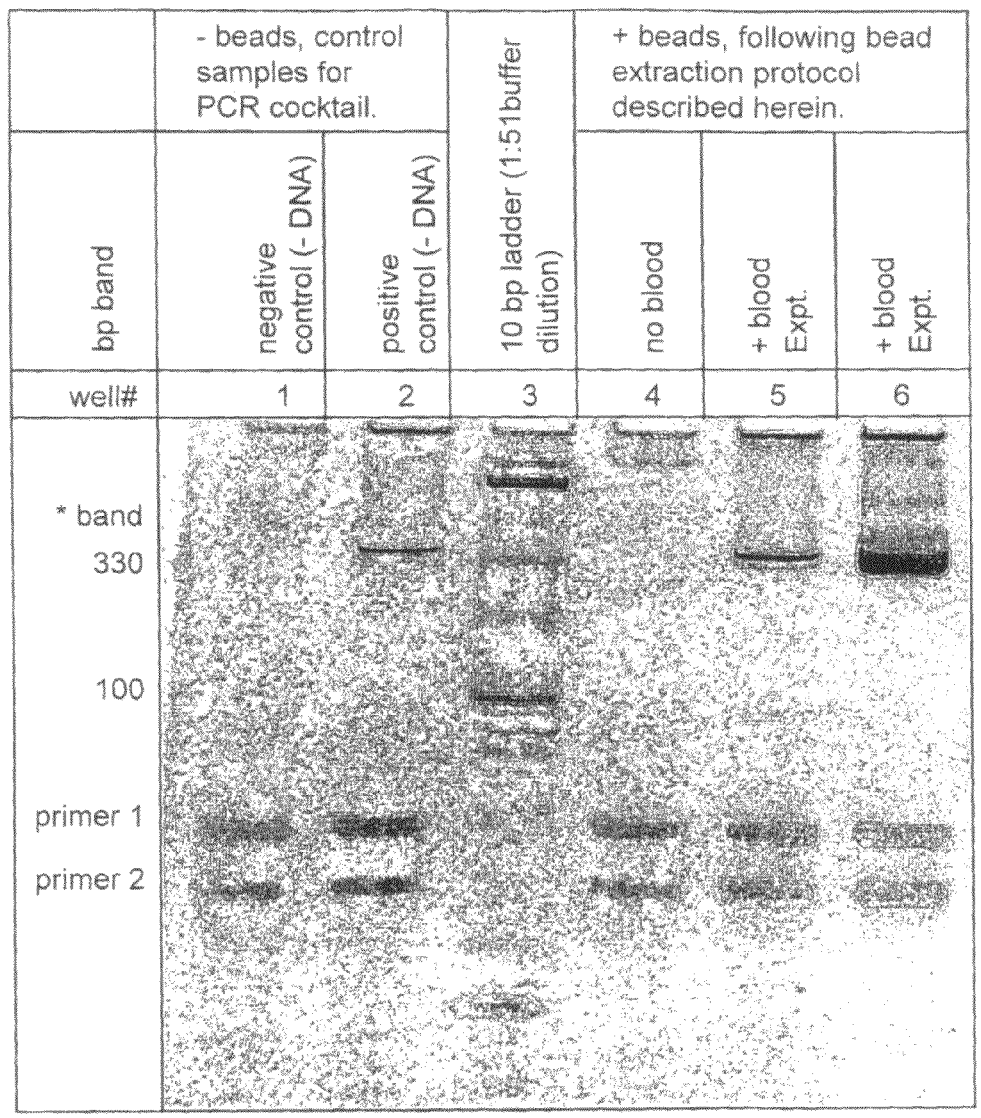
FIG. 2 shows a polyacrylamide gel of PCR products with and without beads and with and without blood, and also purified DNA controls.

FIG. 2 demonstrates the successful removal of a purified DNA sample from blood using the beads transiting through wax process, with the presence of the anticipated bands (gel lanes 5 and 6 matching lane 2). This figure shows a polyacrylamide gel of PCR products with and without beads and with and without blood and also purified DNA controls. Note that the band labeled "*" represents the anticipated base-pair length for symmetrical PCR with a modified wild-type Hemachromatosis oligonucleotide primer set prepared on a known wild-type alleles ACD blood tube sample. The positive control (lane 2) also represents genomic DNA purified using a Qiagen commercial kit for sample preparation (wild-type alleles) and the negative control (lane 1) features with no DNA added to the PCR cocktail. In this example, PCR was performed in a conventional thermocycler, with a mineral oil overlay, using 30 cycles. A volume of 10 uL of sample plus 2 uL of loading dye was added into each well of a 10% non-denaturing polyacrylamide gel, 1×TBE buffer, as shown in FIG. 2.

Figure 3:
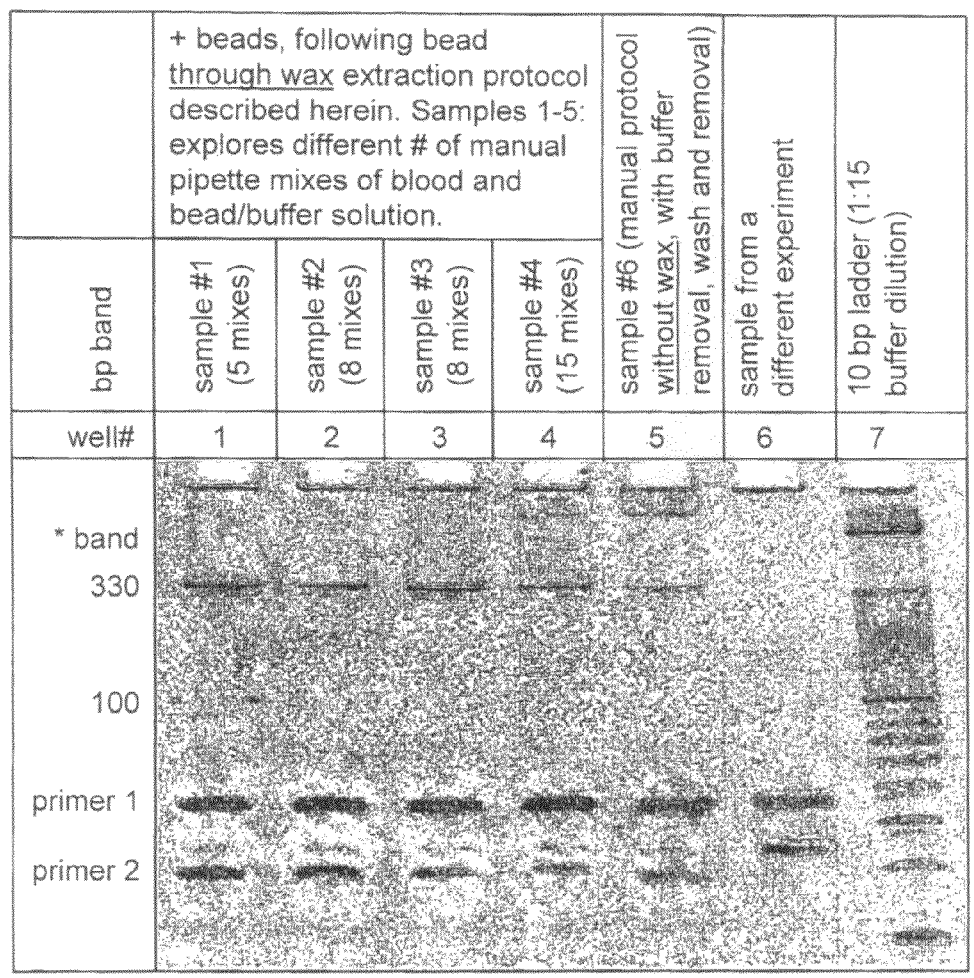
FIG. 3 shows a polyacrylamide gel of PCR products with beads and blood.

FIG. 3 contrasts the successful removal of purified DNA from blood using the beads transiting through wax protocol (gel lanes 1-4) to the protocol without using the wax as a filter medium (gel lane 5). The band labeled "*" represents the anticipated base-pair length for symmetrical PCR with a modified wild-type Hemachromatosis oligonucleotide primer set prepared on a known wild-type alleles ACD blood tube sample. PCR was performed in a conventional thermocycler, with mineral oil overlay, using 30 cycles. A volume of 10 uL of sample plus 2 uL of loading dye was added into each well of a 10% non-denaturing polyacrylamide gel, 1×TBE buffer, as shown in FIG. 3.

The principles demonstrated by the above description can be incorporated into an individual nucleic acid extraction device based on manual manipulations of the type shown in FIG. 1, or into an automatic device as described below, where the user only needs to add the sample to the device and all the other steps are performed automatically.

Nucleic Acid Separation Methods and Apparatuses Based on Absorbent Filters

An alternative approach to quickly extract and isolate nucleic acids found in bodily fluids is provided. It is based on the use of filter materials. The disclosed devices and processes significantly improve upon the existing art by marrying chemically impregnated solid-substrate technologies to a miniaturized filtering apparatus. It also conveniently minimizes the time for extraction of an amplifiable quantity of genomic DNA from a low volume of bodily fluid. While the device may be used as an individual separation device, it is particularly amenable to integration into a disposable cartridge device for DNA isolation, amplification and optionally detection.

The individual device can be used, for example, in clinical and research environments as a rapid means for taking a small volume of fluid, such as blood or buccal cells, and quickly isolating DNA amenable to amplification. Alternatively, when incorporated into a disposable cartridge, microfluidic elements are used to automatically move the sample within the cartridge and to affect the extraction process. Both applications are described.

The primary features of the device and method combine; (i) rapid nucleic acid isolation, typically in less than two minutes, (ii) elements amenable to incorporation in a disposable cartridge, (iii) generation of either bound or unbound nucleic acid in a form compatible with amplification, (iv) utilization of small sample volumes, e.g. blood, buccal cells and tissue, and (v) utilization of small volumes of other liquid reagents to perform the operation.

Regarding the device, the supporting structure of a low-volume filter holding apparatus was used for the placement of a chemically-impregnated solid-substrate matrix. It functions as a filtering layer that extracts and isolates DNA from an applied sample by retaining these nucleic acids within its matrix. The filtering matrix was impregnated with lytic salts and optionally detergent, which after the binding step is then flushed or washed with a solvent, preferably distilled or sterile deionized water, to remove common inhibitors of amplification and to rinse away denatured proteins. The filter retaining nucleic acids from the sample can then be removed from the supporting apparatus and directly applied to amplifying reagents, e.g. PCR. This can be done using the whole filter disc, or a portion thereof, depending upon the quantitative requirements for DNA. Where desirable the nucleic acid material may be eluted from the filter preferably using deionized water at a temperature in the range 75 to 95° C. Other eluting reagents include dilute neutral buffers, such as 10 mM Tris at pH 7 and 5 mM to 20 mM sodium or potassium phosphate buffers. Alternatively, a filtering matrix can be incorporated in a disposable nucleic acid testing cartridge, as described below.

The preferred embodiment of the individual extraction device is described as follows: The chemically-impregnated filter is a disc composed of a reproducible thin matrix that is biochemically inert, preferably a commercially available filtering paper. The lytic salts and optionally a detergent are dispensed onto the surface of the filter and then dried within the matrix. As a practical matter, the size of the filter-disc is restricted by the outer-diameter of the filter holder, and must be wider than the channel through which the wash fluid passes. Chemical impregnation is by means of a liquid cocktail containing a chaotropic salt, with or without detergent, a weak basic buffer, and a chelating agent. The cocktail is dispensed onto the filter-disc, dried and then the filter is stored in a sealed environment until use.

In the preferred embodiment, the filter holder device provides rigid support to the filter-disc (optionally with a placement-assisting gasket) with a central small-diameter channel through which the wash fluid may pass from one side of the filter-disc to the other. The device contains both an inlet and an outlet on opposite sides of the filter-disc to allow for the introduction and later removal of the wash fluid. Its construction material should be biochemically inert, preferably a molded plastic. It is designed to be disposable, but it optionally could be reusable if properly cleaned, e.g. autoclaved. The filter base-pad is a subcomponent that assists in the proper placement of the filter-disc in line with the wash fluid channel. Optionally a filter-positioning gasket may be employed for sizes of filter that are smaller than the internal diameter of the device. For example a thin adhesive layer with a central hole that holds the filter-disc onto the filter base-pad over the channel may be used. In this embodiment, a double-sided adhesive tape with a central hole slightly smaller than the outer-diameter of the filter-disc is preferred. Wash fluid is preferably distilled water and is used to remove chemical inhibitors of amplification.

As is well known in the art, conditions of sterility and biochemical inertness are intrinsic to the choice of materials employed for the construction of the device, the handling of fluids and the source of the wash fluid. Samples, e.g. bodily fluids, can be introduced to the filter-disc through the inlet of the filter holder, or onto the filter-disc before assembly into the device, provided care is taken to ensure sterility.

In one embodiment, the filter holder can be a Swinnex filter holder, preferably the 13 mm diameter version (Millipore Corp.), which is also provided with a Teflon™ gasket and is constructed of molded polypropylene. In a preferred embodiment, a modification was performed upon the filter holder where additional acrylic pieces are cut to exactly fit the void spaces inside both the top and bottom pieces of the filter holder. These pieces are preferably held in place with adhesive, e.g. Loctite epoxy glue, and have a drilled central channel of a smaller diameter than the standard device. The inlet to the filter holder can also optionally be modified with an end piece from an Eppendorf 100 µL pipette tip that is held into position with adhesive.

The filter positioning gasket is preferably a double-sided adhesive tape gasket (i-STAT Canada Ltd.), laser cut to a thickness of about 25 um on a PET film base with about 75 um of a rubber-acrylic hybrid adhesive, sandwiched between two polyester liners for protection. A two-sided adhesive has the advantage of providing a better seal of the filter holder during the washing procedure. Note that the polyester liners are removed during assembly of the device to expose the adhesive.

The filter disc is preferably Whatman 4 Qualitative Grade plain cellulose paper, (Whatman Inc.), with the following manufacturer's specifications; particle retention greater than 20-25 µm, coarse porosity, filtration speed ASTM 12 sec., Herzberg 37 sec., and a smooth surface. Other similar filter materials and grades may be used include Whatman 3MM, Pall GF A/B, Texwipe (cleaning cloth), Whatman 1, Whatman 3, Whatman 4, Whatman 6 and Pall 1660 membranes.

Chemical impregnation of the filter is preferably with a liquid cocktail that contains chaotropic salts, preferably a guanidinium salt such as guanidine isothiocyanate, with or without detergent preferably Triton-X100™, a weak basic buffer preferably TRIS, and a chelating agent preferably EDTA. Alternative reagents include guanidinium salts (e.g. guanidinium hydrochloride and guanidinium thiocyanate), non-ionic detergents and chelating materials. The cocktail is applied to Whatman 4 paper in solution for minimal loading of approximately 3.75 µL/cm$^2$ of 2M guanidine isothiocyanate, 1% Triton X100, 10 mM TRIS buffered to pH 8.8 and 2 mM EDTA. The cocktail is then dried under a heat lamp (Philips, Heat-Ray 250w infrared) about 5 cm below the light surface for 3 minutes, then cooled at room temperature for a minimum of 10 minutes and stored in a sterile centrifuge tube until use. Note that where the intended sample material is blood, it has been found that impregnation with a solution of 200 mM NaOH can be substituted for all the reagents used in the cocktail solution. Other strong basic solutions can also be used e.g. KOH.

By way of demonstration, two different bodily fluids have been used for the extraction of genomic DNA. These are (i) white blood cells within a whole blood sample, that are untreated by either chelating or anticoagulation agents, and (ii) buccal cells obtained from a cheek swab. When utilized as described below, the present device can extract amplifiable DNA from both fluids with a minor variation in the protocol. Based on this disclosure, those skilled in the art will recognize that other types of sample containing nucleic acid may also be extracted by making further minor variations in the protocol.

Figure 4A:
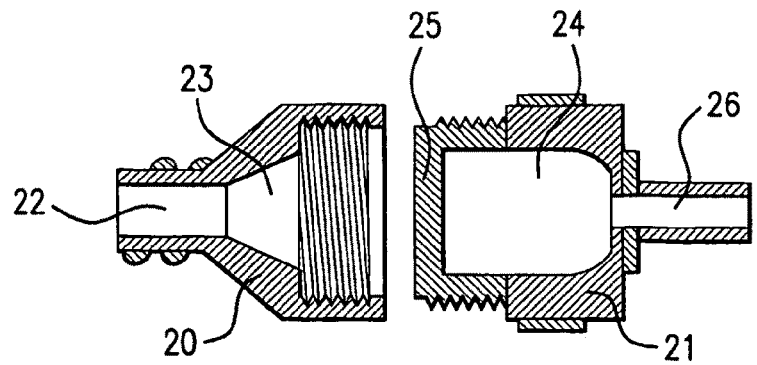
FIG. 4(a)-(d) show different perspectives of the filter holder.
Figure 4B:
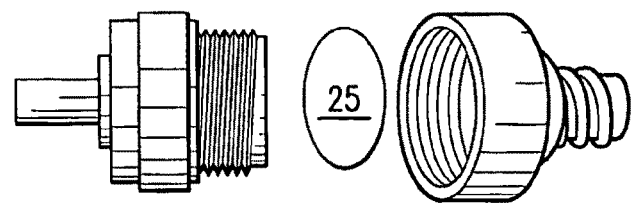
Figure 4C:
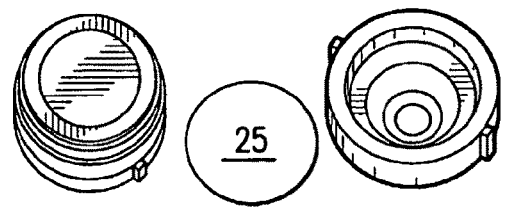
Figure 4D:
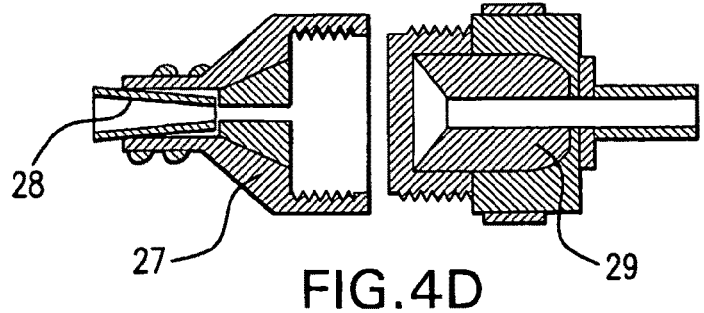

The component elements of filter holder are shown in FIG. 4(a) in side view, FIG. 4(b) exploded side view, FIG. 4(c) top view and FIG. 4(d) with a void volume insert. The device comprises a filter holder top 20 and bottom 21, an inlet channel 22, void spaces 23 and 24, a filter disc 25 on a filter disc base and an outlet channel 26. In the preferred embodiment, as shown in FIG. 4(d), a lower volume modification employs a void-filling structures (27, 29) and an inlet adaptation element 28 to facilitate better transfer of fluid into the narrower central channel via inlet 22. The lower volume device requires the filter-disc to be positioned with a filter gasket attached to adaptation element 29. As a practical matter, the device is prepared in a sterile working environment and tools to prevent cross-contamination of nucleic acids and enzymes are used.

When using a 13 mm filter-disc 25, about 3-10 µL of bodily fluid can be applied to the chemically-impregnated filter surface, whereas the lower-volume modified device, with a 4.8 mm filter disc functions well with 1-3 µL of fluid. Sample application can be achieved with the assembled device through the inlet port, or directly onto the filter prior to assembly. Where a buccal swab is acquired with a cotton swab, it can be wiped onto the filter disc or washed onto the filter disc through the inlet port. It has been found that another method for, isolating buccal cells is by using a commercial mouthwash, e.g. Scope brand. A few microliters of used mouthwash can then be applied into the device.

Regarding removal of interferents, it was found that sterile water at ambient temperature performs satisfactorily as a wash fluid as it is capable of flushing interferents through the filter-disc without removing nucleic acids from within the matrix of the disc. When water is pumped from a dispensing tip positioned for a tight seal at the inlet to the filter holder, it flushes through the filter-disc washing the sample and passing through to the outlet. For buccal cell samples, a single flush of 20 µL of sterile water per µL of sample is sufficient. For blood samples, 20 µL of sterile water per µL sample is preferably flushed through the filter and repeated three times. Alternatively a single volume passed forward and backwards thrice is sufficient. As an alternative to sterile water the following sterile buffer solutions may be used, 10 mM Tris at pH 7 and 5 mM to 20 mM sodium or potassium phosphate.

After the washing procedure the filter-disc retains an amplifiable quantity of DNA. It can then be removed from the filter holder and employed in an amplification reaction. It has been found that a 4.76 mm diameter disc can be employed in a 100 µL PCR amplification directly, whereas a 13 mm disc is optimally cut into smaller portions. In an alternative embodiment the nucleic acid material can be eluted from the filter by using hot deionized water or various buffer solutions and then introduced into an amplification device. In another embodiment the filter process is integrated into a disposable device for nucleic acid testing, as described below.

Figure 5:
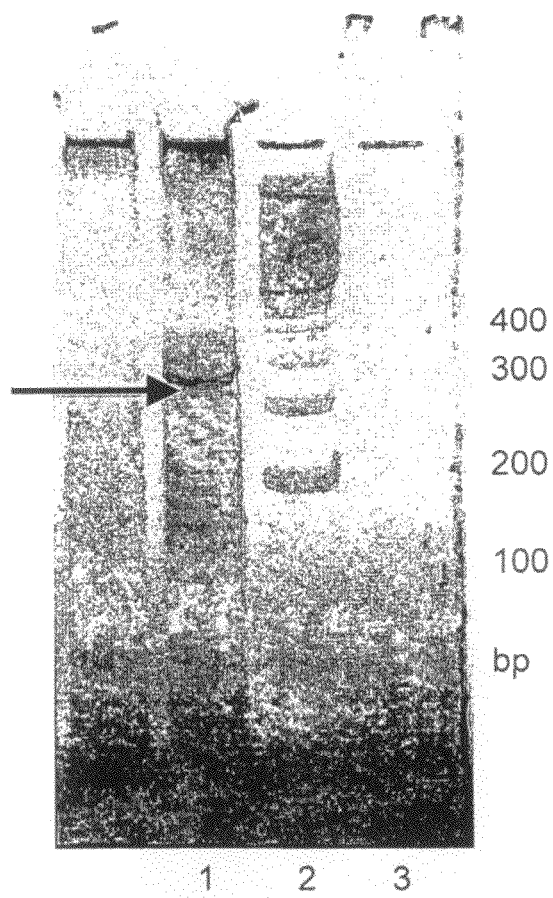
FIG. 5 shows PCR amplification of a buccal swab sample isolated from a filter.

FIG. 5 demonstrates the effectiveness of the method and filter holder device, showing PCR amplification of a buccal swab sample. After the extraction process, the filter was removed from the device and placed into a 100 uL PCR reaction chamber using two primers specific for the hemachromatosis gene (Hfe). Once the amplification process was completed, material was applied to lane 1 of a 10% acrylamide 1× TBE electrophoresis gel. As expected this generated a 390 bp (base pair) fragment indicated by the arrow. Note that control lane 2 contained a 100 bp ladder and lane 3 contained water as a negative control.

It is understood that the manual procedure described above can form the basis for the design of an extraction module included and integrated within a disposable device for performing genetic analyses, or be a separate module that delivers an extract to a disposable device. Delivery can be for example by pipette transfer or by mating features 500, 520 and 521 on each that facilitate transfer (see FIGS. 19 and 20). Such devices are described in detail in the section addressing an integrated single-use device for nucleic acid testing.

Detailed Description of Amplification Methods

In the present invention, where electrochemical detection is preferred, the main objective of the nucleic acid amplification step is to generate about a 0.01 picomolar concentration of detectable nucleic acid from the target molecule, as it has been found that this is in the range of the lower detection limit of a sandwich assay with enzymatic amplification and electrochemical detection. The desired one picomolar concentration of fragment is based on Avogadro's number (1 mole=6× 10(23) molecules), where 1 pmol equals 6×10(23)×10(−12), or about 10(12) molecules. If, as is known, one microliter of blood contains about 5×10(3) molecules of DNA, then one milliliter, which is a reasonably accessible sample volume, contains 5×10(6) molecules, or roughly about 10(7) molecules. To go from the amount of DNA in 1 ml of blood to 0.01 pmol of DNA requires an amplification of about 10(3) fold. This is certainly achievable using several well-known amplification techniques. Performing a similar calculation, for a different sample types and sample volumes, to determine the degree of amplification will be apparent to those skilled in the art.

In alternative embodiments of a single-use cartridge where optical detection is used, again the objective of the nucleic acid amplification step is to generate a given molar concentration of detectable nucleic acid from the target molecule so as to be in the range of the lower detection limit of the given optical methods. Such calculations will be familiar to those skilled in the art. It is well known in the art that the ability to determine the concentration of a sample via optical detection is dependent on the background level of noise, the extinction coefficient of the optical compound to be detected, the optical system's electronic gain, the volume of the sample and other parameters. A simple relationship between the compound concentration and the absorbance of the sample can be expressed using the Beer-Lambert law ($A=\epsilon cl$), where A is the absorbance, $\epsilon$ s is the extinction coefficient, c is the molar concentration of the sample, and l is the path length of the sample. Typically the length is 1 cm by definition, (though in the devices described below about 0.02 to about 0.4 cm is more typical). This makes the absorbance related to the concentration using the constant of the extinction coefficient and usually permits detection limits within the pM range.

Polymerase Chain Reaction Amplification

The polymerase chain reaction (PCR) is well known for its ability to specifically amplify regions of target DNA based on the primer sequences chosen for the PCR reaction. A difficulty with processing this material is in trying to detect the signal based on hybridization homogeneously. By definition, the PCR reaction generates blunt ended double stranded products. However, certain thermostable DNA polymerases possess polyA polymerase activity, which can be used to add an additional A nucleotide. While this has been used commercially for cloning purposes, the single nucleotide overhang is inefficient for hybridization. As another approach to attempt to use the PCR reaction for hybridization, recognition sequences for restriction endonuclease enzymes have been designed into the PCR primers. However, this is limiting, because it requires additional enzymes which typically only generate short overhangs. As with mostly double stranded species, the PCR product is not amenable to hybridization in homogenous reactions. To overcome this limitation, a strategy which uses a limiting amount of one primer over the other has been devised. An alternative is to have promoter regions for bacteriophage RNA polymerases (e.g. SP6). Limiting one of the primers has drawbacks in that the efficiency of the amplification is reduced. Generating RNA with bacteriophage RNA polymerases requires additional reagents and generates labile RNA species for detection.

Here we describe a novel method of performing a PCR reaction by combining DNA polymerase, a target nucleic acid and amounts of two modified primers where the first modified primer has a sequence of bases to a region of the target. A polymerase blocking region is attached to this primer which is linked to a single stranded hybridization region. The second modified primer has a sequence of bases to a second region of the target and also a polymerase blocking region and a second single stranded hybridization region. A detectable moiety (e.g. biotin, fluorocein) is attached to one or both of the two modified primers. To run the PCR reaction the mixture is cycled to generate multiple copies of an amplicon incorporating the modified primers. In a second step excess unincorporated modified primers, with the detectable moiety, are substantially eliminated from the mixture. Several different methods are available and these are described below. The mixture is then added to a capture oligonucleotide which is complimentary to one or both of the single stranded hybridization regions to permit hybridization with the amplicon. In the last step the moiety associated with this hybridization is detected directly, for example by optical detection of fluorocein. Alternatively, the moiety, e.g. biotin is exposed to and binds with a streptavidin-labeled enzyme, e.g. alkaline phosphatase and the enzyme activity is determined either optically or electrochemically. Again several specific methods are possible and examples of these are described below.

The reaction sequence is shown in FIG. 7(*a*), where 31 is the detection moiety, e.g. biotin, FAM, DNP, cholesterol, fluorocein, 32 is the first single stranded hybridization region, 33 is the polymerase blocking region, e.g. hexaPEG, 34 is the first PCR primer, 35 is the second PCR primer, 36 is the second single stranded hybridization region, 37 is a second detectable moiety, 38 is the double stranded nucleic acid target sequence, 39 is a solid substrate, e.g. bead or surface, and 40 is a hybridization region complementary to 36.

The PCR primers, 34 and 35 are preferably synthesized using standard phosphoramidite chemistry and can include any nucleotide or modified base which is amenable to DNA polymerase, except in the polymerase blocking region 33. An example of a polymerase blocking region sequence can consist of the spacer phosphoramidite 18-O-dimethoxyltrityl-hexaethyleneglycol,1-[(2-cyanoethyl)-(N,N-diisopropyl)]-phosphoramidite (hereinafter referred to as "HPEG"). This phosphoramidite generates a hexaethyleneglycol spacer region. Other spacer molecules with similar properties can also be used for this purpose. Alternatives to phosphoramidite chemistry can be used including creating a 3'-3' or 5'-5' phosphodiester backbone, as well as modified nucleotides as described by Newton et al., (Nucleic acids research 21, 1155-62, 1993) and also U.S. Pat. No. 5,525,494.

Allowing PCR to proceed using these synthetic oligonucleotide primers in the presence of the appropriate target and DNA polymerase with associated components, generates a newly synthesized DNA molecule with incorporated single, stranded regions 32 and 36. It has been found that while the Taq DNA polymerase may be used, the preferred embodiment uses *T. kodakiensis* DNA polymerase which exhibits a significantly higher turnover number. This molecule can then be hybridized by means of 36 to a target sequence 40 on a solid support 39. The binding moiety region can then be used for generating a signal. For example by using biotin as the binding moiety and using streptavidin conjugated to a detection enzyme, e.g. horseradish peroxidase (HRP) and alkaline phosphatase (ALP).

The PCR primer also preferably contains a terminal phosphorothioate bond, preventing the exonuclease activity of *T. kodakiensis* KOD1 DNA polymerase from not discriminating allelelic differences in primers used in SNP analysis based on the terminal base being different.

In the preferred embodiment using human genomic DNA isolated using the filter holder device described above, two synthetic oligonucleotides (primers 1 and 2) were used to generate a region of the human hemochromatosis gene (hfe) of approximately 390 bp in size.
These were oligo 1:

```
5'-ACTTCATACACAACTCCCGCGTTGCATAACT-HPEG-TGGCAAGGG
TAAACAGATCC-3' and (SEQ ID NO: 12)
and oligo 2:
5'-56-FAM-AACAATACCACCGTAGCGATCA-HPEG-AACAATACCA
CCGTAGCGATCA-3' (SEQ ID NO: 13),
``` where 56-FAM is a fluorescent species and HPEG is a hexaPEG sequence incorporated using an 18-O-dimethoxyltritylhexaethyleneglycol, 1-[(2-cyanoethyl)-(N,N-diisopropyl)]-phosphoramidite. In the oligo 1 sequence, the sequence located 5' to the HPEG spacer, 5'-ACTTCATACACAACTC-CCGCGTTGCATAACT-3' is designated as SEQUENCE ID NO. 1 and the sequence located 3' to the HPEG spacer, 5'-TG-GCAAGGGTAAACAGATCC-3' is designated as SEQUENCE ID NO. 2. In the oligo 2 sequence, the sequence located 5' to the HPEG spacer, 5'-AACAATACCACCG-TAGCGATCA-3' is designated as SEQUENCE ID NO. 3 and the sequence located 3' to the HPEG spacer, 5'-AACAATAC-CACCGTAGCGATCA-3' is designated as SEQUENCE ID NO. 4.

To demonstrate the use of these primers, a buccal cell DNA sample originating from mouthwash (Scope brand) was used.

A volume of 3 µL of this bodily fluid was dispensed onto a 5 mm diameter disc punched from Whatman 4 filter-paper impregnated with 3 µL of lytic salt and detergent solution comprising 2M guanidinium isothiocyanate, 1% Triton-X-100, 10 mM Tris buffer at pH 8.8 and 2 mM EDTA. After extraction, the filter-disc was placed immediately into a 0.5 mL MβP Easystart PCR reaction tube (Fisher Scientific, PN 21-402-49) designed to be filled to 100 µL. The tube is supplied with 50 µL of fluid under a wax-layer to give a final concentration of the following reagents in 100 µL of aqueous solution; 2 mM MgCl$_2$, 20 mM Tris pH 8.4, 50 mM KCl and 0.2 mM dNTP. A 47 µL upper-layer reaction mixture was added to give a final reaction concentration of primers 1 and 2 of 0.31 pM, described (Integrated DNA Technologies Inc). This aqueous solution also contained 5U Vent (exo-) polymerase (New England Biolabs) and 0.1% Triton-X-100. The amplification reaction was performed in a Techne Techgene Thermocycler. The sequence was amplified using 3 cycles of 97° C. for 3 min, 60° C. for 1 min and 72° C. for 1 min, followed by 36 cycles of 97° C. for 1 min and 62° C. for 45 s. Samples resulting from the amplification procedure were then tested in single-use cartridges using 100 µL aliquots. A complete description of the design elements of detection cartridge containing an electrochemical sensor is found in jointly owned US 20030170881 incorporated here by reference. A general description of chronoamperometry and other electrochemical methods applicable to sensors incorporated into single-use test cartridges is found in jointly owned U.S. Pat. No. 5,112,455 incorporated here by reference.

Figure 7A:
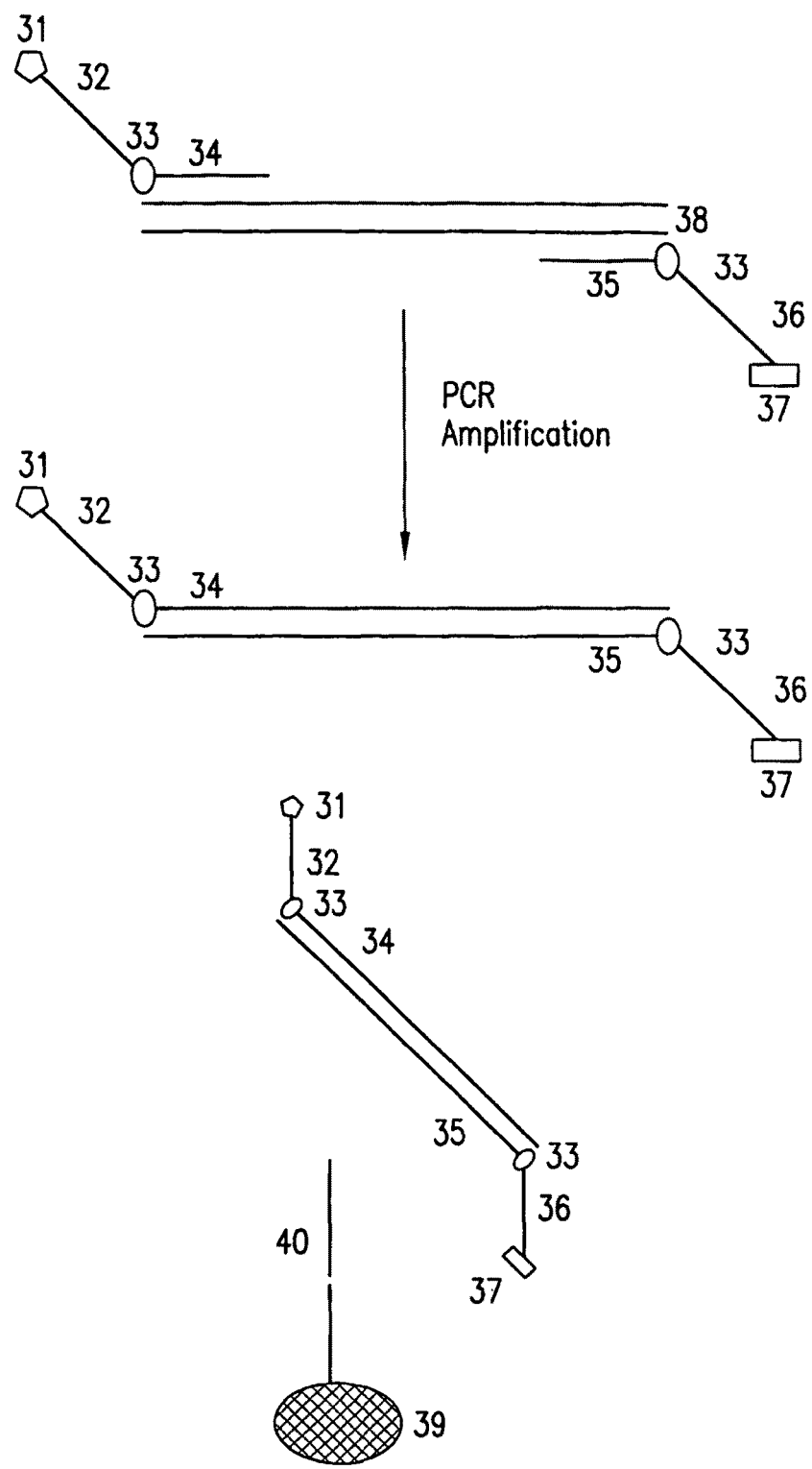
FIG. 7(a) shows a schematic of the PCR amplification method.
Figure 7B:
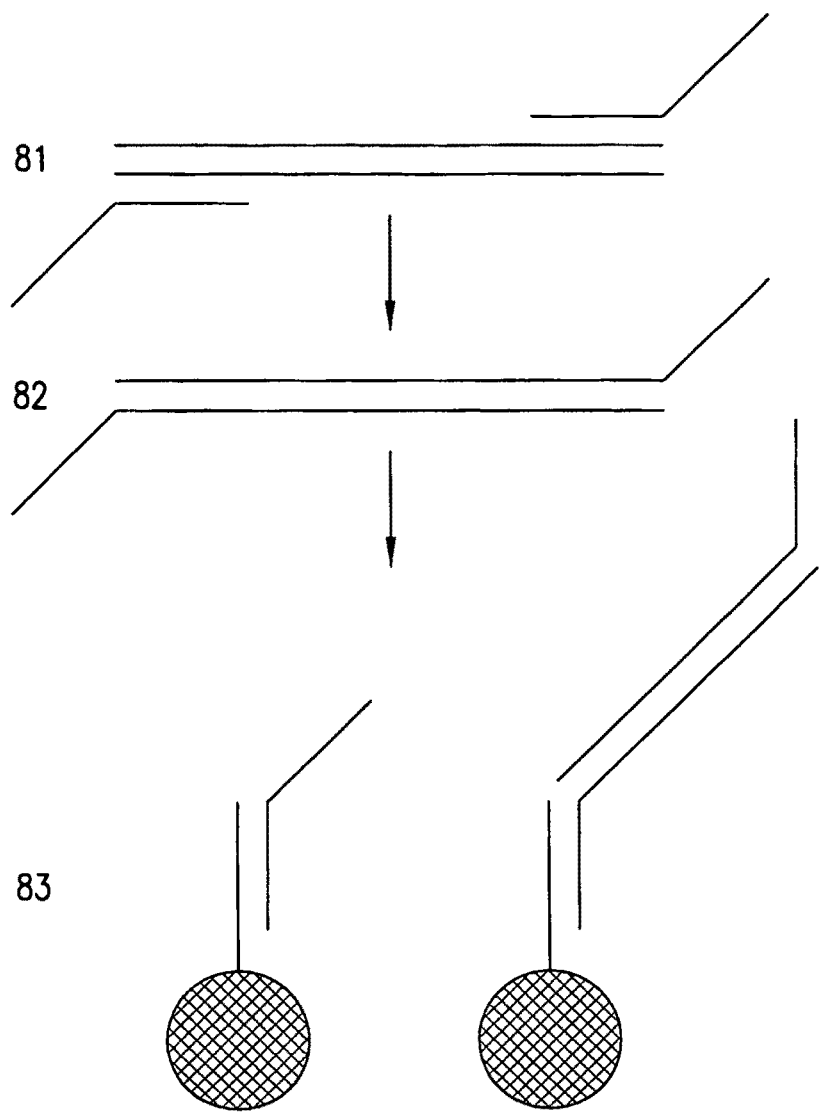
FIG. 7(b) shows a schematic of PCR amplification without a self-annealing primer and FIG. 7(c) shows a schematic of PCR amplification with a self-annealing primer.

The 100 uL aqueous aliquots were prepared as follows; 14 µL 1M NaCl, 1 µL FITC-ALP conjugate ¹⁄₁₀₀ dilution, and 10 µL amplified DNA. The FITC-ALP conjugate is a final concentration of 350 ug/ml. Alternatively a control oligonucleotide sequence was used in place of the amplified DNA. The control oligonucleotide sequence was manufactured as a positive control for chronoamperometric detection. This single-stranded sequence is analogous to 36 as shown in FIG. 7(a) and is complementary to region 40 and contains a 36-FAM fluorescent species. Note that FIG. 7(b) shows the undesired competition of a standard primer in the detection step, whereas with the clam-like primer, as in FIG. 7(c) this is obviated. The results from both of these samples are shown in FIGS. 8(a) and 8(b). FIG. 8(a) shows the chronoamperometric reading for anti-FITC ALP conjugate alone versus the conjugate with amplicon hybridized to the sensor. FIG. 8(b) shows the chronoamperometric reading for anti-FITC ALP conjugate alone versus the conjugate with a positive control oligonucleotide sequence.

The detection cartridge operated as follows, a 20 µL portion of the 100 uL aliquots was loaded into an enzyme-linked DNA hybrid sensor cartridge, as described in jointly owned US 20030170881 and placed into an i-STAT model 300 electrochemical analyzer (i-STAT Corporation). The sensor cartridge contained multiple (2 or 4) amperometric sensors coated with specific DNA oligomers. In this example, the oligomers were 5'-biotinylated oligonucleotides and were bound to streptavidin-coated beads which were adsorbed onto the sensor surface. One of the sensors was coated with the complementary single-stranded DNA oligomer to one of the single-stranded portions of the PCR primers, as a control. Also present within this cartridge was a separate anti-FAM-alkaline phosphatase conjugate.

In the preferred embodiment, the PCR amplified product and anti-FAM ALP conjugate dissolved into a single solution were brought into contact with the DNA capture sensors. Note that alternatively the PCR product may be contacted with the sensor first, followed by the conjugate. In the preferred embodiment, the double-stranded PCR products, containing both single-stranded hybridization regions, binds to the capture region on the amperometric sensor. Binding of the alkaline phosphatase label can occur either in solution before capture of the PCR product or after it has bound to the bead. After a controlled period of time, typically 5 to 15 minutes and at a controlled temperature preferably 37° C., the solution is moved out of the sensor region and delivered to a waste chamber within the cartridge. A wash solution, containing substrate for ALP, is brought over the sensor washing excess aFAM ALP conjugate away from the sensor region. A trailing portion of the wash solution remains on the sensor and provides an electrogenic substrate for the ALP label. Note that in an alternative embodiment a wash solution may be used first, followed by a second solution containing the substrate. Note also that where an optical sensor or other type of sensor is used, other appropriate substrates are used. In the preferred embodiment, the measured current at the capture sensor is essentially directly proportional to the number of ALP labels present on the sensor. An adjacent amperometric sensor which is not coated with the complementary DNA binding sequence can be used as a control sensor to offset any non-specific binding of the ALP reagent on the sensors, thus improving the detection limit. Alternatively a capture oligonucleotide with a sequence different from the complementary DNA binding sequence can be used as a negative control.

Figure 8A:
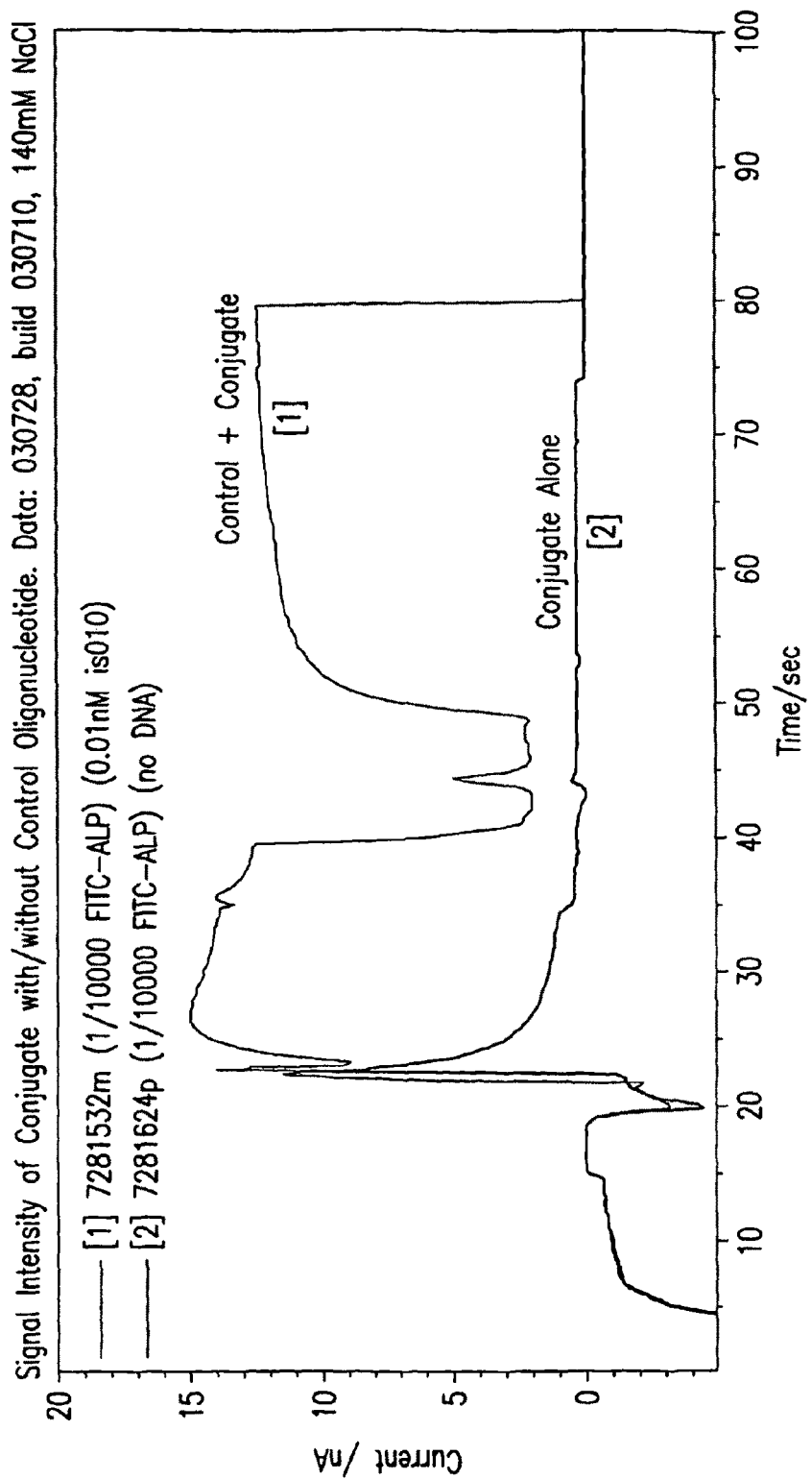
FIG. 8(a) shows a typical chronoamperometry output for PCR plus conjugate and conjugate alone.
Figure 8B:
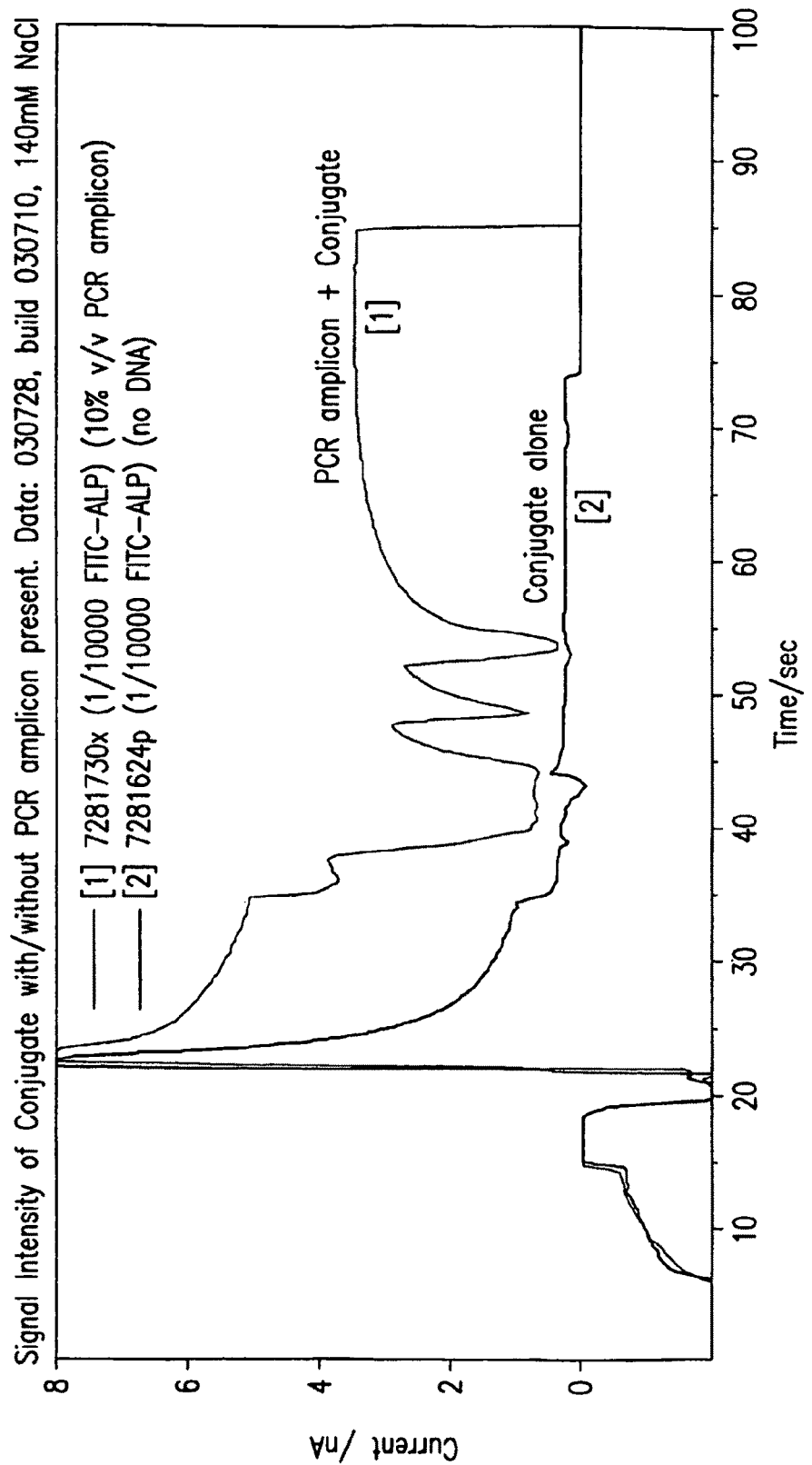
FIG. 8(b) shows a typical chronoamperometry output for control plus conjugate and conjugate alone.

Referring to FIG. 8(a) and FIG. 8(b), these show the measured current profiles, or chronoamperometric output, from DNA cartridges. PCR product with conjugate shows an increase in measured current, over conjugate alone, in FIG. 8(a). Here, competing unbound primers may be reducing signal. A similar increase in signal is observed with the positive-control oligonucleotide sequence that is labeled with 36-FAM species, as shown in FIG. 8(b). It has also been found that the net current is proportional to the number of PCR amplicons in the sample, see FIG. 9(a), where the steady-state current is shown to increases with increasing amplicon concentration. These data are plotted in FIG. 9(b).

Figure 9A:
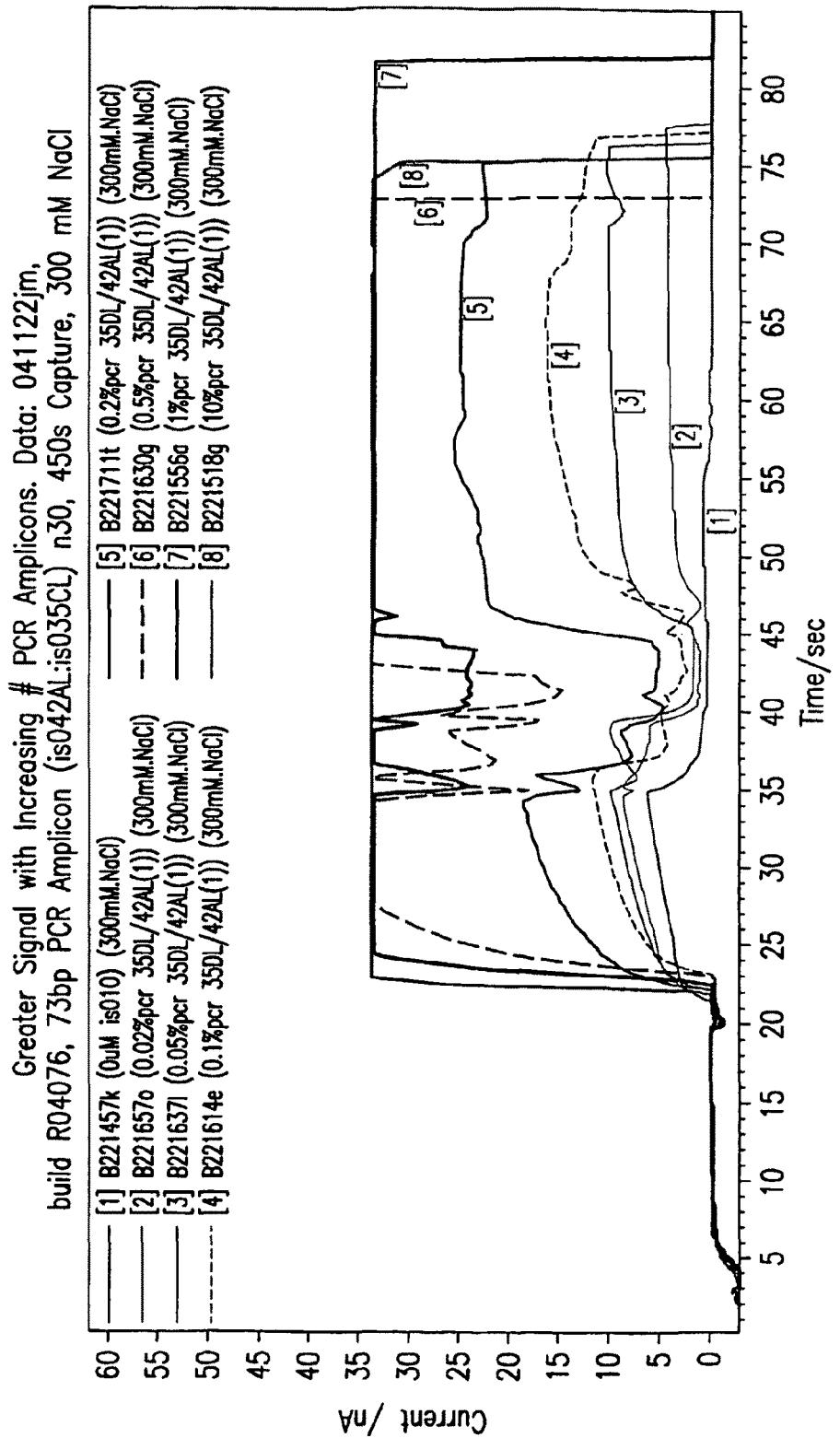
FIG. 9(a) shows chronoamperometry of different amplicon concentrations and FIG. 9(b) shows a plot of the steady-state current signal versus amplicon number.
Figure 9B:
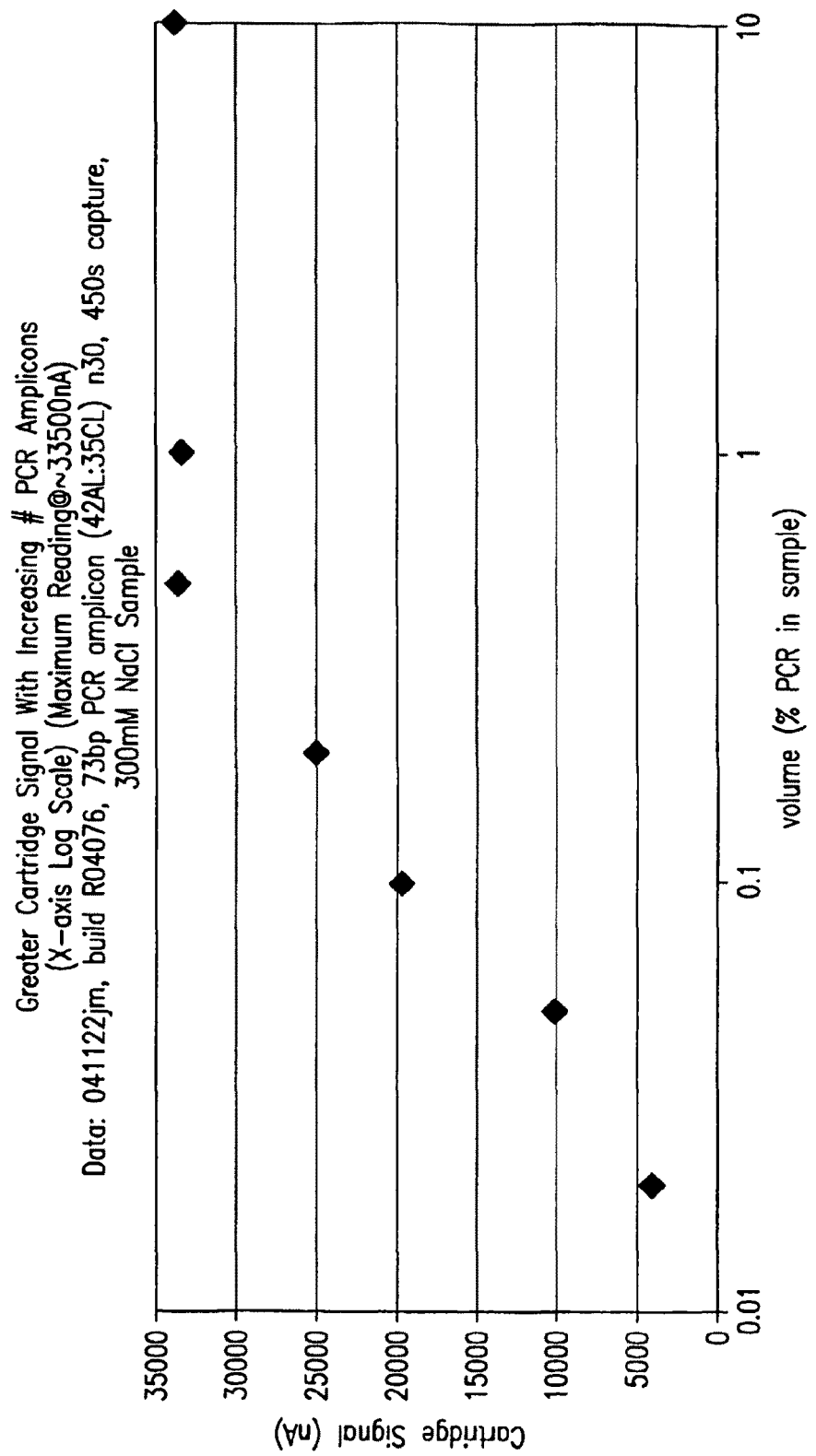

The software used for the instrument 200 and 650 (see FIGS. 6 and 21) in this example is a modified i-STAT 300 analyzer (i-STAT Corporation) which performs a series of steps in the detection process. In the first step, the instrument makes contact with and identifies the cartridge, and then conducts a battery check and other internal instrument checks. It then initiates and completes a thermal cycle to heat the sensor chip to 37° C. The liquid containing the amplified target is then pneumatically pushed from conduit 125 into the sensor chamber 126 to permit the capture steps. A push pin 213 in the instrument then makes contact with element 135 during the second motor motion of the instrument causing the analysis fluid 134 to be dispensed from the analysis pack into the analysis into conduit 125 which acts a temporary holding chamber. The temperature set-point for the sensor chip is then increased to 47° C. and a conductivity sensor on the chip is initialized. The target liquid is then pushed back and forth over top of the capture oligonucleotide beads to effect efficient capture of the amplicon. This step takes about 3 to 9 minutes. Note that the conductivity sensor is used to monitor the position of the fluid during this capture process. Before the last two oscillations, the software in the instrument causes the heating of the chip to be turned off and the remaining cycles are conducted at ambient temperature. The liquid containing the uncapture amplicon is then moved slowly to the sample inlet side of the waste chamber 137, and the sensors are set to collect data at a poise potential of +30 mV vs. Ag/AgCl electrode (at 2 pA/bit). As this liquid is pushed into the waste chamber a locking wick mechanism closes a vent when it becomes saturated. This mechanism is of the type described in jointly owned US 20030170881 which is incorporated here by reference. The software then causes the instrument to actuate the cartridge such that analysis fluid is drawn across the sensors to wash the remaining unbound material from the capture oligonucleotide, leaving a thin layer of analysis fluid containing p-aminophenol phosphate which can react with the enzyme and be oxidized at the electrodes. Current generated as a function of time is recorded, as shown in FIG. 9(a), and can be used by the software algorithm to display a result.

Figure 31:
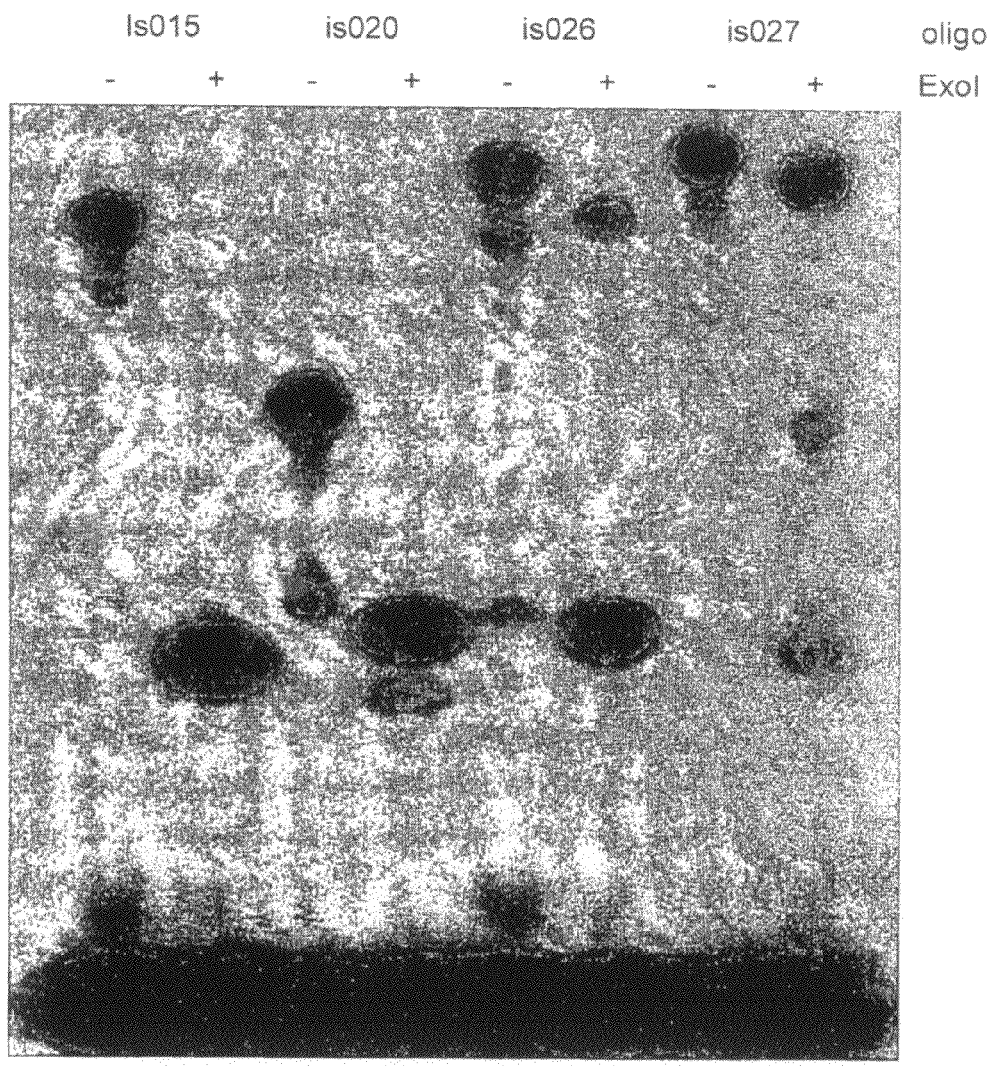
FIG. 31 shows an autoradiograph of 32P radiolabelled synthetic oligonucleotides demonstrating that the ExoI enzyme is an active 3'→5' exonuclease, which has the ability to reduce the molecular weight down to about 6-7 nucleotides in length.

It is known in the art that ExoI can be used to degrade un-incorporated single stranded oligonucleotides in DNA sequencing reactions, however it was not known if unnatural DNA, like the hexa-PEG region would be degraded by the ExoI enzyme. To demonstrate that ExoI works on this unnatural base, the experiment shown in FIG. 31 was performed. This figure shows an autoradiograph of 32P radiolabelled synthetic oligonucleotides after ExoI treatment. In FIG. 31, the is015 oligonucleotide in lane 1 is the same as oligo 1 above. The oligonucleotides labeled is026 and is027, like is015 contained an HPEG spacer, while the iso20 oligonucleotide did not contain an HPEG spacer. FIG. 31 demonstrates that the ExoI enzyme is an active 3'→5' exonuclease, which has the ability to reduce the molecular weight down to about 6-7 nucleotides in length. Further, it can process past the hexa-PEG region and it is inhibited in the double stranded region of the clam primers. Therefore, it demonstrates that ExoI is not prevented from being an exonuclease with the hexa-PEG region.

In another embodiment of the invention, gene copy mutations, e.g. ZNF217, are detected by using both the target gene and one or more housekeeping genes, e.g. actin or glyceraldehyde-3-phosphate dehydrogenase. This is accomplished with two sensors in the detection chamber 126, with one for the target and the other for the housekeeper. Here, PCR primers are used to amplify both the housekeeping gene, as well as the gene of interest. If ZNF217 is present in the same copy number as the housekeeping gene, the level of signals is similar. However, when the ZNF217 gene is present in multiple copies, the level of signal at the ZNF217 sensor is greater than at the housekeeping gene sensor.

Another embodiment of the invention addresses genetic mutations which causes disease states includes gene expression mutations. Wildenhain et al., (1990, Oncogene, vol 5 (6):879), describe the over-expression of the neu protein-tyrosine kinase, p185neu which is related to breast cancer. The c-Myc oncogene has been identified in many forms of cancer (Waikel et al., 1999, Oncogene, vol 18 (34):4870). Other examples of oncogene overexpression were described by Ren (2004, Curr. Opin. Hematol. Vol 11 (1):25). Overexpression mutations typically generate increased levels of mRNA, thus to detect mRNA in this invention, an initial step of cDNA synthesis is used prior to the PCR amplification. The synthesis of cDNA using reverse transcription is well known in the art, including amplification of this material by PCR. Using the PCR amplification previously described, the presence of a quantity of mRNA present in a cell can be determined by measuring the level of the signal. Comparing the signal for a particular oncogene, for example Her2/neu to a housekeeping gene allows the discrimination of oncogene expression at normal levels, or at levels indicative of a disease state, and in particular with breast cancer in the case of Her2/neu.

Figure 26:
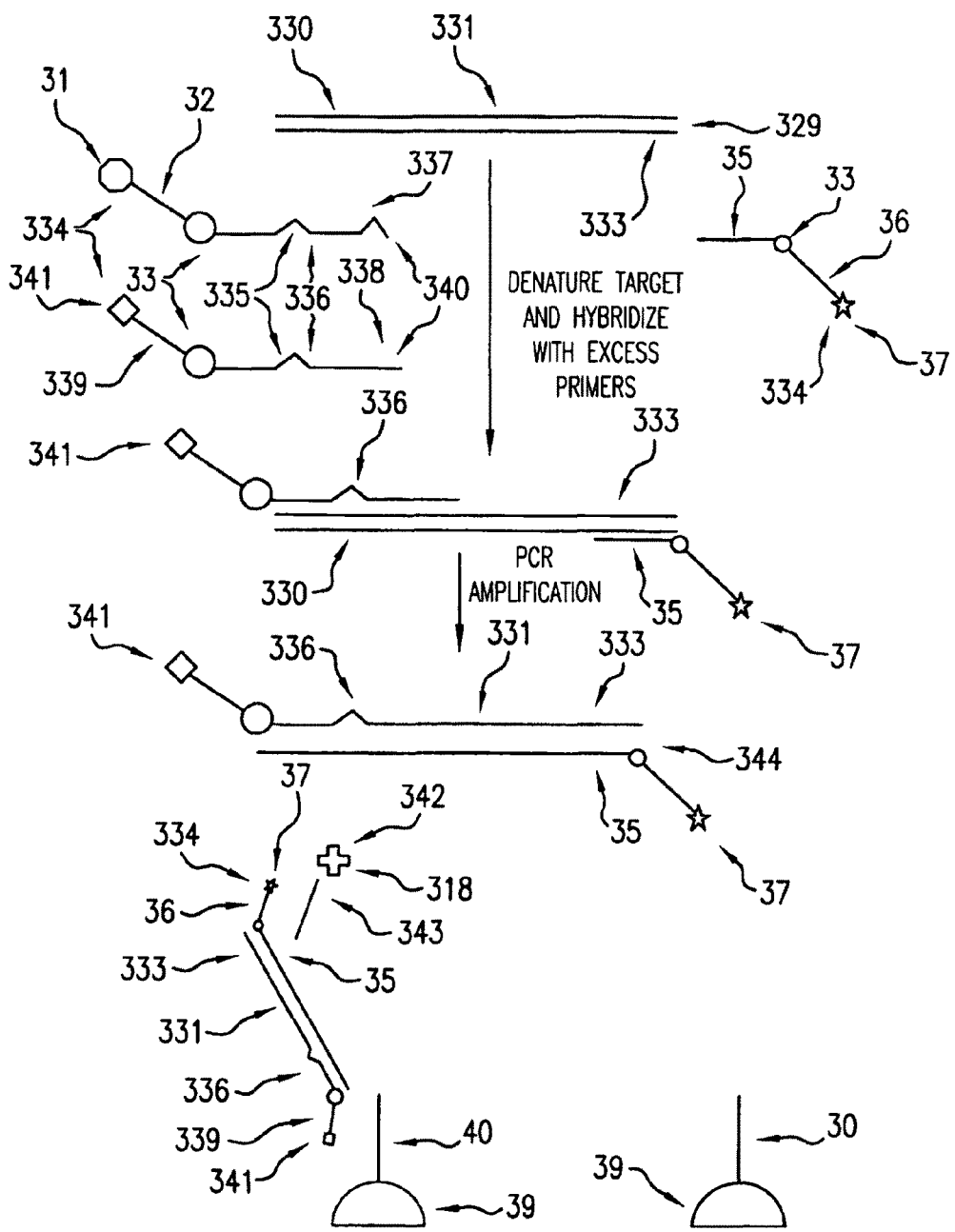
FIG. 26 shows a schematic of the PCR amplification method which differentiates between mutant and wild-type SNP sequences.
Figure 32A:
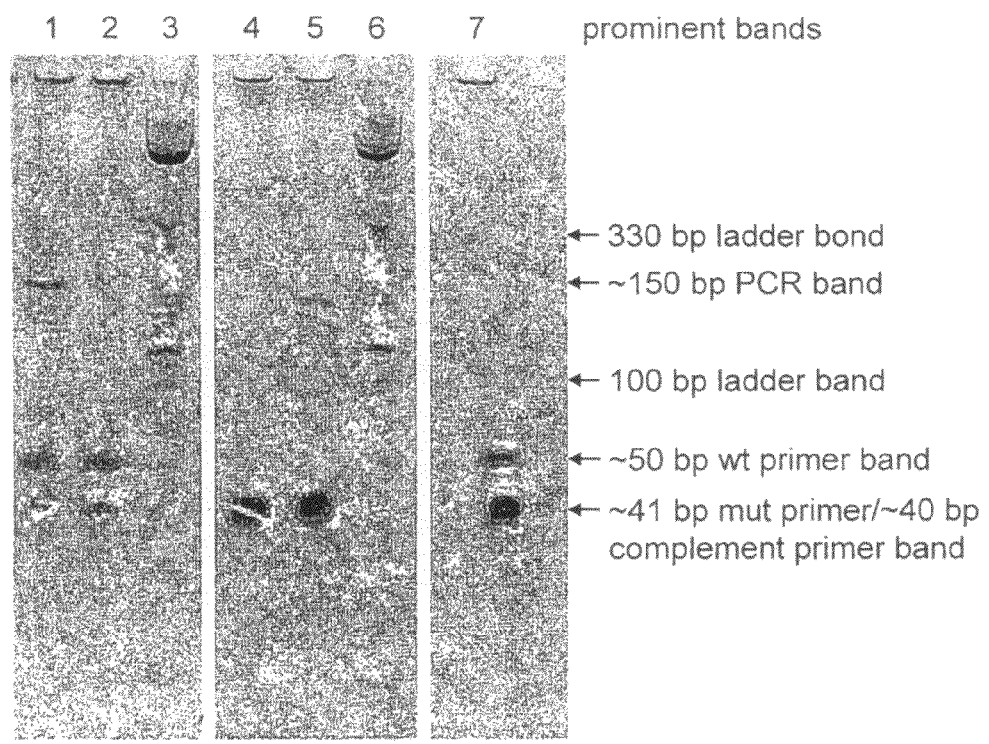
FIG. 32(a) shows PCR with phosphorothioate primers discriminating between wt/mut DNA templates using a 10% non-denaturing polyacrylamide gel; 6 uL sample+1.6 uL LD→6 uL loaded in each well (45 min SYBR Gold stain, photo-negative, experiment HFE 84-2, $T_{hyb}$ 68° C. The seven columns were loaded as follows; 1 wildtype-selective PCR primer present with wildtype DNA template, generates anticipated ~150 bp band; 2 wildtype-selective PCR primer present with mutant DNA template, does not generate anticipated ~150 bp band; 3 a 10 base-pair ladder, prominent bands at 100, 330 and 1660 bases; 4 mutant-selective PCR primer present with wildtype DNA template, does not generate anticipated ~150 bp band; 5 mutant-selective PCR primer present with mutant DNA template, generates anticipated ~150 bp band; 6 a 10 base-pair ladder, prominent bands at 100, 330 and 1660 bases; and 7 both selective PCR primers present with wildtype DNA template, does not generate any band.

FIG. 26 shows an alternative assay method schematic and experimental data for this method are shown in FIG. 32(a) by gel electrophoresis and FIG. 32(b) by chronoamperometry.

Target nucleic acid (DNA or cDNA) 329 is shown flanked by two regions where PCR and/or Clam primers bind 330 and 333, with an intervening sequence marked by 331. During the PCR reaction, three primer sequences 31, 341 and 37 are added to the reaction mixture, wherein 31 and 341 differ by a single nucleotide at their 3' end 340 as indicated by 337 and 338.

Elements 31, 341 and 37 act as PCR primers, wherein region 336 for primers 31 and 341 hybridize to region 330 on target molecule 329. And region 35 of molecule 37 hybridizes to region 333 on target molecule 329. Primer 37 can function as a complementary PCR primer for primers 31, 341 or both 31 and 341. Primer 37 also has the feature of a specific sequence of bases at region 35 wherein it hybridizes to target molecule 329 at location 333. It has a DNA polymerase blocking group at 33, another unique region at 36 which will form a single stranded region for later hybridization during detection and an optional binding moiety at 37.

Clam primers 31 and 341 have many similar features, but also have some specific differences. Both clam primers 31 and 341 have an optional detectable moiety at 334, This is for example a biotin molecule on 31 and a FAM tag on 341. However, these are different for 31 and 341 to allow later discrimination of the molecule. Both clam primers 31 and 341 have different designed single stranded binding regions 32 and 339 respectively. In addition, both clam primers 31 and 341 have DNA polymerase blocking groups 33 and both clam primers 31 and 341 have a point mutation designed into the fourth nucleotide base to assist in the discrimination of single nucleotide polymorphisms, as described by Lee et al., (2004, Nucleic Acids Research, vol 32 (2):681), Newton et al., (1989, Nucleic Acids Research, vol 17 (7):2503), and European Patent application No. 89302331.7. As already mentioned, region 336 of both clam primers 31 and 341 bind to region 330 on target molecule 329, wherein a single nucleotide mutation at 337 or 338 discriminates between a single nucleotide difference. Both clam primers have a modified terminal phosphodiester bond at 340 that is resistant to 3' to 5' exonucleases present in certain thermostable DNA polymerases, which further assists in the discrimination of the two different molecules. This modified terminal phosphodiester bond can be a phosphorothioate or peptide nucleic acid (PNA). The Clam primers also have the feature of having intramolecular structure, which prevents the unincorporated single stranded primer molecules from binding to a capture oligonucleotide 40 or 30 at the detection stage, but permits them to hybridize to the capture oligonucleotides 40 and 30 if incorporated into a newly synthesized PCR amplicons.

In the first round of PCR after denaturation of the double stranded target to single strands, primer 37 and either clam primers 31 or 341 or both 31 and 341 bind to target molecule 329. When only either clam primer 31 or 341 binds to the target molecule 329 as is the case for a homozygote, the single nucleotide on both copies of two chromosomes are the same. When both 31 and 341 bind to two separate molecules of target 329 as is the case for a heterozygote, one chromosome has one single nucleotide base sequence, whereas the other chromosome has a different single nucleotide base sequence as is found in single nucleotide polymorphisms. This incorporates clam primers 31 or 341 or both 31 and 341, as well as the PCR primer at the other end, 37 and the newly synthesized intervening region 331.

PCR amplification is allowed to proceed for between 15 and 50 cycles to generate newly synthesized amplified molecules. In FIG. 26 we show an amplicon 344 with Clam primer 341 incorporated. This is done for illustrative purposes. If the other mutation were present, or if there was a different sequence on either of the chromosomes, an amplicon with 31 incorporated would be found. For simplicity, only the amplicon with 341 is shown in the figure.

During the detection step of the process, the newly synthesized PCR amplicon 344 with Clam primer 341 and PCR primer 37 incorporated binds to capture oligonucleotide 40 at region 339 based on the nature of complementary sequences binding to each other. Sequence 339 does not bind to a different physically separated capture oligonucleotide 30 which possesses a different sequence. Both capture oligonucleotides 30 and 40 are bound to a solid substrate or beads as indicated in 39.

The detection of this hybridized complex can either be detected by a conjugate molecule which binds to binding moiety 334 in molecule 37, or another single stranded oligonucleotide 318 binding at region 343 with region 36 on molecule 344 having its own detectable moiety 342 which can be detected by a conjugate molecule. The conjugate molecule has two features: (i) a region that binds to the binding moiety 334 or 342, and (ii) a detection region. An example is an antibody specific for the FAM binding moiety, which has been modified with an alkaline phosphatase enzyme as the detection element.

Alternative Amplification Methods

Figure 10:
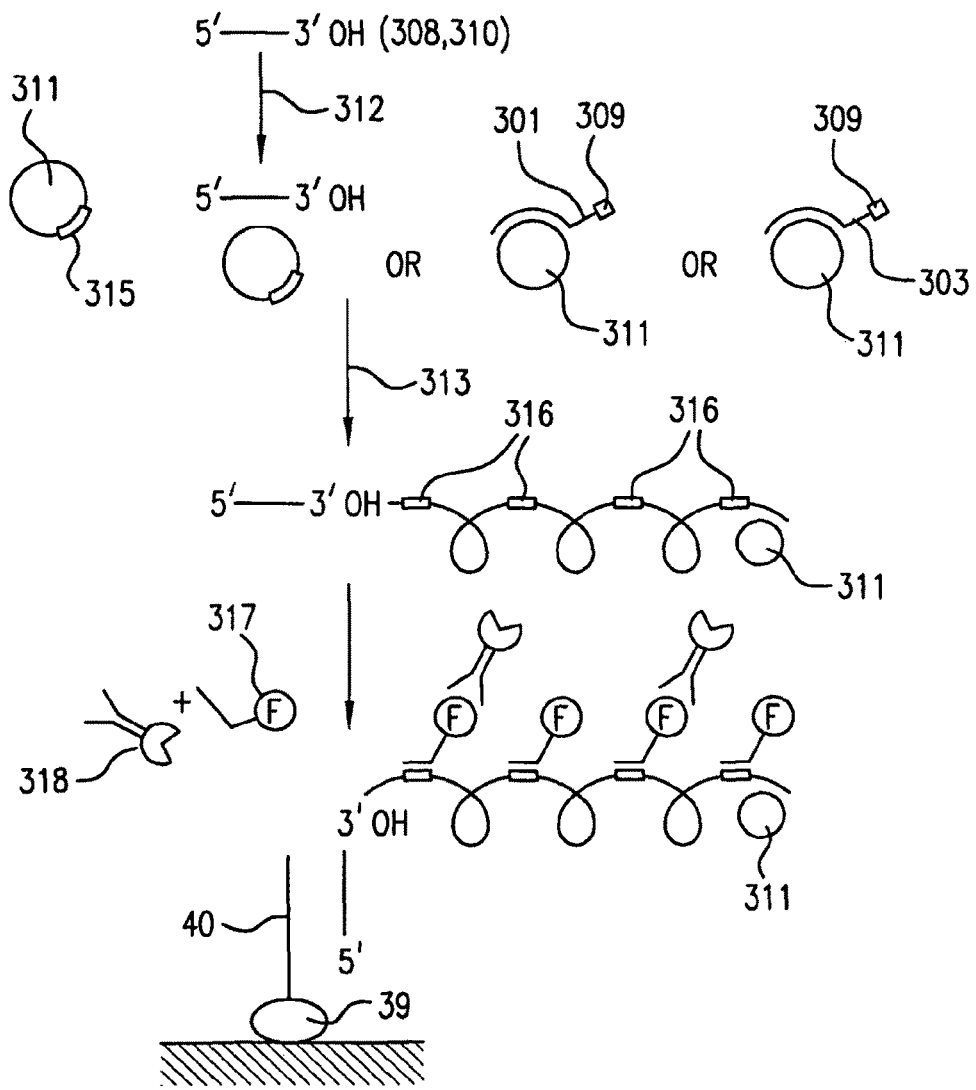
FIG. 10 shows a schematic for rolling circle amplification (RCA)
Figure 25A:
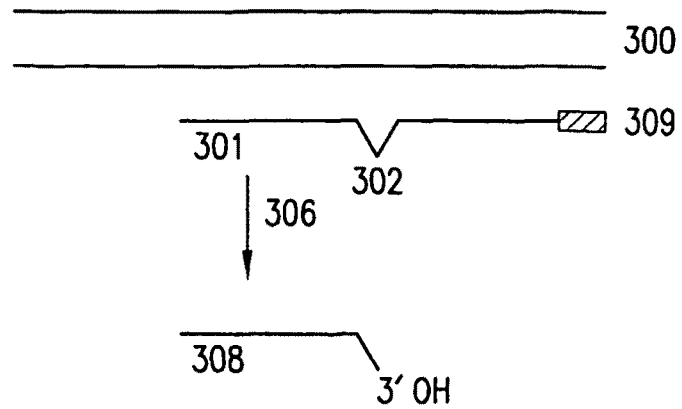
FIG. 25(a)-(b) show a cleavage reaction creating a "trigger event" for further amplification and detection.
Figure 25B:
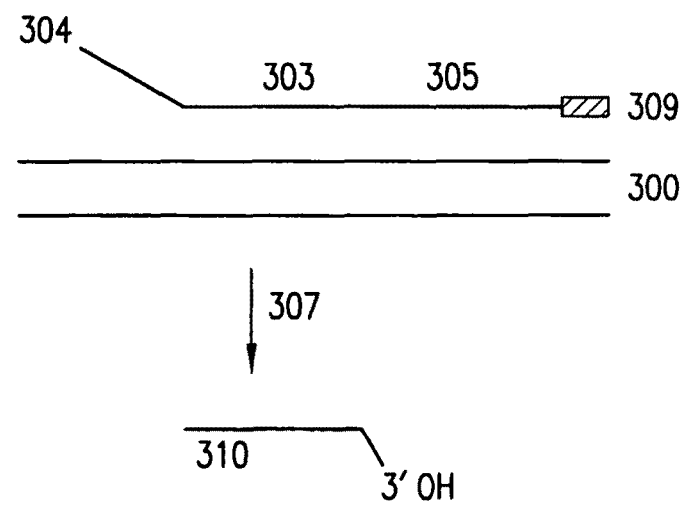

An alternative embodiment of this method using the same detection cartridge can be used to perform a non-PCR nucleic acid amplification assay. A schematic for rolling circle amplification (RCA) is shown in FIG. 10 and one for strand displacement amplification (SDA) in FIG. 11. Note that the component elements correspond to those described for PCR as shown in FIG. 7(a). Both assays require a short ssDNA fragment with a 3'-OH moiety (308 and 310) made from the target, as shown by means of two different methods in FIG. 25. FIG. 25(a) shows a triggering event method, e.g. SNPase and cycling probe, and FIG. 25(b) shows the Invader™ method.

The same reagents are used as in the above section, however only one modified primer comprising a sequence of bases to a first region of said target nucleic acid is required. Again the mixture is cycled to provide multiple copies of an amplicon incorporating the modified primer, followed by substantial elimination of any excess unincorporated modified primer from the mixture. Several methods can be used as discussed below. The mixture is then exposed to a capture oligonucleotide complimentary to the single stranded hybridization region, followed by hybridization of the single stranded hybridization region of said amplicon incorporating said modified primer, with the capture oligonucleotide. Again the final step is detecting said moiety associated with said hybridization, e.g. electrochemical detection of an electroactive species generated by alkaline phosphatase. In the preferred embodiment, primers are attached to the polymerase-blocking region which, in turn is attached to a single stranded hybridization region.

For the rolling circle amplification strategy, the 3'-end of the primer has a blocking region, which could include a phosphate or a dideoxy nucleotide. A cleavage reaction similar to that found for the cycling probe reaction or the SNPase assay occurs, removing the blocking moiety, as shown in FIG. 25(a), comprising target DNA 300 and reagents 301, 302 and 309 participating in reaction 306. Pre-made circular molecules can be added to the reaction mixture. Extensions cannot occur with blocked primers, but do occur to cleaved primer molecules. The cleaved primers generate long single stranded molecules with duplications of specific regions complementary to the pre-made circular molecules. Synthetic oligonucleotides with detectable moieties are included in the mix, wherein the oligonucleotides are complementary to a region of the single stranded DNA, which can be found multiple times along the single stranded DNA. One region of the primer, which is single stranded and unique, binds to a capture oligonucleotide region. As this region is not complementary to the pre-made circular DNA, there is no competition of this region with the capture oligonucleotides. As shown in FIG. 10, in the rolling circle assay the ssDNA 3'-OH moiety (308, 310) binds to the rolling circle reagent (311, 315) via reaction 312. Cycling incorporates a string of moieties 316 attached starting at the 3' end of 308 or 310, to produced 314. Detection of element 314 is achieved by binding its 5'-3'-OH region to complementary element 40 immobilized on bead 39 and labeled polynucleotide 317 complementary to 316. The label is then recognized by an antibody bound to alkaline phosphatase 318.

Figure 11:
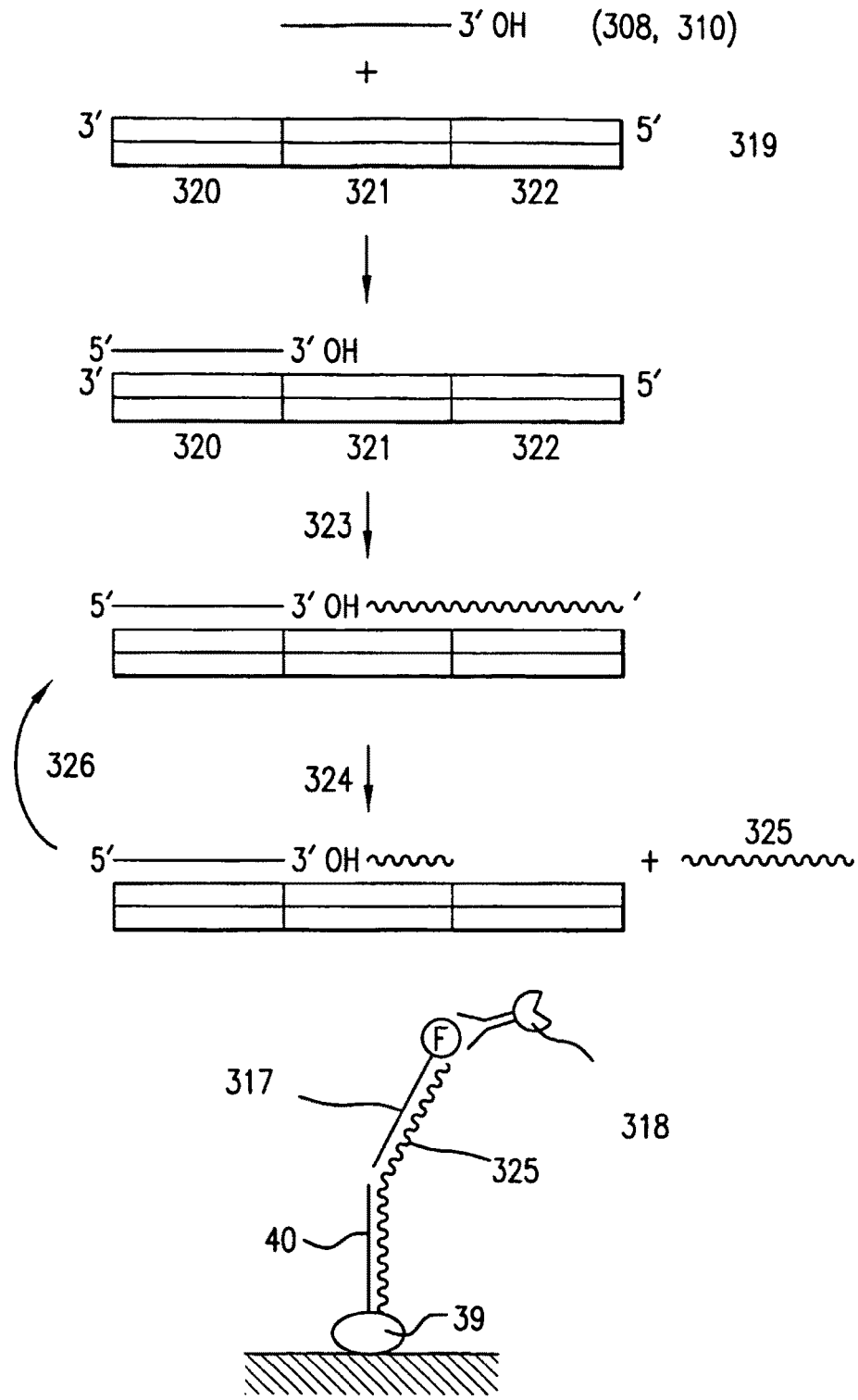
FIG. 11 shows a schematic for strand displacement amplification (SDA).

An alternative embodiment of this method using the same detection cartridge can be used to perform a non-PCR nucleic acid amplification assay. A schematic for strand displacement amplification is shown in FIG. 11. Note that component elements correspond to those in the PCR as used as in FIG. 7(a). Similar reagents are used as those described above, however the SDA primer must first be provided in a non-amplifiable format, which is converted to an amplifiable format. One approach to accomplishing this is to provide a primer with a blocked 3'-end block, for example using a 3'-terminal dideoxy sequence. A trigger event then occurs, which cleaves off the blocking 3'-end. One example of a trigger event could be an Invader reaction (Kwiatkowski R W, Lyamichev V, de Arruda M, Neri B. Clinical, genetic, and pharmacogenetic applications of the Invader assay. *Mol Diagn.* 1999; 4:353-364), where the flappase activity cleaves at the hybridized junction of the blocked primer with the presence of genomic target nucleic acid, providing an available 3'-hydroxy group. This is shown in FIG. 25(b) with target DNA 300 and reagent comprising 304, 303, 305 and 309 participating in reaction 307. Alternatively, another example of a trigger event is a cycling probe reaction (Duck et al., 1990, BioTechniques, vol 9 (2): 142), where the presence of the genomic target nucleic acid causes the cycling probe oligonucleotide to be cleaved at a four ribonucleotide sequence on the cycling probe oligonucleotide, in turn generating a free 3'-hydroxyl group. Another similar example is a mismatch to the genomic target nucleic acid and a repair enzyme, which as described for SNPase, generating a free 3'-hydroxyl group.

After the trigger event, which has generated a free 3'-hydroxyl group in the primer sequence, a complementary strand displacement primer is present. This SD primer is complementary at its 3' end for the primer described above, which generated a 3'-hydroxyl group. In addition, the SD primer has 3' to the 3'hydroxyl group complementary oligonucleotide a region that when newly synthesized is cleaved by a Nickase restriction endonuclease, as described in U.S. Pat. No. 5,422, 252. This allows the strand displacement reaction to generate many copies of newly synthesized sequence, which form the basis of a non-thio strand displacement amplification as described in U.S. Pat. No. 6,191,267. The next step in the process is to use these amplified newly synthesized fragments, complementary to the strand displacement primers as DNA bridges to generate a signal with the capture oligonucleotide, as described above. This is illustrated in FIG. 11, where in the strand displacement assay the ssDNA 3'-OH moiety (308, 310) binds to a region 320 at the 3' end of 319 composed of regions 320, 321 and 322. An extension reaction 323 then occurs which is then nicked in reaction 324 to produce a short portion of ssDNA 325 which accumulates by virtue of cycling reaction 326 of primer extensions and nicks. Detection of element 325 is achieved by binding a first portion of 325 to complementary 40 immobilized on bead 39 and a second portion of 325 to a labeled polynucleotide 317. The label is then recognized by an antibody bound to alkaline phosphatase 318.

Removal of Primers After Amplification

We describe several novel approaches to remove unused PCR primers from completed PCR reactions. It has been found that a consequence of seeking to develop systems incorporating rapid PCR reactions, i.e. completed amplification in less than about 15 minutes, that it is necessary to increase the primer concentrations. However, this typically can generate an increased primer background in the detection step, which can reduce signal generation on the capture oligonucleotide. Experiments using purified amplicons and increased unlabelled target oligonucleotides, amongst labeled control oligonucleotides, demonstrated that these background oligonucleotides were able to remove or reduce the signal. One approach or a combination of the approaches described below can be used to reduce the background signal.

One way for providing for easy removal of primers from the reaction amplification mixture is to use a clam-like oligonucleotide primer. This oligonucleotide predominantly exhibits a certain desired secondary structure in solution, when in a first temperature range, but not in a second higher temperature range. In this example, the oligonucleotide is capable of priming the target nucleic acid in the second temperature range, but not in the first temperature range. This is achieved by designing the oligonucleotide such that the primary structure results in a secondary structure with one or more regions that hybridize, preferably predominantly in an intra-molecular manner, but also in an inter-molecular manner. This can occur in the first temperature range but not in said second temperature range, thus changing the temperature will enable switching the primer between a priming and non-priming form. As a result, lowering the temperature at the end of the amplification reaction effectively removes excess primer from the mixture. It has been found that clam-like primers of this type may be prepared incorporating a polymerase blocking region, a single stranded hybridization region and optionally a detectable moiety. Alternative methods for removing primer at the end of the amplification reaction have also been devised. These are by electrophoresis, post-PCR hybridization and enzymatic conversion.

Electrophoretic Separation

Figure 12A:
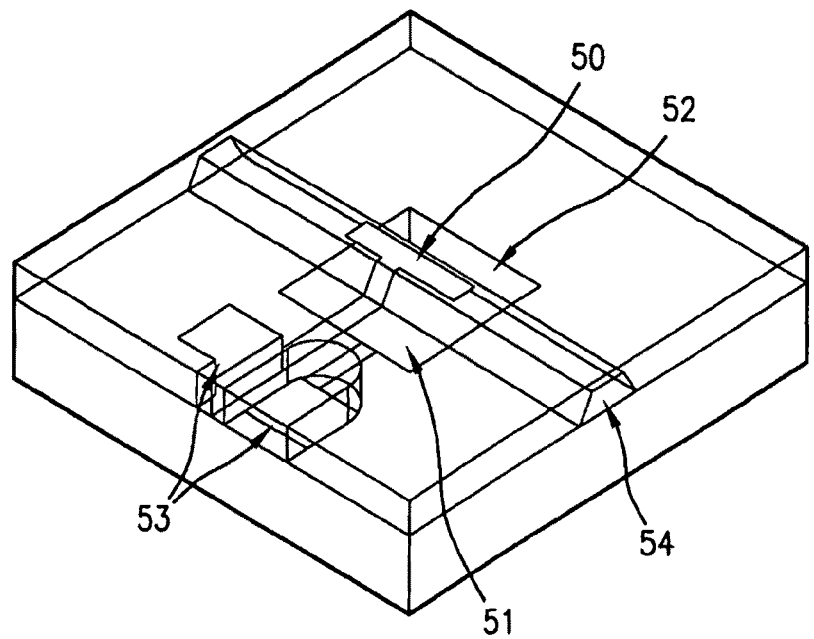
FIG. 12(a)-(b) show two perspectives of an electrophoresis component for integration into a single-use device for nucleic acid testing.
Figure 12B:
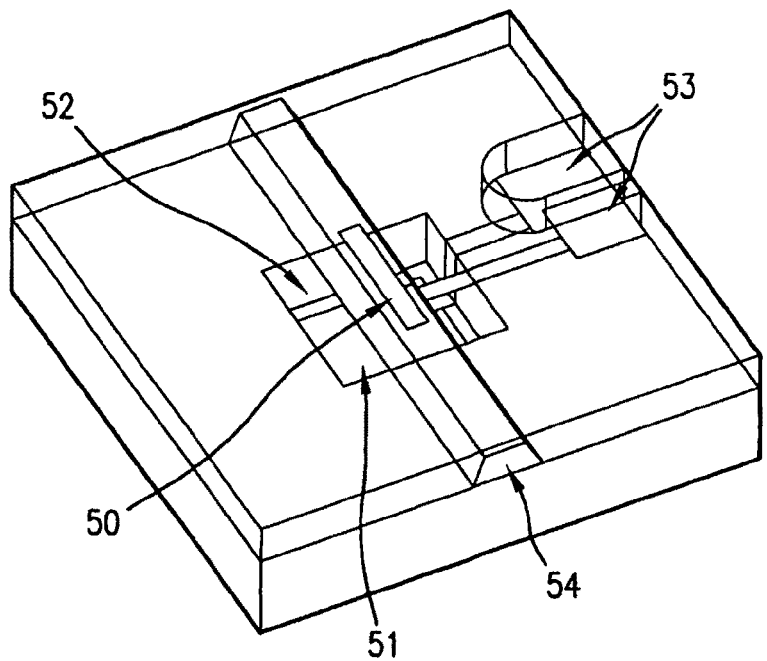
Figure 13A:
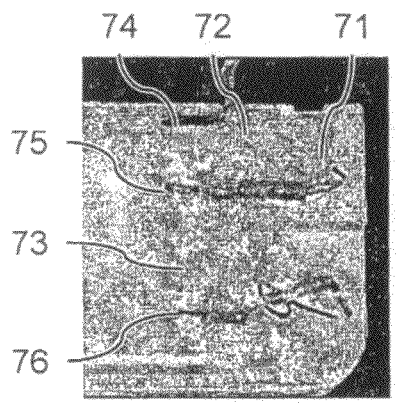
FIG. 13(a)-(g) show an electrophoretic separation using a component for integration into a single-use device for nucleic acid testing.
Figure 13B:
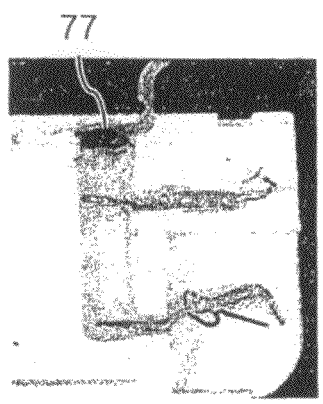
Figure 13C:
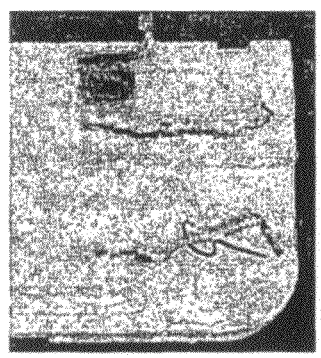
Figure 13D:
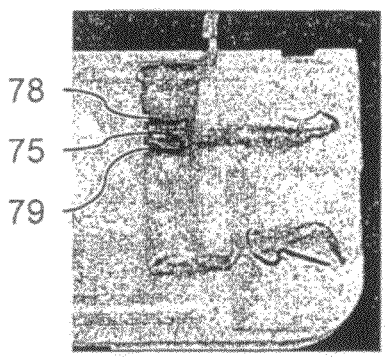
Figure 13E:
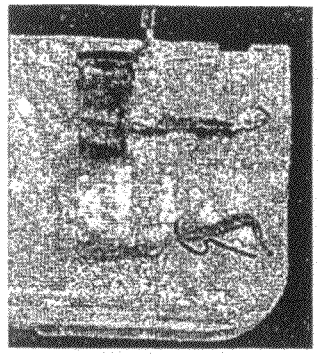
Figure 13F:
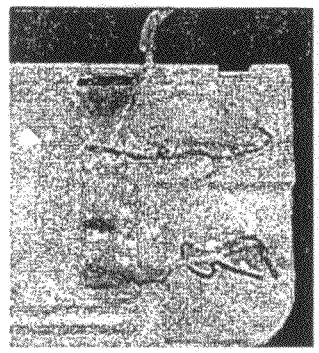
Figure 13G:
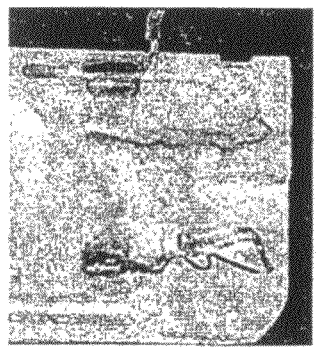

The first approach described is electrophoretic separation. It is well known that nucleic acids can be separated based on their molecular weight. By exploiting the size differences between the PCR amplicon and the oligonucleotide primers it is possible to rapidly purify the amplicon. In the preferred embodiment, an electrophoresis module is incorporated into a single-use device. For example, the electrophoretic purification module can be situated at a point along a channel in the device at a position convenient to effect purification, as shown in FIG. 12. The device is comprised of an electrode 50 in a channel of the device and a second electrode 51 in an adjacent cavity 52. Each electrode is connected to an electrical contact pad 53. A channel 54 in the device provides a means through which fluid moves from an earlier stage e.g. a PCR amplification step, to a later stage e.g. a detection step.

The purification module shown in FIG. 12 can be situated on either side of the channel and above or below. It can have two or more electrodes. For example, an additional third electrode can be situated in a position between the two electrodes that are shown. For the two-electrode embodiment shown in FIG. 12, a capture membrane for the primer sequences is used which effectively irreversibly absorbs the primer. Suitable materials include nitrocellulose, Whatman DE52 membrane, and other DNA binding membranes, well known in the art.

In one embodiment, solidified gel matrix, e.g. agarose, with an electrophoresis buffer is positioned in the cavity. A sample segment of PCR amplified material is then moved through the channel and positioned over the cavity. Optionally a second pair of conductivity electrodes can be used to sense the position of the material as it moves through the channel, as described in jointly owned U.S. Pat. No. 5,096,669 incorporated herein by reference. Once the sample is positioned appropriately, an electrophoretic charge is applied across the two electrodes, with 50 being negative, and 51 being positive. This causes electrophoretic movement of the molecules in the gel matrix, with the smaller synthetic oligonucleotide primers moving the fastest and the larger PCR amplicons moving slower. Once the fragments have moved an appropriate distance, i.e. out of the channel and into the cavity, the electrophoretic charge is reversed, causing the fragments to move in the opposite direction. After a certain amount of time and with a particular charge and voltage the larger molecule will have transferred back into the channel, leaving the smaller primer molecules in the gel material. This is thus a way of effecting purification of the amplicons.

In another embodiment, a third electrode is positioned between the two electrodes shown in FIG. 12. Here electrodes 50 and 51 are set as negative and positive respectively. After a time when the primer molecules have passed the third middle electrode, but the amplicon has not, electrode 50 is reversed to positive charge, leaving electrode 51 as positive. At this point, the third middle electrode is made negative. This causes the primer to continue moving away from the channel, and reverses the direction of the amplicon back towards the channel.

FIG. 13(*a*)-(*g*) illustrates the steps involved using charged dyes in a device. FIG. 13(*a*) shows a modified i-STAT cartridge base of the type described in jointly owned U.S. Pat. No. 5,096,669. It has an entry port 71, a channel 72, a cavity 73 adjacent to the channel and three electrodes 74, 75 and 76, two of which are in the cavity and one in the channel. The cavity contains 1% agarose with buffer as a transparent gel. A sample comprising 5 uL of common electrophoresis loading dyes, bromophenol blue and xylene cyanol, both negatively charged, is added through the entry port and enters the channel as a fluid segment 77, as shown in FIG. 13(*b*). Note that these dyes migrate at roughly 25 to 50 bp sizes, where as with actual DNA separation will be of 50 bp and 300 bp fragment.

In FIG. 13(*c*) a negative potential is applied to 74 and a positive one to 76, in this case 10-50V. The charged dyes quickly move into the agarose gel, towards 76. The two dyes migrate at different rates according to their charge-to-mass ratio through gel. As shown in FIG. 13(*d*) the dyes are resolved into two bands 78 and 79 either side of 75. This takes about three minutes. At this point 74 and 76 were made positive and 75 made negative, thus driving the two migrating dyes in opposite directions as shown in FIG. 13(*e*) until the xylene cyanol dye re-enters the channel, FIG. 13(*f*). Finally, the xylene cyanol is pneumatically moved down the channel for further downstream applications, as shown in FIG. 13(*g*) while the other dye remains in the cavity.

Clearly, the behavior of the two dyes is representative of different length nucleotide sequences or any other chemical species with different charge-to-mass ratios that could be separated from one another quickly using electrophoresis. Furthermore, the electrophoretic properties and capabilities of this device can be tailored according to gel density, buffer-salt selection, applied potential and duration, physical dimensions and the like, to achieve any desired separation.

Figure 24:
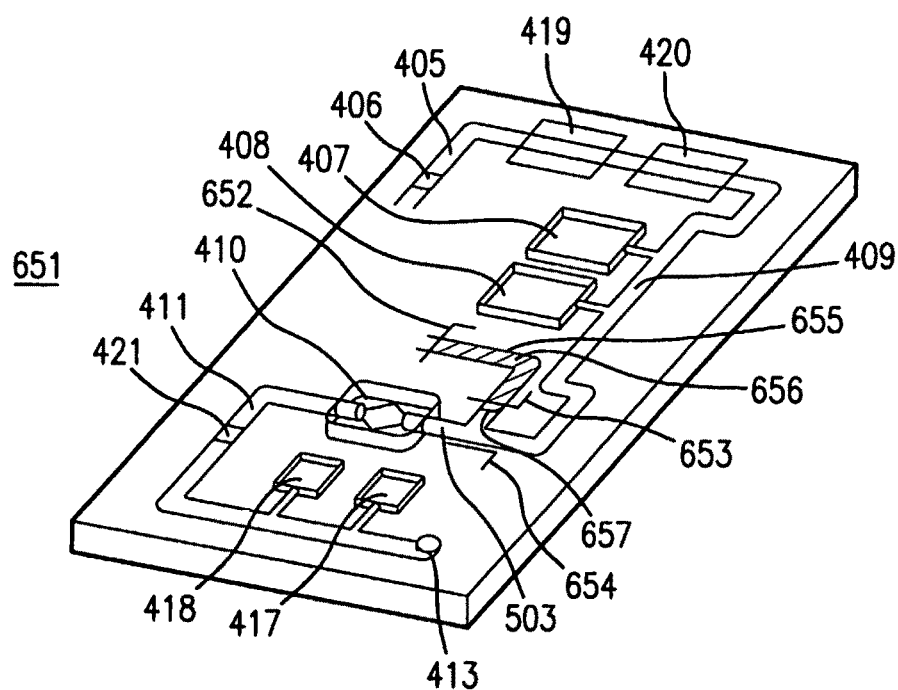
FIG. 24 shows a single-use device with electrophoretic separation of unused primers after amplification.

In another embodiment, the original liquid sample is moved out of the region of the channel abutting the cavity and is replaced with a smaller amount of a different liquid prior to reversing the polarity of the electrodes. This can effect a concentration of the amplicon, which in turn can increase hybridization rates at a later stage in the assay process. In another embodiment, the primers are brought in contact with a capture membrane or particle within the cavity, which effects irreversible binding, thus preventing the primer from moving back towards the channel. In another embodiment, the agarose may be replaced with a different matrix including acrylamide, a mixture of agarose and locust bean gum, hydrocolloids, or other appropriate separation media. In another embodiment, the device is manufactured as a subcomponent on silicon and inserted into a micro-device, as shown in FIG. 12. In another embodiment, to address constraints associated with integration of this separation component into a genetic testing device, the electrophoretic channel may be L-shaped with electrode 75 located at or near the elbow of the 'L.' For example FIG. 24 shows the L-shaped channel feature 655 incorporated into an integrated testing device 651 abutting conduit 409, with electrodes 652, 653 and 654 with entry port 657 and matrix 656. Other elements are as for FIG. 19.

Figure 14:
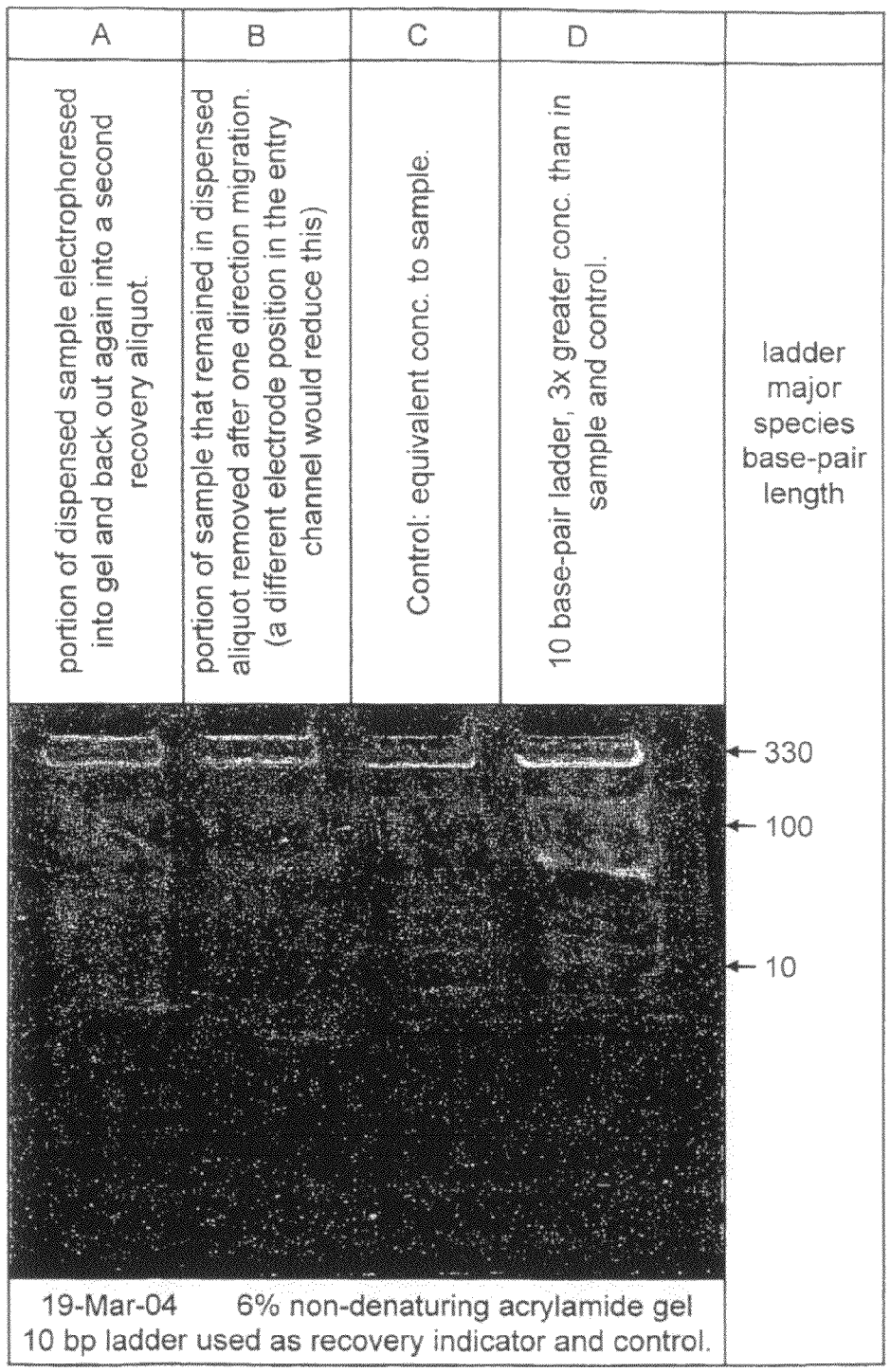
FIG. 14 shows an electrophoretic separation of a primer and an amplicon using a component (as shown in FIG. 13) for integration into a single-use device for nucleic acid testing, confirmed by a second electrophoresis gel.

FIG. 14 demonstrates the operation of the electrophoresis device with an amplicon and primer from a PCR reaction. Lane (A) shows a portion of the PCR reaction product after electrophoresis into gel cavity and back out again and into a fresh second recovery aliquot and applied to a 6% non-denaturing acrylamide gel. Lane (B) shows a portion of sample that remained in original aliquot removed after one direction migration. Lane (C) is a control of equivalent concentration to the sample and lane (D) is a 10 base-pair ladder at a three times greater concentration than in the sample and control. The ladder major species base-pair lengths are 330, 100 and 10.

Clam-Like Oligonucleotides

Figure 15:
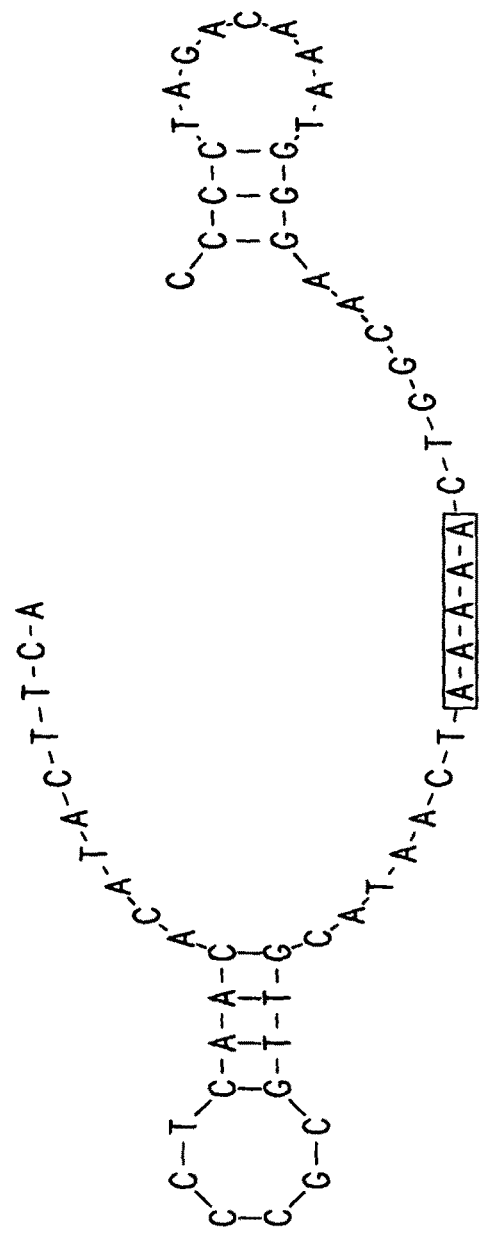
FIG. 15 shows an oligonucleotide primer (SEQ ID NO: 5) lacking CLAM-like features.
Figure 16A:
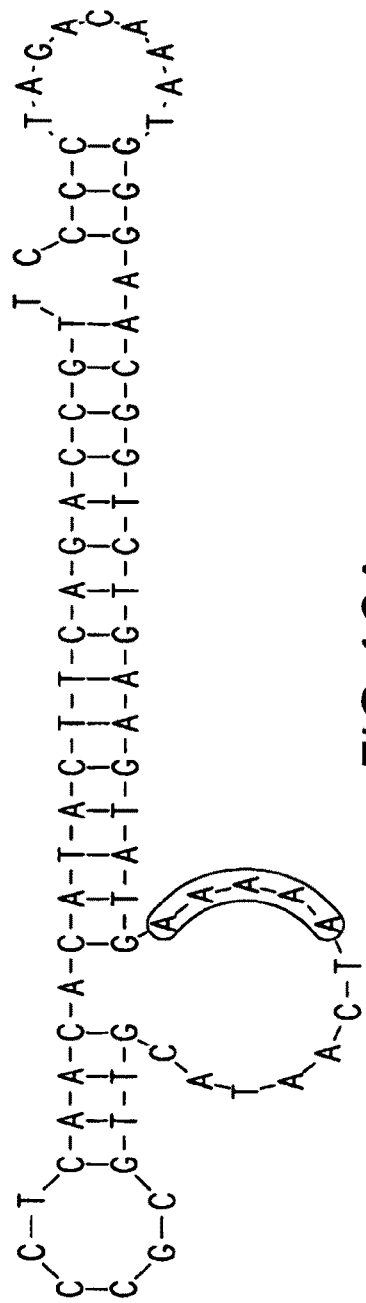
FIG. 16(a) shows the CLAM1 primer (SEQ ID NO: 6)
Figure 16B:
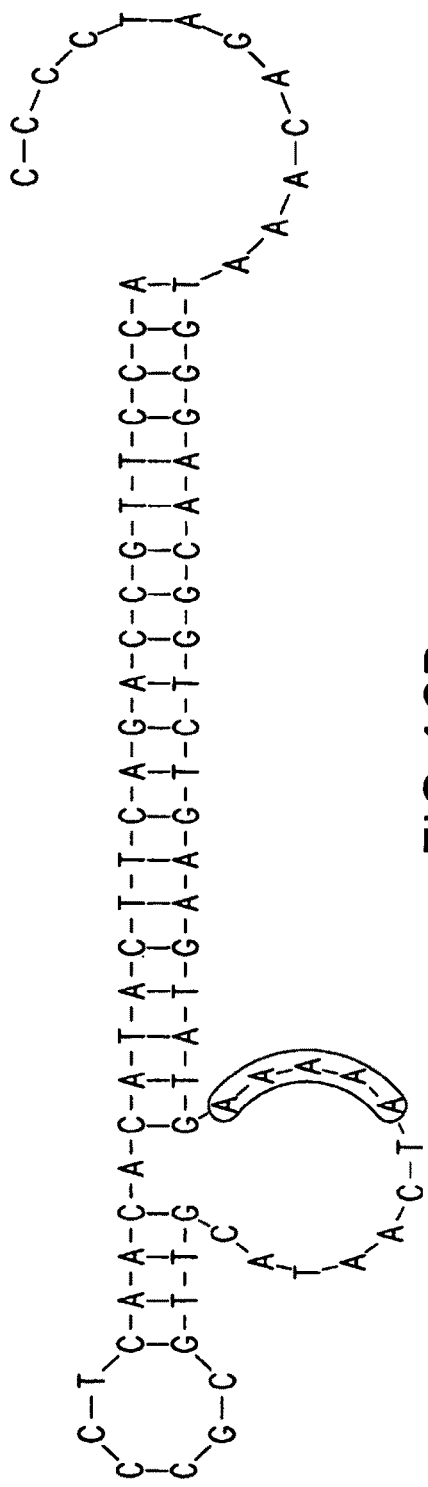
FIG. 16(b) shows the CLAM2 primer (SEQ ID NO: 7).

Normally, for PCR applications reducing the amount of secondary structure is a desirable approach when designing synthetic oligonucleotide sequences, as this helps in reducing non-specific and poor priming of the target. The predicted folding structure of an oligonucleotide that is complementary to the HfeI gene, that has a five base pair adenoside spacer sequence and that has a free single stranded region is shown in FIG. 15. The FIG. 15 sequence is 5'-ACTTCATACA-CAACTCCCGCGTTGCATAAC-TAAAAACTGGCAAGGGTAAA-CAGATCCCC-3' (SEQUENCE ID NO. 5). As a theoretical prediction of potential molecular folding an RNA folding program (Vienna RNA) predicts an oligonucleotide with single stranded nature at any temperature above 10° C. By designing synthetic oligonucleotides with secondary structure at low temperatures, but which lose their secondary structure during the denaturation step of PCR and PCR hybridization, we can effect hybridization of amplicons but not the primer molecules at the later stage of hybridization and detection. Using the isO15 sequence as a starting point, oligonucleotides with a hairpin loop structure were designed and modeled as shown in FIGS. 16(*a*) and (*b*). The base pair sequence in FIG. 16(*a*) is 5'-TTGCCAGACTTCATACACAACTC-CCGCGTTGCATAACTAAAAA-GTATGAAGTCTG-GCAAGGGTAAACAGATCCCC-3' (SEQUENCE ID NO. 6), and that of FIG. 16(*b*) is 5'-ACCCTTGCCAGACTTCAT-ACCCGCGTTGCATAACT-AAAAAGTATGAAGTCTG-GCAAGGGTAAACAGATCCCC-3' (SEQUENCE ID NO. 7).

In the models of FIG. 16, a five base pair sequence shown in the box is used to model the effect of an HPEG spacer. Based on the models in FIG. 16, two oligonucleotides designated CLAM1 and CLAM2 were. The two sequences differ by four nucleotides.

(SEQ ID NO: 14)
CLAM1:
5'-TTGCCAGACTTCATACACAACTCCCGCGTTGCATAACT-HPEG-GTATGAAGTCTGGCAAGGGTAAACAGATCCCC-3'

(SEQ ID NO: 15)
CLAM2:
5'-ACCCTTGCCAGACTTCATACCCGCGTTGCATAACT-HPEG-GTATGAAGTCTGGCAAGGGTAAACAGATCCCC-3'

In the CLAM1 sequence, the sequence located 5' to the HPEG spacer, 5'-TTGCCAGACTTCATACACAACTCCCGCGTTGCATAACT-3' is designated as SEQUENCE ID NO. 8 and the sequence located 3' to the HPEG spacer, 5'-GTATGAAGTCTGGCAAGGGTAAACAGATCCCC-3' is designated as SEQUENCE ID NO. 9.

In the CLAM2 sequence, the sequence located 5' to the HPEG spacer, 5'-ACCCTTGCCAGACTTCATACCCGCGTTGCATAACT-3' is designated as SEQUENCE ID NO. 10 and the sequence located 3' to the HPEG spacer, 5'-GTATGAAGTCTGGCAAGGGTAAACAGATCCCC-3' is designated as SEQUENCE ID NO. 11.

These oligonucleotide sequences maintain the key primary sequence features for Hfe1 priming in PCR reactions and for binding to the capture oligonucleotide, but additional sequences have been added to generate intramolecular binding, generating these "clam-like" structures. Note that the HPEG spacer region sequence is indicated with the five 'A's and it was anticipated that these sequences will have no secondary structure above about 40° to 45° C.

Figure 7C:
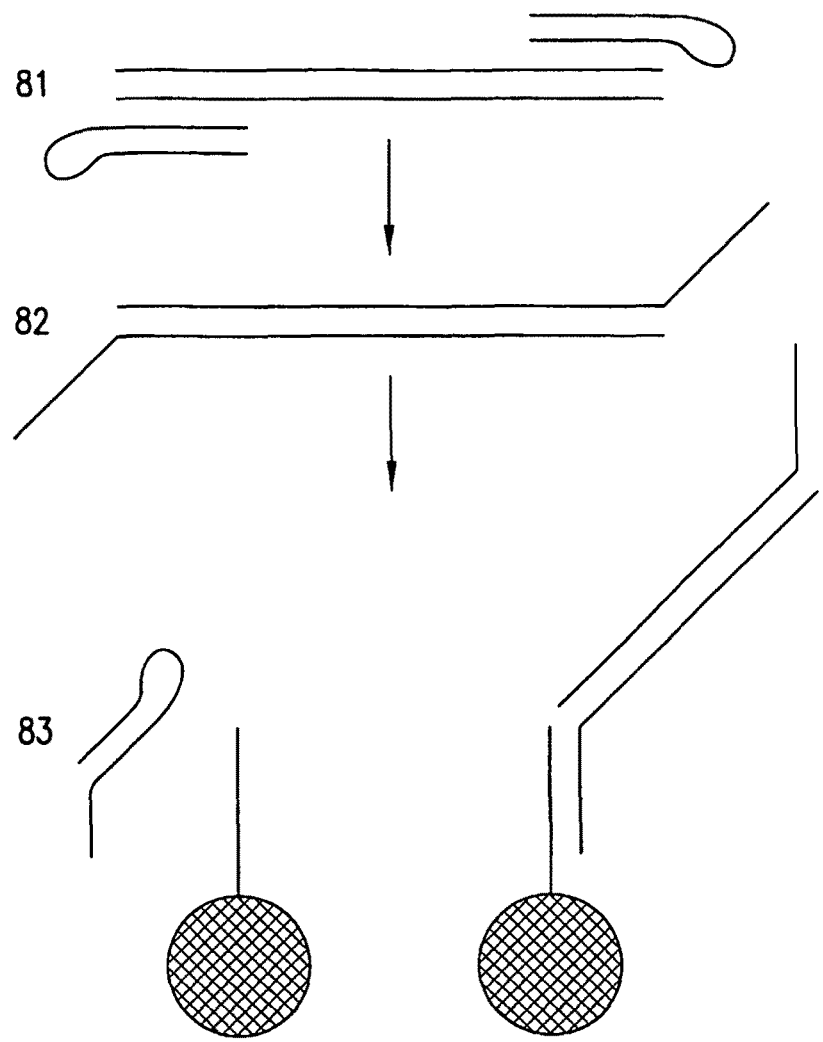

FIGS. 7(b) and 7(c) compare and contrast the differences between using PCR primer sequences with little or no secondary structure and the CLAM PCR primers. At temperatures during PCR, particularly at temperatures at or above hybridization, the CLAM primers do not form secondary structures and once it is incorporated into a PCR amplicon it loses its ability to form a clam structure. At temperatures below PCR hybridization and at temperatures used for hybridization of the capture oligonucleotides, the CLAM PCR primers do form secondary structure. Therefore, unincorporated CLAM PCR primers do not bind to the capture oligonucleotides and do not interfere with signal generation.

FIG. 7(b) shows a PCR reaction using a non-CLAM oligonucleotide sequence and hybridizing to a target nucleotide sequence. A sequence like is015 with no secondary structure is used as one of two PCR primers 81. The PEG spacer generates single stranded regions in the PCR amplicon and excess primer sequences are generated in the reaction 82. In step 83, both the PCR amplicon and the unreacted primer sequences can bind to the capture oligonucleotide bound to a solid substrate like a bead. Typically, the unreacted primer is in significant molar excess compared to the PCR amplicon and reduces the signal detection.

FIG. 7(c) shows a PCR reaction using a CLAM oligonucleotide sequence hybridizing only the PCR amplicon to a target nucleotide sequence. Using a modification to the is015 sequence to generate either CLAM1 or CLAM2 sequences, a PCR reaction is performed 81. At temperatures used in PCR, the secondary structure is eliminated. Once one end of the CLAM oligonucleotide is incorporated into a PCR amplicon it no longer functions with the secondary structure and provides a single stranded region 82. In step 83, the temperature is below that required to generate secondary structure of unincorporated CLAM primer sequences. As a result, CLAM primers that have been incorporated into a PCR amplicon will have single stranded regions capable of binding to the capture oligonucleotide.

Enzymatic Removal

Two enzymatic approaches have been devised for removal of primers, these relate to TdT-tails on unincorporated oligonucleotides and degradation of unincorporated oligonucleotides. Within a PCR reaction mixture there exist two types of structures, amplicons with single stranded regions, in the example above having an iSp18 primer and unincorporated synthetic oligonucleotides. The primers on the amplicons only have extending 5' regions, whereas the unincorporated primers have free 5' and 3' single stranded ends. Using enzymes specific to these differences at the 3' end, strategies to differentially remove these molecules was developed.

Calf Thymus Terminal deoxynucleotidyl transferase (TdT) enzymatic treatment of the PCR reaction product is specific to single stranded 3' extensions, thus only the unincorporated primer will generate a newly incorporated tail. By contrast, the amplicon only has single stranded regions with 5' tails, which are unreactive with TdT.

While it is inefficient and not unique for a universal capture system, one could use a single nucleotide (dNTP) such as 'T' to create an extended T tail at the 3' end of the PCR primer. Any nucleotide, including modified nucleotides, including ribonucleotides could be used for this application and which function with TdT or poly(A) polymerase. The modified PCR reaction mix with T tailed unincorporated primer sequences can then be exposed to a capture oligonucleotide with a poly (A) sequence. Only unincorporated PCR primers with T-tails will be bound to the capture poly(A) sequence. This enriches the reaction mixture for PCR amplicons with associated poly (T) sequences. The poly(A) capture oligonucleotide can be bound to solid surfaces, beads, in a matrix like agarose, acrylamide, poly vinyl alcohol or other appropriate hydrocolloids.

An alternative method is based on the use of an endonuclease. As the unincorporated oligonucleotide primer has a free 3'-hydroxyl group and the amplicon does not, a 3'-5' exonuclease is employed to remove unincorporated oligonucleotide primer. Enzymes including ExoI and ExoT have specific 3'-5' exonuclease activity with single stranded DNA with free 3'-hydroxyl groups. In this embodiment it is preferable to use primers with 5'-phosphate groups.

Post-PCR Hybridization

In the PCR reaction described above, amplicons are generated containing two primers which generate two different single stranded regions. In order to generate a signal, both single stranded regions are necessary, as well as the newly amplified region, which is a bridge between the two single stranded region.

In this example, single stranded A region binds to the complementary A prime capture oligonucleotide at the biosensor. The single stranded B region binds to a synthetic oligonucleotide B-prime which has a moiety for the enzymatic conjugate. Alternatively, the enzymatic conjugate binds directly to the B region.

By first creating a solid substrate with B prime capture oligonucleotides bound to a solid substrate, and in this example in a channel leading to the detection region, and allowing the PCR reaction material to hybridize under the appropriate conditions, any B region oligonucleotides that were not incorporated into amplicons are lost from the channel, enriching the channel for B region oligonucleotides and B region oligonucleotides incorporated into amplicons. Unbound material is washed away.

The enriched bound B region oligonucleotides and amplicons are then released from the solid support by heat or alkaline conditions. The material is allowed to move towards the detection region of the device. Oligonucleotides with A regions or oligonucleotides incorporated into amplicons will be bound to A prime capture oligonucleotides at the biosensor. The biosensor can be washed, removing any unincorporated B primers, leaving only fully incorporated amplicons. This effectively removes background from unincorporated oligonucleotides.

Detailed Description of Nucleic Acid Testing Cartridges

Figure 6:
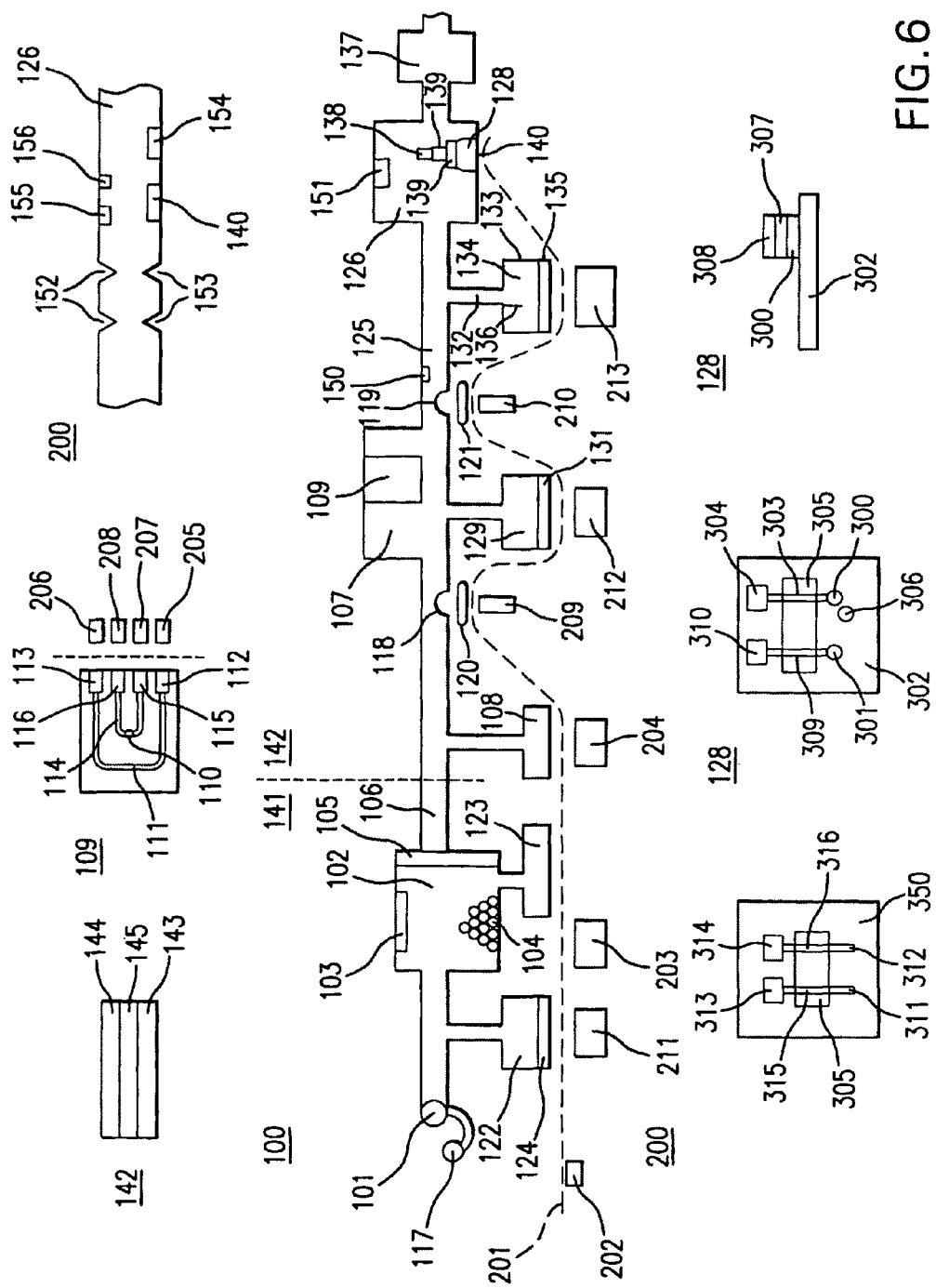
FIG. 6 shows a topological representation of the integrated single-use device and its interaction with the instrument.

An integrated single-use device for performing a nucleic acid analysis and its interaction with the reading instrument is shown topologically in FIG. 6. It comprises a housing 100 with an entry port 101 for accepting a sample suspected of containing a target nucleic acid. The entry port leads to a chamber 102 which has a reagent for extracting said target nucleic acid. The reagent 103 can be coated on to the wall of the chamber. The chamber may contain beads 104, e.g. magnetic beads with a coating suitable for binding nucleic acid. The chamber also preferably contains a wax, which can melt to form a contiguous wax layer 105 in the region of egress to a conduit 106. Once the preferred magnetic beads have associated with said target nucleic acid a magnetic field is applied to draw them through the wax layer and into the conduit. Note that this applied magnetic field may also be oscillated in the chamber to promote extraction of nucleic acid from the sample. Optionally a wash fluid may be applied to the beads prior to leaving the extraction chamber. A wash fluid chamber 122 is connected between the entry port and the extraction chamber. In addition, a sample and wash fluid waste chamber 123 is connected at the distal end of the extraction chamber, with respect to the entry port. In operation, after the extraction step the beads are held on the wall of the chamber by magnetic means and the wash fluid is then passed from chamber 122 through chamber 102 and into chamber 123. This displaces unwanted sample material and leaves chamber 102 containing the beads and predominantly wash fluid. The instrument 200 contains an actuating means 211 which is aligned to chamber 122 and provides a force to a flexible diaphragm 124 to expel the wash fluid out of the chamber.

After washing, the beads then pass through the wax layer and into conduit 106 and then into the amplification chamber 107. Movement of the beads in the conduit is preferably by the same magnetic means, or can be pneumatic. The amplification chamber is also attached to an amplification reagent holding chamber 108, which can deliver these reagents to the amplification chamber with the beads, as in the preferred embodiment, or in a separated step before or after the beads enter this chamber. Alternatively, these reagents may reside in this chamber and element 108 omitted. In another alternative where amplification reagents are best dry-stored, chamber 108 may contain diluents and the reagents coated onto the wall of the amplification chamber.

The amplification reagents as described above can provide for various amplification methodologies, e.g. rolling circle and ligase chain reaction. In the preferred embodiment the reagents incorporate a detectable moiety into an amplified target by means of PCR. Optionally, an applied magnetic field may be used to provide mixing of the beads in the amplification chamber. This is in the same manner as described for the extraction chamber.

The amplification chamber also has a heating element 109 and a temperature sensing thermistor 110 for controlling the temperature of the amplification chamber and thus effecting conditions suitable for amplification of the target nucleic acid. In the preferred embodiment the amplification chamber is cycled between 68° C. and 90° C. for thirty cycles. The time duration at each temperature is more than 5 and less than 30 seconds respectively. While the main part of the housing 100 is made of plastic, at least one wall of the amplification chamber is made of an inert material with superior thermal conduction properties, preferably silicon. The reverse side of the silicon has a resistive path 111 and two electrical contact pads 112 and 113 which constitute the heating element 109. An electric current passing through the resistive path causes heating of the silicon chip and thus the contents of the amplification chamber. The reverse side of the silicon also has a thermistor 110 wired by leads 114 to two electrical contact pads 115 and 116. The output of the thermistor is used by the instrument to control the current passing through the resistive path and thus the temperature of the amplification chamber.

The single-use device 100 may also optionally include closure element 117 to seal the entry port. This can be a plastic snap-closure element of the type described in jointly owned U.S. Pat. No. 5,096,669 or the slide closure of jointly owned pending U.S. application Ser. No. 10/658,528.

The amplification chamber may also be sealed at the ingress and egress by 118 and 119 respectively. This is desirable for ensuring reagents remain in the chamber during temperature cycling. For example, element 118 and 119 may be deformable rubber seals. Actuation can be by pin elements 209 and 210 in the instrument, which move through opening 120 and 121 in the housing to contact 118 and 119 and cause sealing. Pin elements 209 and 210 may be actuated independently or together by the instrument.

The egress of the amplification chamber is attached to a second conduit 125 containing a sensing region 126 comprising an immobilized capture oligonucleotide 127 and a sensor 128. The housing 100 contains a second pump means 129 attached to the amplification chamber for moving the amplified target to said sensing region. The pump means comprising an air-filled chamber 130 with a diaphragm 131. The instrument 200 contains an actuating means 212 for applying a force to element 131 to pneumatically displace air from chamber 130 and thus displace the amplified target towards the sensing region.

When the amplified target arrives in the detector region it can bind to the capture oligonucleotide and be retained. The detection region also contains a dry reagent layer coated onto the wall 151. In the preferred embodiment, the moiety associated with the primer (which becomes part of the amplicon) is biotin and the dry reagent 151 is streptavidin-labeled alkaline phosphatase. Dissolution of the reagent with the amplicon causes it to bind to the biotin via the well known biotin-avidin interaction. In operation this step generally takes from about 5 to about 15 minutes. In alternative embodiments the moiety can be 5' FAM or 5'-biotin and the dry reagent anti-FITC-ALP (alkaline phosphatase) or streptavidin-glucose oxidase conjugate.

A third conduit 132 is attached to the second conduit 125 between the egress of the amplification chamber and the sensing region. It has a chamber 133 with a detection reagent 134. Optionally, the reagent is contained in a flexible sealed foil pouch 135 and in operation the instrument contains an actuating means 213 which can provide force to the pouch and cause it to rupture by being pressed against a rupturing feature 136, preferably a sharp plastic point molded into the housing. This caused the detection reagent to move out through the third conduit and into the second conduit. This displaces and washes away any uncaptured amplified target and other material from the sensing region while permitting amplified target to remain bound to the capture oligonucleotide. The housing 200 also contains a waste chamber 137 attached to the second conduit for receiving the displaced material.

In the final step, the detection reagent reacts with the moiety 138 incorporated into said amplified target 139 to generate a signal at the sensor 140. In the preferred embodiment where the moiety is biotin and is bound to streptavidin-labeled alkaline phosphatase, the detection reagent is p-aminophenol phosphate which is hydrolysed to form p-aminophenol by the enzyme. This is then electrochemically oxidized at the electrode surface of an amperometric sensor to generate a current proportional to the amount of moiety that is present, as illustrated in figures showing chronoamperometry (current versus time plots).

Figure 21A:
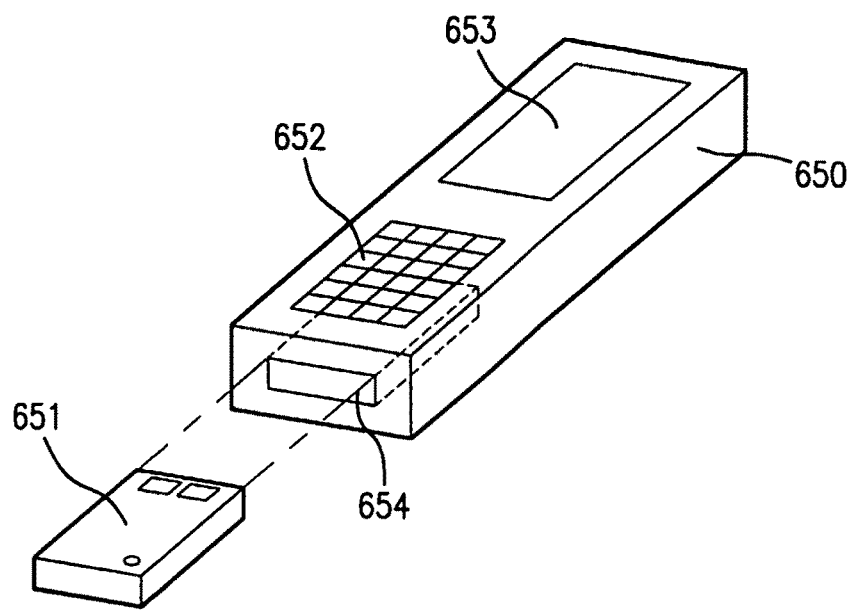
FIG. 21(a) shows a cartridge and instrument separately and FIG. 21(b) shows the cartridge inserted into the instrument.
Figure 21B:
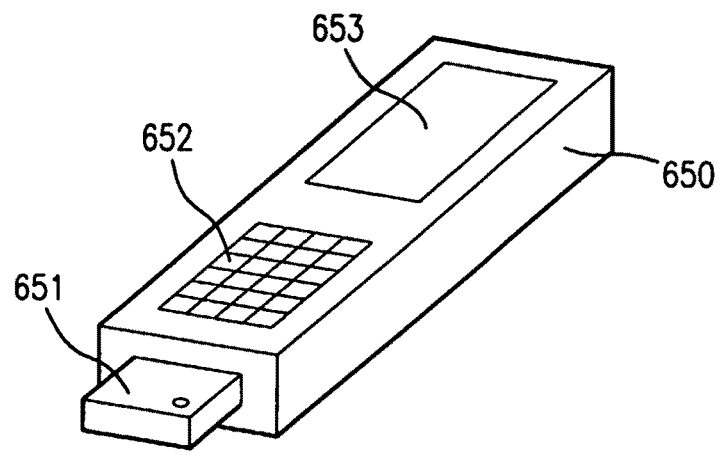

The instrument, 200 in FIGS. 6 and 650 in FIG. 21, used to operate the integrated single-use device is shown interacting with the test device in FIG. 21. It includes a port 654 for receiving the single-use device 100 and 651. The instrument has a keypad 652 for user entries and a display 653. One or more locating features 202 for locating the device with respect to the instrument to provide for the desired interaction of electrical connecting elements and actuating elements are provided. The instrument contains an electromagnet 203 adjacent to the location of the beads 104 in chamber 103. The electromagnet may be used to move the beads from the extraction chamber to the amplification chamber and to promote mixing of the beads within each chamber. The instrument includes an actuating means 204 adjacent to the location of the amplification reagent holding chamber 108 which can provide pressure to the chamber and cause the reagent to be displaced into the amplification chamber. The instrument also has a pair of electrical contacts 205 and 206 for contacting element 112 and 113 and a power source for passing a current through 111. It also includes a pair of electrical contacts 207 and 208 for contacting element 115 and 116 for contacting the thermistor 110. Furthermore, the instrument includes suitable electrical circuitry and an embedded algorithm for controlling the temperature of the amplification chamber through these means.

The instrument includes actuation pin elements 209 and 210, which move through opening 120 and 121 in the housing to contact and close 118 and 119 to seal the amplification chamber. Suitable electromechanical features are included to effect this actuation along with a controlling algorithm for initiating sealing at the appropriate step in the analysis cycle.

The instrument also has an electrical connector of the type described in jointly owned U.S. Pat. No. 4,954,087 and U.S. Pat. No. 5,096,669. It is used to make electrical connection to the sensor 128 in the housing 100. Where it is desirable to perform the detection step at a controlled temperature, e.g. 37° C., the connector also incorporates heating and thermistor elements, which contact the back side of the silicon chip that provides the substrate for the sensor. These elements are of the same type as described for the amplification chamber. The instrument has amperometric circuitry for controlling the potential of the sensor and measuring current. The instrument also has an embedded algorithm for controlling the entire analysis sequence performed by the instrument on the single-use device to make a nucleic acid determination and display a result on a display screen on the instrument. Where the electroactive species generated or consumed in proportion to the captured target is more appropriately detected by means of potentiometry or conductimetry, alternative circuitry well known in the art is incorporated into the instrument.

Figure 19:
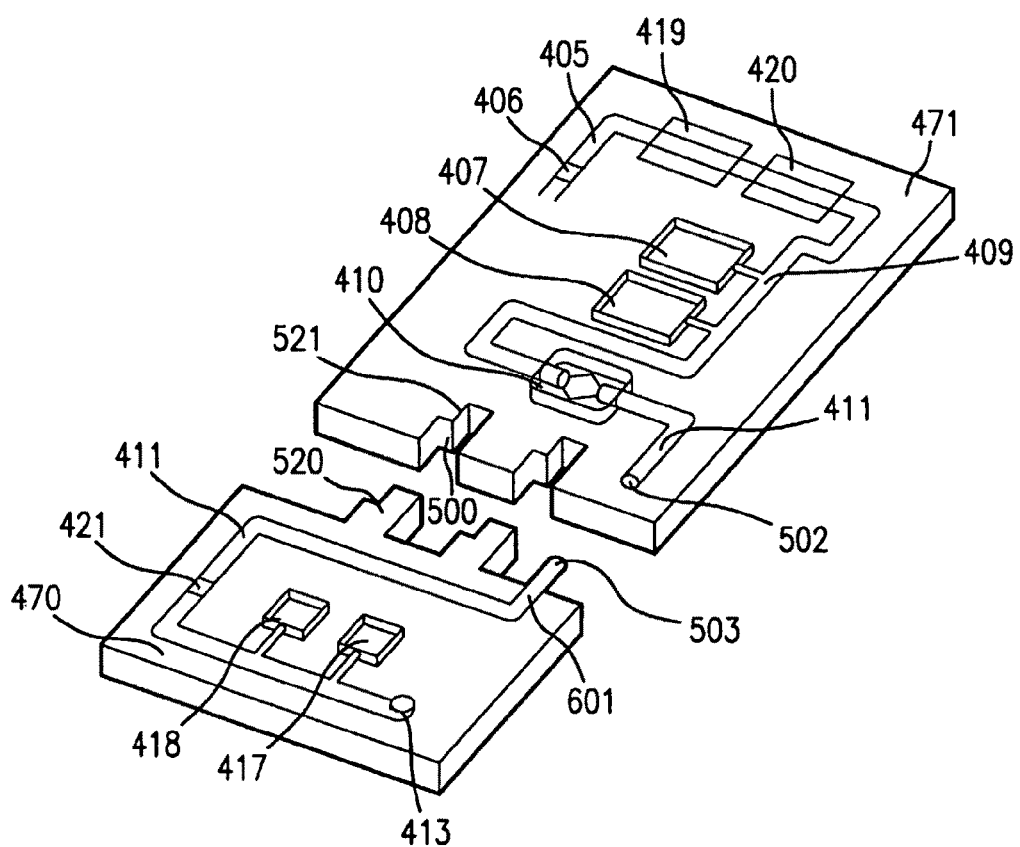
FIG. 19 shows a two-part cartridge with a separate extraction component that can mate with the amplification and detection component.
Figure 20:
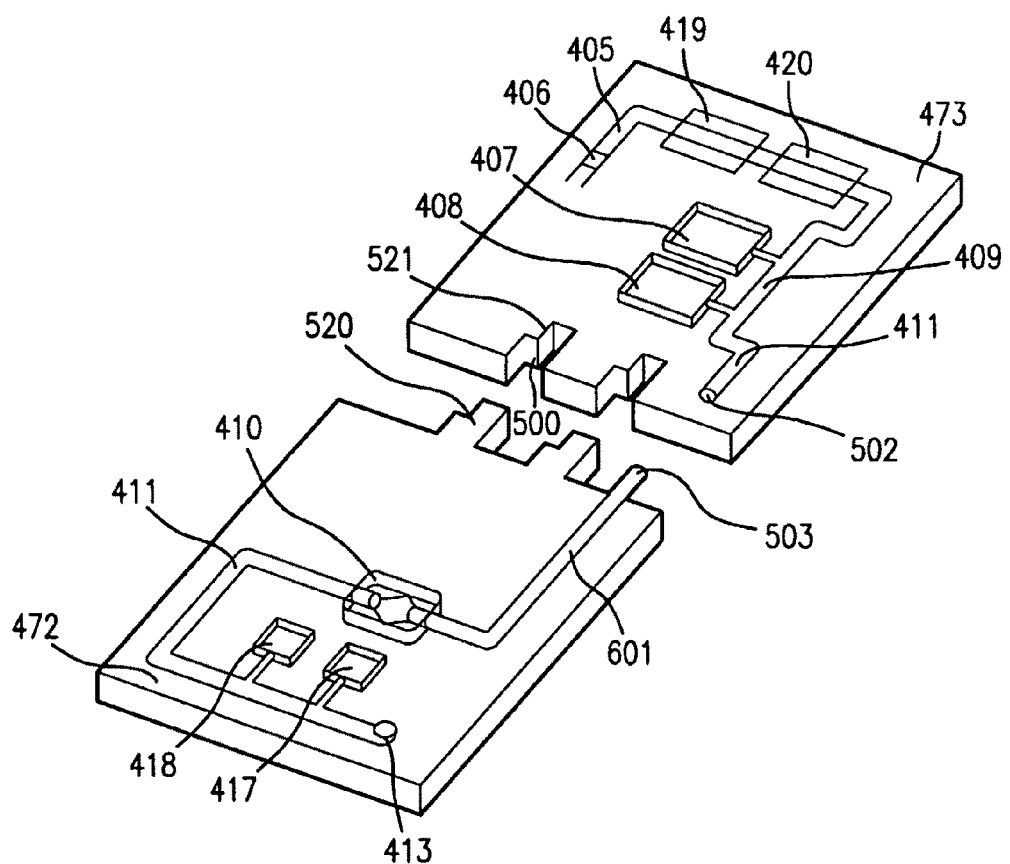
FIG. 20 shows a two-part cartridge with a separate detection component that can mate with the extraction and amplification component.

In an alternative embodiment, the single-use device is composed of two separate parts as shown in FIGS. 19 and 20. FIG. 19 illustrates a separate extraction device 470 and a combined amplification and detection device 471. The elements in a combined form have the same features as those shown for the integrated device in FIG. 6, with the exception of features related to transferring extracted material from one to the other. Element 470 comprises an entry port 413, conduit 411, wash fluid 417 and waste chambers 418, a separation region 421, a terminal portion of the conduit 601 and an egress port 502 which mates with ingress port 502. It also has mating features 520 and 521 which match one or more opening 500 in 471. Element 471 has an amplification chamber 410, conduit 409, chambers 408, 409 and sensors 419, 420, exit conduit 405 and sealing feature 406. FIG. 20 is similar to FIG. 19, with the difference that it comprises a combined extraction and amplification component 472 and a separated detection component 473. The mating features are appropriately located between the two.

Figure 17A:
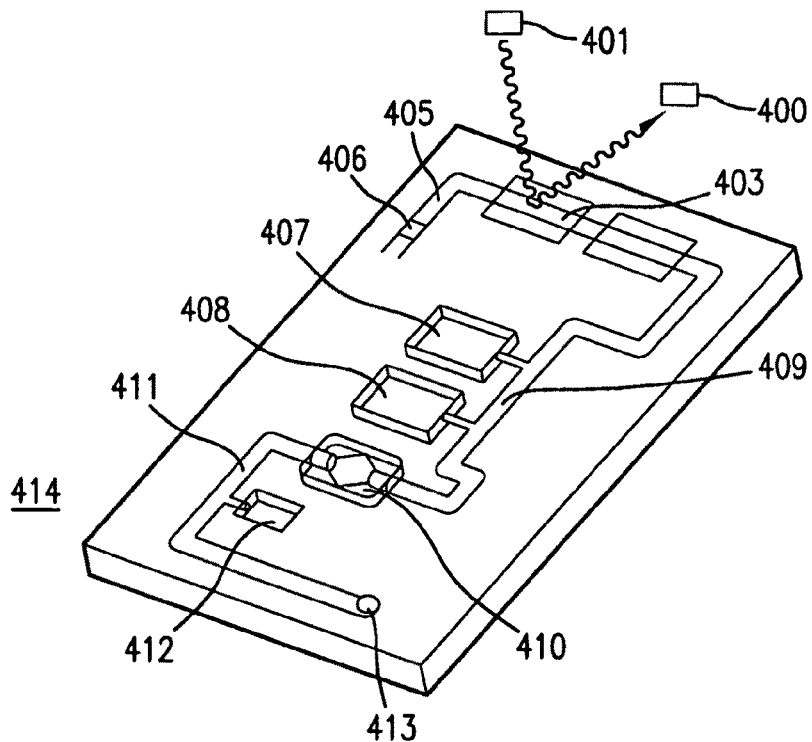
FIG. 17(a) shows an optical detection-based single-use cartridge where an optical sensor is integrated into the device and FIG. 17(b) shows an optical single-use cartridge where the sensing region is a cuvette feature permitting detection with a light source and detector integrated into the instrument.
Figure 17B:
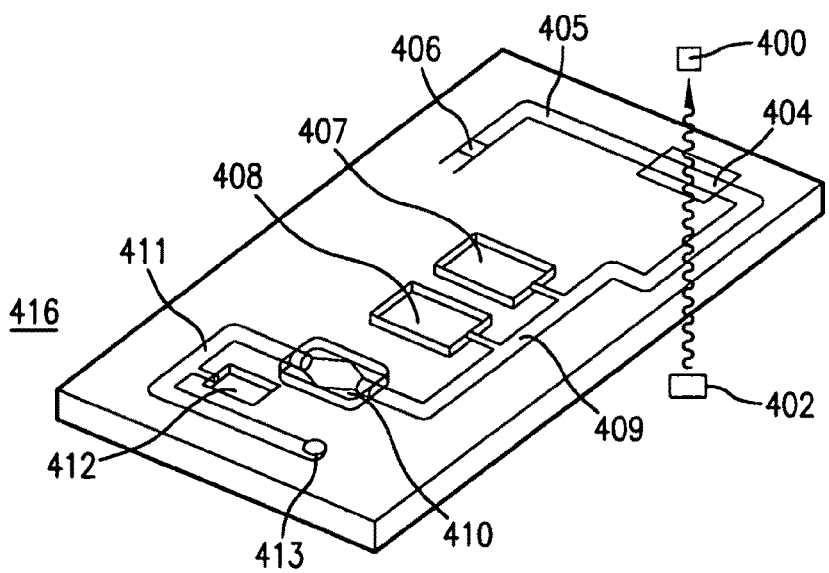
Figure 18:
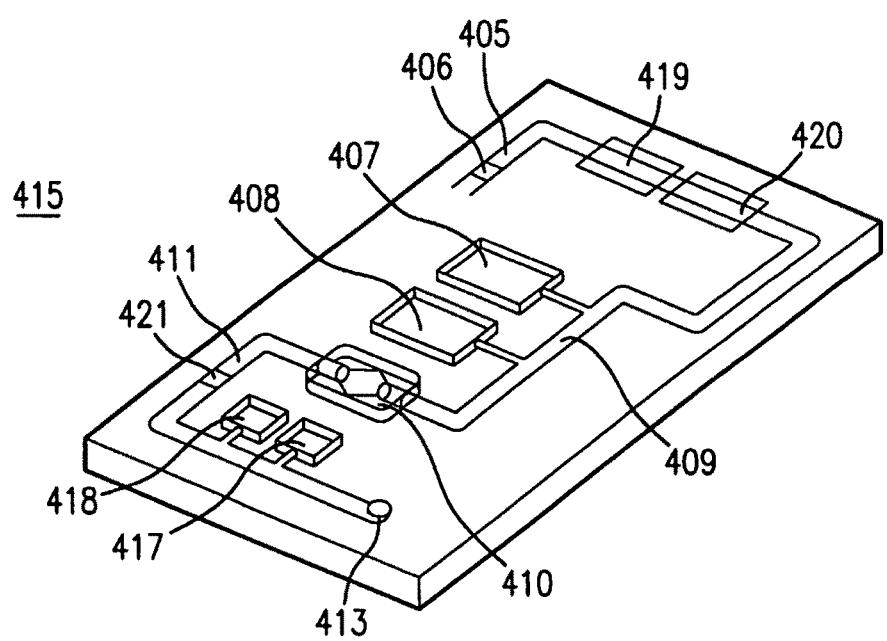
FIG. 18 shows an extraction device containing a filter region integrated into a single use cartridge for nucleic acid testing.

FIG. 18 shows an additional embodiment where a filter region 421 is integrated into a device that performs extraction, amplification and detection. Other elements are as for FIG. 19. FIG. 17(*a*) shows an optical detection-based single-use cartridge where an optical sensor is integrated into the device that is interrogated by a reflectance method. Light is generated by element 401 and interacts with sensor 403 and is captured by detector 400. FIG. 17(*b*) shows an optical single-use cartridge where the sensing region is a cuvette feature 404, permitting detection with a light source 402 and detector 400 integrated into the instrument.

Figure 28B:
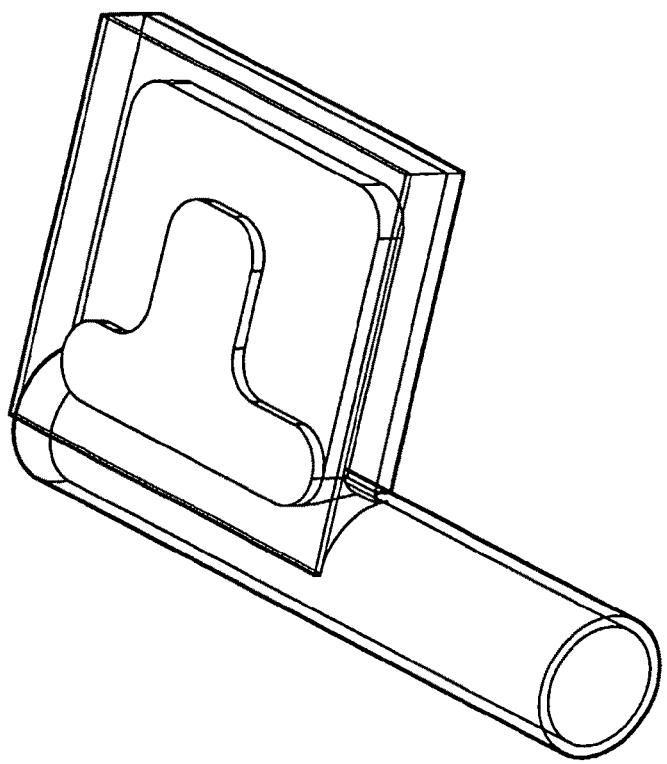
FIG. 28(a)-(b) show two views of a buccal sample device for direct application of a buccal sample to a PCR chamber. This extraction and amplification device attaches to the detection cartridge.
Figure 28A:
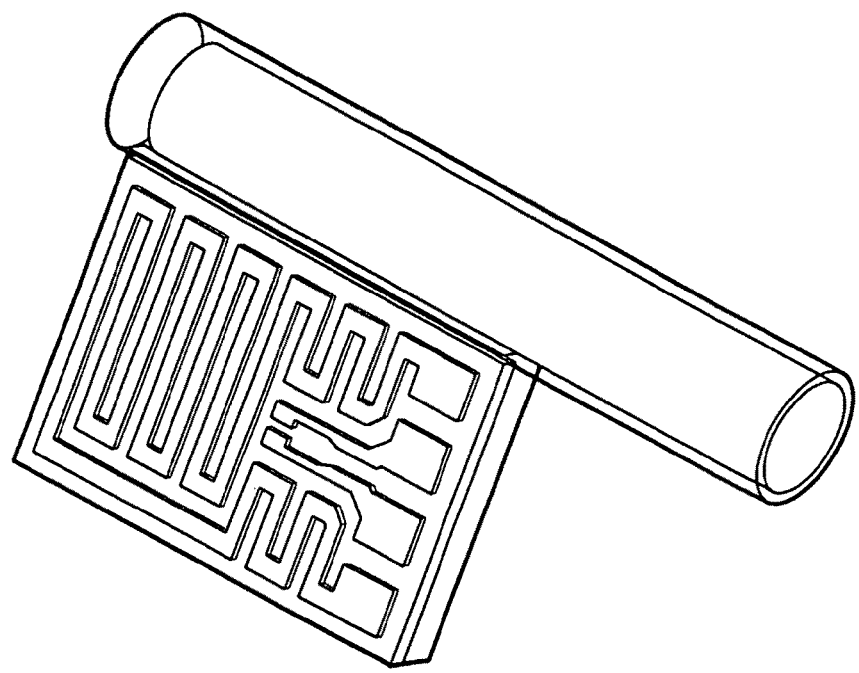
Figure 29A:
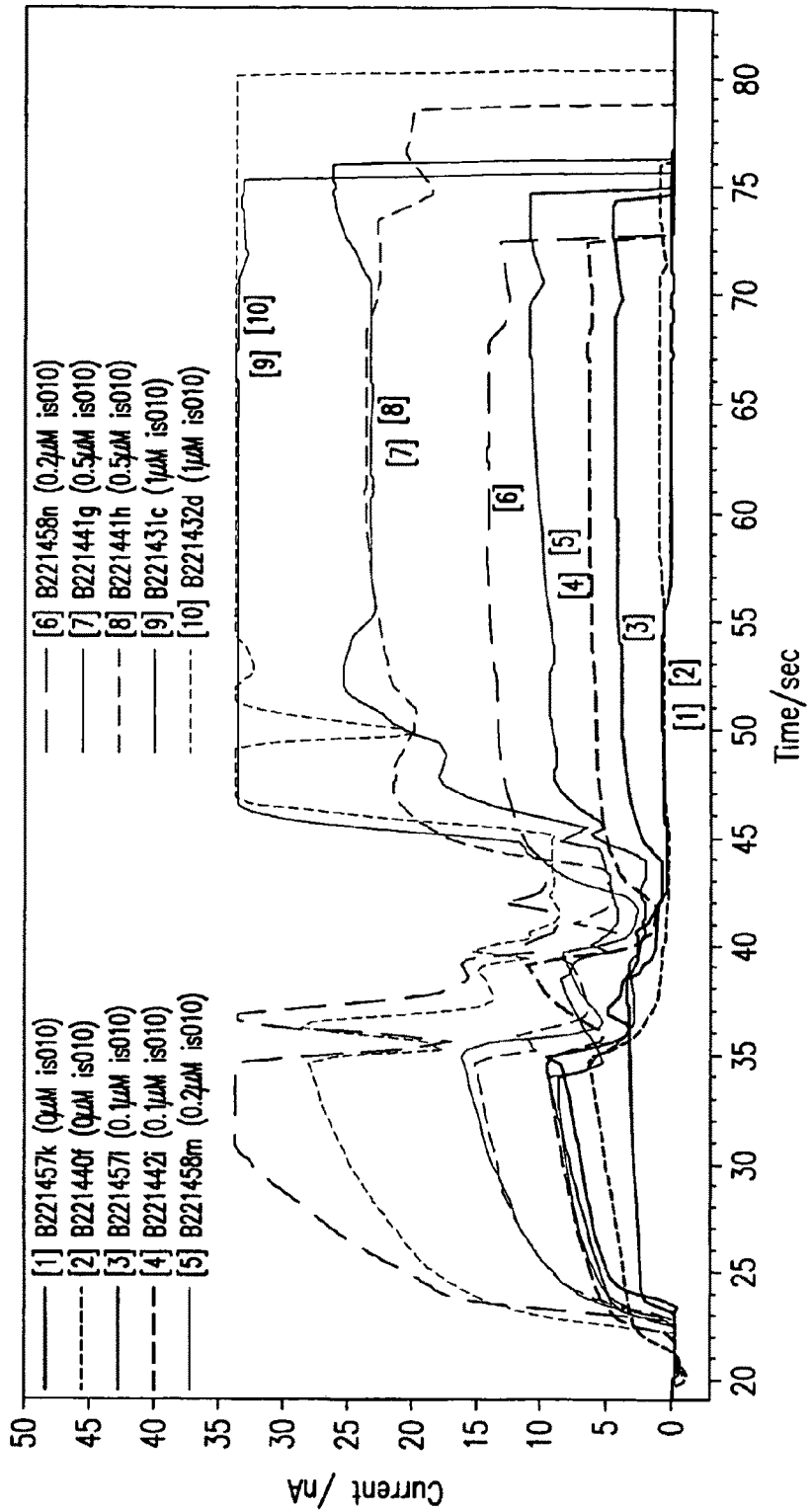
FIG. 29(a)-(b) show a comparison of signal which increases relative to the amount of control oligonucleotide.
Figure 29B:
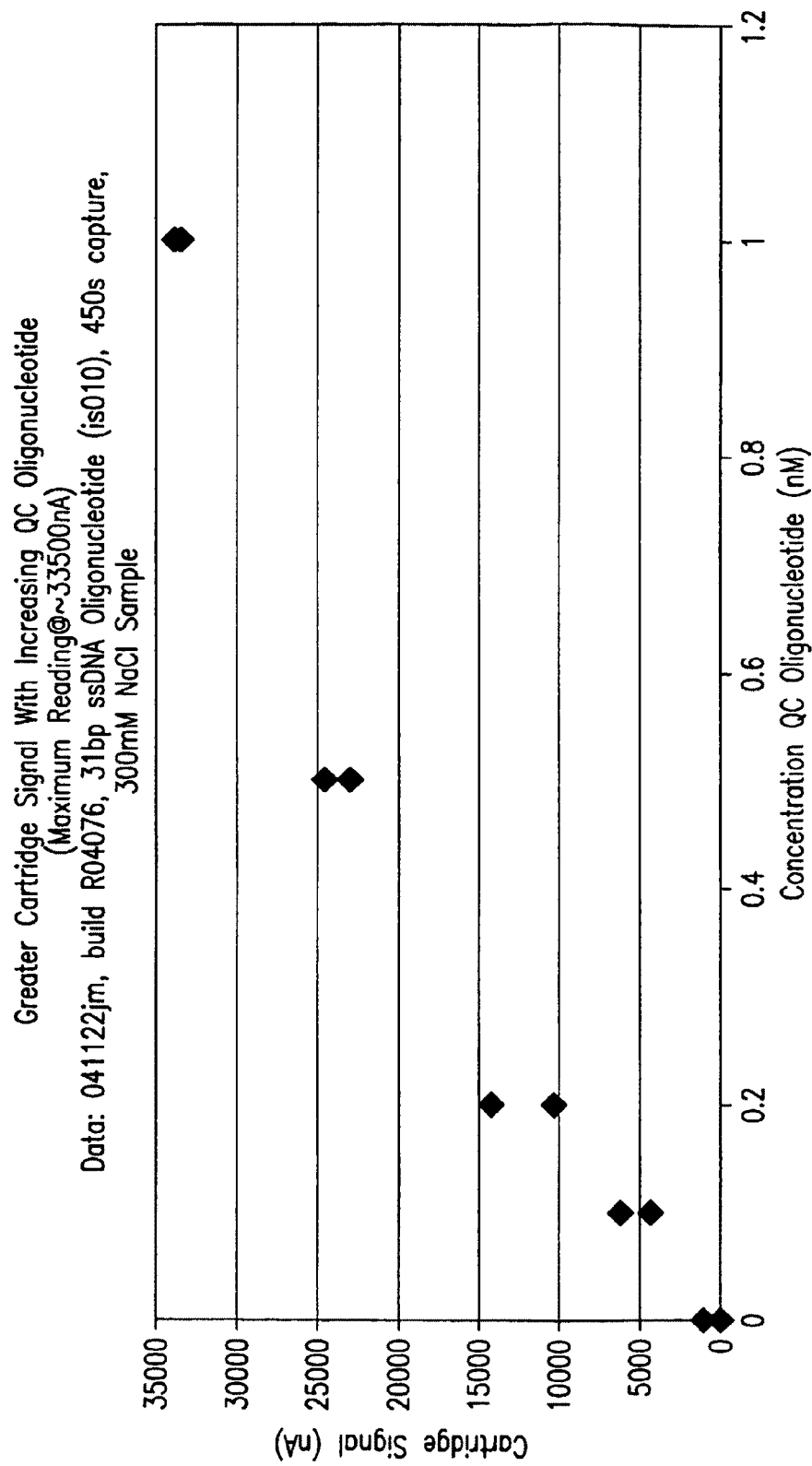
Figure 30A:
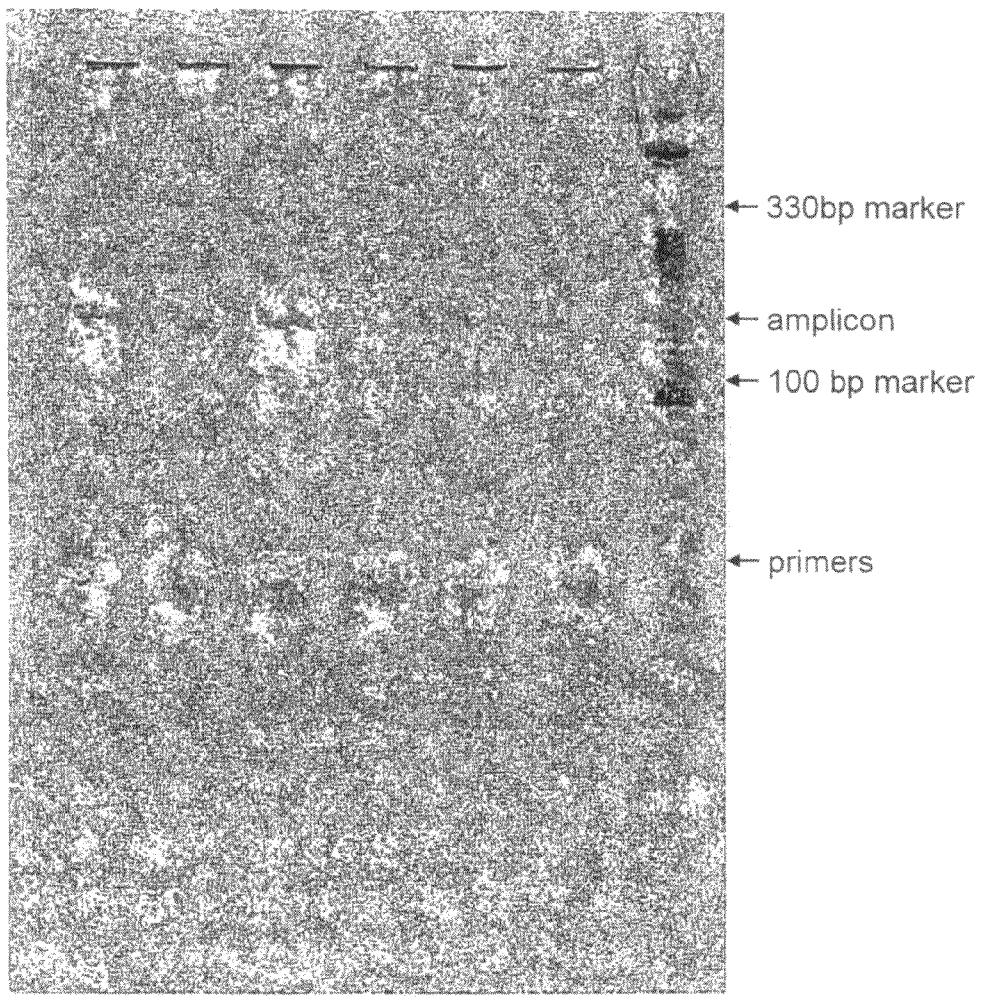
FIG. 30(a)-(b) show the ability of the cartridge to discriminate between wild-type and mutant SNP sequences of hemachromatosis.
Figure 30B:
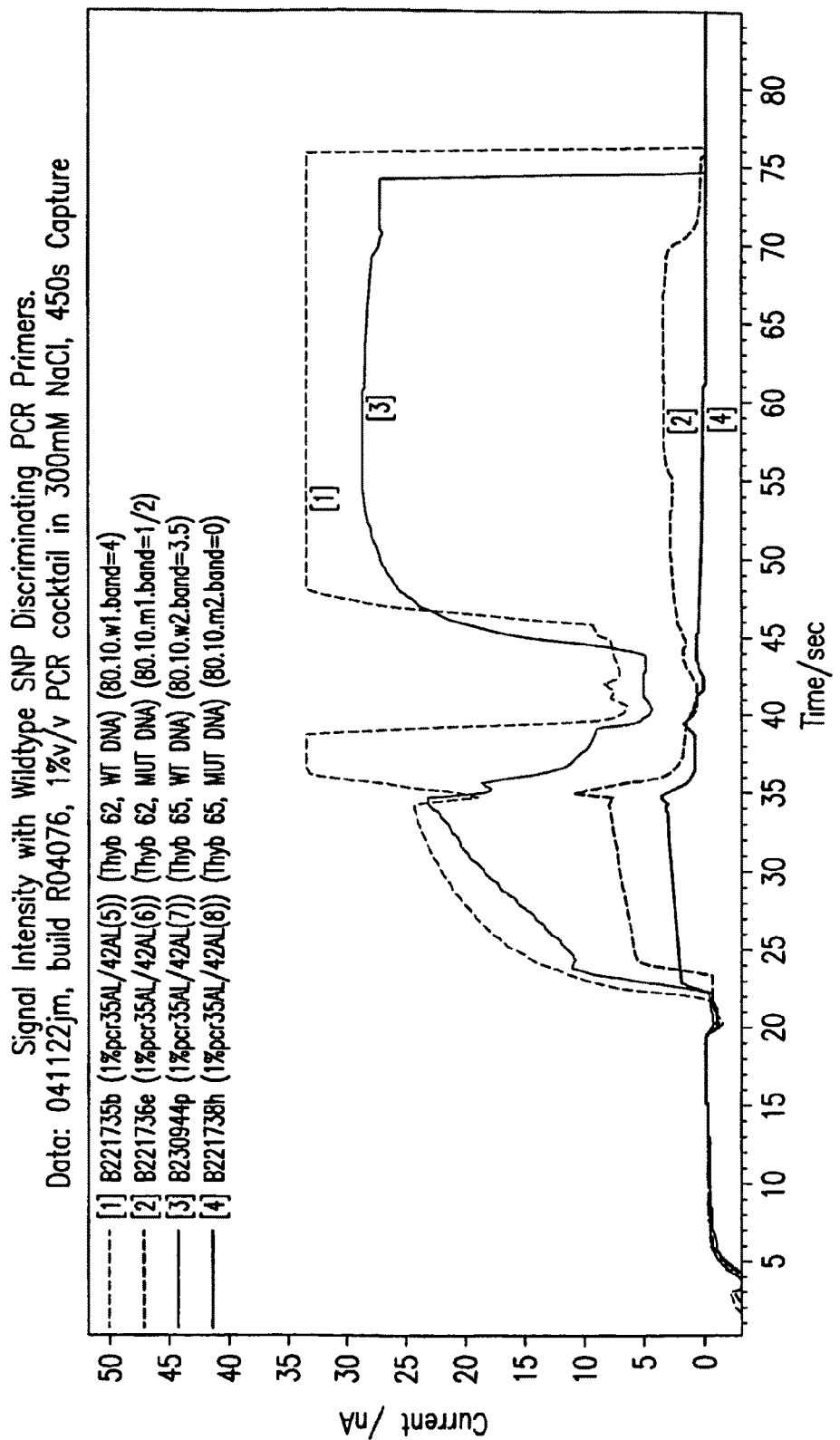

It has been found that where the sample is a buccal swab, the extraction component element, either magnetic or filter based, is unnecessary and the sample may be directly inserted into the amplification chamber. FIG. 28(*a*) and FIG. 28(*b*) show two views (top and bottom) of a buccal sample device for direct application of a buccal sample to a PCR chamber. This extraction and amplification device attaches to the detection cartridge, by means of the mating features described above (not shown).

The general dimensions of the housing 100 are about 6 cm in length, 3 cm in width and 0.3 cm in height. The conduits and other features are preferably rendered in a device base 143 and a device cover 144 which are held together by an intervening double-sided adhesive tape 145, see FIG. 6. Where the base and cover are injection molded in plastic, typically ABS or polycarbonate, conduits and recesses to accommodate silicon chips, fluid containing pouched and the like are molded features. In this embodiment the adhesive tape acts as a sealing gasket to confine liquids to the desired conduits and chambers. Detailed discussion of the use of molded cover and base elements along with the use of adhesive tape gaskets is found in jointly owned U.S. Pat. No. 5,096,669 and pending US 20030170881 which are incorporated here by reference.

Detailed Description of Detection

The preferred method of detection in the single-use cartridge is electrochemical, however other sensing methods including fluorescence, luminescence, colorimetric, thermometric, fiber optics, optical wave guides, surface acoustic wave, evanescent wave, plasmon resonance and the like can be used.

The preferred sensor 128 comprises an amperometric electrode 300, which is operated with a counter-reference electrode 301 and is shown in FIG. 6. The amperometric electrode 300 comprises a 100 um diameter gold layer microfabricated onto a silicon chip 302. The silicon chip is treated in the first step of manufacture to produce an insulating layer of silicon dioxide on the surface, as is well known in the art. The electrode is connected by means of a conducting line 303 to a connector pad 304 which makes contact with the electrical connector of the instrument. The conducting line is typically coated with an insulating layer of polyimide 305. Directly over the electrode 300 or at an adjacent location 306 on the chip are adhered polymer particles 307 that have a ligand 308 complimentary to and capable of capturing the amplified target. The counter-reference electrode may be microfabricated on the same silicon chip or one place adjacently in the second conduit 125. It comprises a silver-silver chloride layer, of 200 um diameter attached by a contact line 309 to a contact pad 310 that makes contact with the instrument connector. Again the line 309 is preferably coated with an insulating layer of polyimide. A detailed description of amperometric sensor microfabrication is found in jointly owned U.S. Pat. No. 5,200,051 which is incorporated here by reference.

A conductivity sensor comprising two conductive bars 311 and 312 are present on chip 302, or an adjacent chip 350, connected to contact pads 313 and 314 by lines 315 and 316 respectively, see FIG. 6. The conductivity sensor can be used by the instrument to distinguish if liquid or air is in contact with the sensor and thus determine the position of a solution in the second conduit with respect to the sensor 300. This solution may be one containing the amplified target or the detection reagent. Optionally a conductivity sensor may be incorporated into or adjacent to both the extraction chamber and the amplification chamber to determine the position of a fluid. A detailed description of conductivity sensor microfabrication and use is found in jointly owned U.S. Pat. No. 5,447,440 and U.S. Pat. No. 6,750,053 which are incorporated here by reference.

In an alternative embodiment of the single-use device 100 a transparent glass window is substituted for the silicon chip 302 and the sensing region of the device forms a cuvette, FIG. 17. The amplified target capture reagent is immobilized on the glass and in this case the detection reagent contains a molecule that the moiety, e.g. alkaline phosphatase, causes to generate an optically detectable signal, e.g. fluorescence. Such molecules are well known in the art. In all other respects the operation of the single-use device is the same as in the electrochemical detection mode.

Detailed Description of Nucleic Acid Testing Cycle with Single-Use Device

Figure 23:
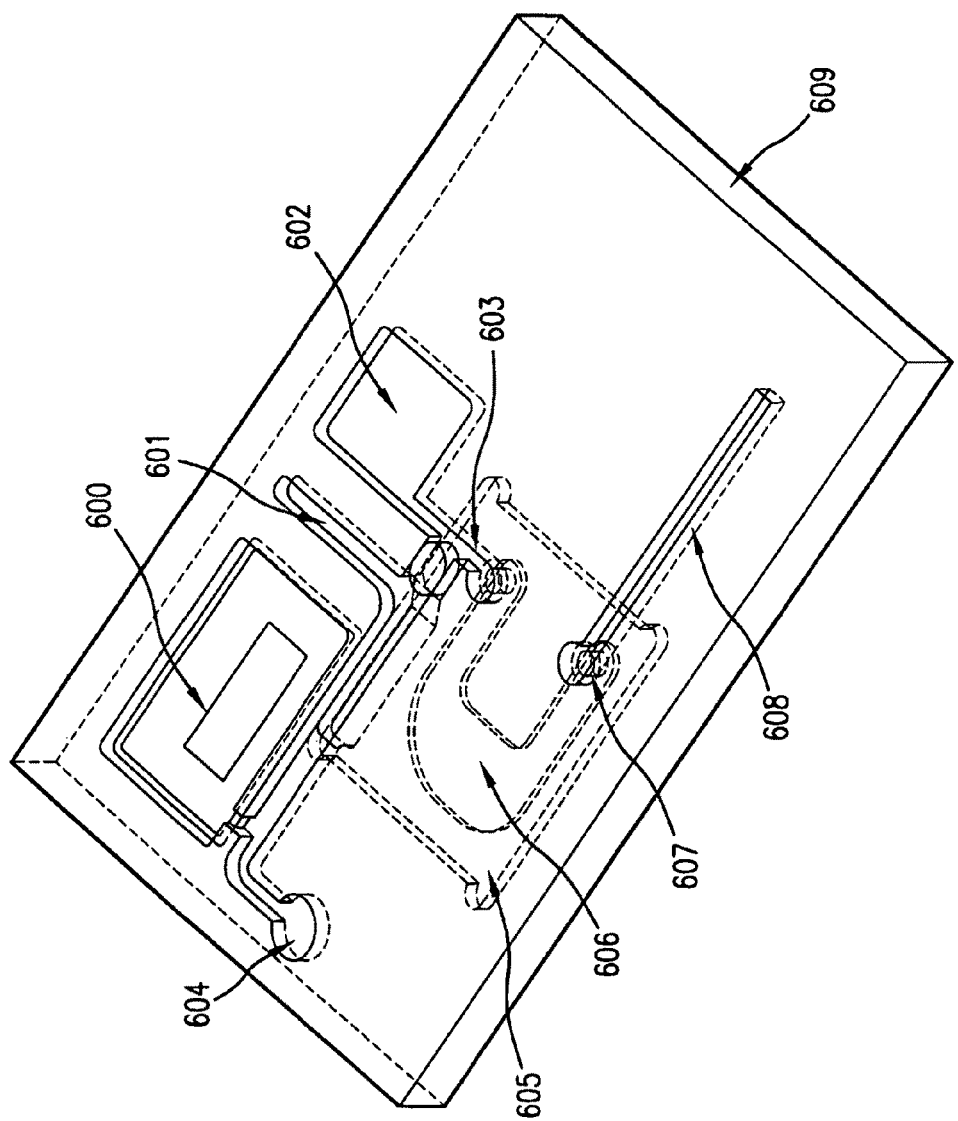
FIG. 23 shows an extraction and amplification component where a silicon chip provides one of the walls forming the extraction and amplification chambers.

The preferred embodiment of an assay cycle using the single-use device 100 in conjunction with the instrument 200 is as follows. An approximately 10 uL blood sample is added to the entry port 101 and is drawn by capillary action into the extraction, chamber 102. An entry port closure element 117 is then used to seal the entry port. Reagents 103 comprising a chaotropic agent, lithium dodecylsulfate and dithiothreitol and a chelating agent, ethylene diamine tetraacetic acid, which are coated on the wall of the chamber dissolve into the blood sample and cause lysis of the cells and permit nucleic acid from within the cells to be liberated and to be adsorbed onto the carboxylate coating on the magnetic beads 104. A magnetic field can be used to agitate the beads to promote mixing within the chamber and speed up the rate of extraction. This step of the extraction process generally takes about 0.3 to less than 1 minute. Where the magnetic field is deployed, this is under the automatic control of the instrument and is determined by an embedded algorithm that controls the test cycle. Once this step is complete, the instrument deploys a magnetic field which holds the magnetic particles to the side of the extraction chamber. Wash fluid from the wash fluid chamber 122 is then pneumatically forced into the extraction chamber and flushes the contents into the wash fluid waste chamber 123. Note that the wash fluid waste chamber has a vent 146 and that during this step the instrument seals the ingress 118 to the amplification chamber, thus waste fluid is directed into the waste chamber rather than entering conduit 106. This step takes about 30 seconds. The wash fluid in the preferred embodiment is deionized water and the volume of wash fluid that passes through the extraction chamber is 20 to 30 uL. Note also that the silicon chip that forms one wall of the amplification chamber also forms one wall of the extraction chamber, as shown in FIG. 23, thus the extraction process can be performed at a controlled temperature. In the preferred embodiment nucleic acid extraction from blood occurs at room temperature.

In the next step, the instrument opens the ingress seal 118 and releases the magnetic particles from the wall of the extraction chamber and draws them through the wax layer at the boundary of the extraction chamber and conduit leading to the amplification chamber. The instrument ensures that the temperature of the extraction chamber is sufficient for the wax to be in liquid form and permit the magnetic particles to pass through. In the preferred embodiment the wax is paraffin and the controlled temperature is at between 45 to 70° C. As discussed previously passage of the particles through the wax minimizes interferents of PCR amplification, which can include hemoglobin. The particles are then drawn into the amplification chamber. In the preferred embodiment the amplification chamber has a volume of 10 to 20 uL. As shown in FIG. 23 the chamber 606 is "U" shaped having a total length of 8 mm, width of 8 mm and height of 0.25 mm. Other features of the element 609 shown in FIG. 23 are chambers 600 and 602, ports 603, 604 and 607, conduits 601 and 608, and heater 605.

The next step of the process involves the instrument pneumatically displacing the PCR amplification reagent from its chamber into the amplification chamber. The PCR amplification reagents comprise DNA polymerase, a buffer and a modified primer. The primer comprises a sequence of bases complimentary to a first region of the target nucleic acid, a polymerase blocking region, a single stranded hybridization region attached to the polymerase blocking region with an attached detectable moiety, which is biotin. In the preferred embodiment the buffer consists of 22 U/ml *Thermococcus* species KOD thermostable polymerase complexed with anti-KOD antibodies, 66 mM Tris-SO4 (pH 8.4), 30.8 mM (NH4)2SO4, 11 mM KCl, 1.1 mM MgSO4, 330 uM dNTPs, as well as proteins and stabilizers (Invitrogen Life Technologies AccuPrime Pfx SuperMix manual, Cat. No. 12344-040), but alternatively could be 20 mM Tris-HCL (pH 8.8), 2 mM MgSO4, 10 mM KCl, 10 mM (NH4)2SO4, 0.1% Triton-X-100, 0.1 mg/ml nuclease-free BSA as described in the Stratagen Pfu DNA polymerase Instruction Manual Cat#600135 Revision$ 064003d).

In the net step the instrument seals the two sealing elements in the device, 118 and 119, to retain the beads and reagent in the amplification chamber and the cycles the temperature thirty times between 95° C. and 99° C., and a hybridization step at 68 C with durations at each temperature of 2 seconds and 12 seconds respectively. The overall amplification time is about 12 minutes. Once this step is completed, the amplified target is then transferred from the amplification chamber and into the conduit that leads to the detection region of the device. In one embodiment, at the end of the PCR reaction gaskets sealing the PCR chip entry and exit ports are lifted off of both the entry and exit ports. An air bladder is depressed in the cartridge, creating a positive air pressure in the entry port gasket, forcing the liquid out of the exit port gasket, moving the liquid towards the final detection region of the chip. Here, a set of conductivity bars are used for monitoring the movement of liquid to the detection region.

In the preferred embodiment the clam-like primers are used, thus in the unheated conduit that leads to the detection region, these primers re-anneal to themselves and are effectively removed from the assay as interferents. In an alternative embodiment, where electrophoresis is used to separate out unwanted primer the elements described in FIG. 12 and FIG. 13 are combined into the single-use device as shown in FIG. 24. This separation process is described above. In the single-use device with electrophoretic separation, the instrument makes electrical connection to the electrophoresis electrodes 74, 75 and 76 (see FIG. 13), and 652, 653 and 654 (see FIG. 24). In the device the time for this step is typically less than 1 to 2 minutes, depending on the sizes of primer and amplicon. In another alternative embodiment where enzymatic removal of unused primer is employed, the enzymatic mixture is applied to a portion of the wall 150 of the conduit leading from the amplification chamber to the detection region. This material dissolves onto the liquid containing the amplicon and converts the primer to a non-interfering form as described above. The dry reagent mixture on the wall is preferably the enzyme in a support matrix comprising trehalose or ficoll, which promotes rapid dissolution. The time taken for the enzymatic step is typically about six minutes and is dependent on the amount of enzyme, temperature, type of primer being removed. In another embodiment, post-hybridization of the amplicons with a first capture oligonucleotide, which removes the detection region of the amplicons, followed by a wash step to remove any unbound unincorporated oligonucleotides which would be involved in the final capture step can be used. The amplicons and primers bound in the first capture step are then un-bound using heat or alkaline conditions, then allowed to move to the final detection region, where the capture oligonucleotides capture fully created amplicons.

In the next step the amplicon arrives in the detection region and the dissolution of the reagent on the wall of the detection chamber 151 occurs. In the preferred embodiment this reagent is streptavidin-labeled alkaline phosphatase which binds to the moiety on the amplicon which is preferably biotin to form a complex of amplicon and the enzyme. This complex can then bind to the capture oligonucleotide on the sensor. Depending on the kinetics the amplicon may also bind first to the capture oligonucleotide and then the labeled enzyme. In the device the time for this step is typically about 5 to 15 minutes.

In the final step detection reagent is displaced from the detection reagent chamber into the sensing region, thereby displacing any unbound amplicon and labeled enzyme to the waste chamber. Elements 152 and 153 which are constriction that cause turbulence in the region of the sensor may optionally be included to enhance the efficiency of the hybridization step, thus reducing the hybridization time and the amount of wash fluid that is required. In the device the time for this step is typically less than 70 seconds and the amount of wash fluid that is used is about 10 to 50 uL. As stated previously the wash fluid also contains a reagent that enables detection. A trailing portion of the fluid is retained over the sensor, thus enabling the captured alkaline phosphatase to convert the reagent p-aminophenol phosphate to p-aminophenol which is then oxidized at the electrode to give rise to a measurable current. In the device the time for this step is typically less than 1 minute. Positioning of the trailing edge with respect to the sensor may be achieved using a pair of electrodes 155 and 156 forming a conductivity sensor as described above.

The measured current is used by the instrument to determine the presence or absence of the suspected target nucleic acid in the original sample. This may be a qualitative result, or where the target is present, a quantitative determination of the amount of target in the sample. An algorithm for a particular target factors the original sample volume entering the extraction chamber, the number and efficiency of amplification cycles and the efficiency of the capture reaction along with any other necessary factors to determine the original concentration of the target in the sample. Such factors are independently determined using known samples from a reference method. These methods are well known in the art.

In a related embodiment, a second sensor 154 is provided in the detection region to account for any non-specific binding of the streptavidin-labeled alkaline phosphatase to the first sensor. The second sensor is the same as the first but, has a capture oligonucleotide that does not bind to the amplicon. Any signal at the second sensor is subtracted from the signal at the first by the algorithm.

The overall time for the assay, from sample entry into the single-use device and insertion into the instrument, takes between about 10 and 20 minutes and generally depends on the specific target and the required number of amplification cycles. When the genetic test is complete and result is displayed by the instrument, the actuation mechanism within the instrument then releases the device and it can be removed and discarded by the user. The instrument is then ready to receive a new single-use device. A significant advantage of the disclosed device and instrument combination is that once the sample has entered the device, all other steps are controlled by the instrument, thus eliminating possible human error in the test cycle. This means the system can be used reliably by those not specifically skilled in analytical laboratory measurement. For example a physician may use the system at the bedside or during a patient's office visit. The system may also be used at remote locations, for example in environmental monitoring and hazard assessment. An added benefit of the design is that it also retains sample residue and amplified material within the device for safer disposal.

In an alternative embodiment of housing 100, the extraction chamber 102 contains a filter material 157 and 421, impregnated with extraction reagents comprising a chelating agent and a chaotropic agent. One wall of the extraction chamber is also composed of heating element with a thermistor for controlling temperature. The filter material is preferably composed of 3MM Whatman paper and has a carboxylated surface which preferentially binds nucleic acid. When the sample, e.g. blood, enters the extraction chamber, it dissolves the extraction reagent and nucleic acid from the cellular material binds to the filter. This step of the extraction process takes about 0.5 to 2 minutes. A bolus of wash fluid from the wash fluid chamber 122 is then pushed through the extraction chamber and exits into the wash fluid waste chamber 123, carrying away lysed cellular debris from the sample, while leaving the extracted nucleic acid adsorbed onto the filter. Multiple boluses of wash fluid may be used to ensure a complete wash. A further bolus of wash fluid is then pushed into the chamber and the instrument activates the heating element and controls the temperature of the bolus of fluid to 90° C., by means of the thermistor. This caused the nucleic acid absorbed onto the filter to desorb from the filter and dissolve in the fluid. The fluid containing the nucleic acid material is then pneumatically transferred to the amplification chamber. In this embodiment the wash fluid is preferably deionized water.

```
<200> SEQUENCE CHARACTERISTICS:
<210> SEQ ID NO: 1
<211> LENGTH: 31
<212> TYPE: DNA
<213> ORGANISM: Artificial
<220> FEATURE:
   <221> NAME/KEY: Misc_feature
   <222> LOCATION: 1-31
   <223> OTHER INFORMATION: sequence is
         synthesized
   <400> SEQUENCE: 1
ACTTCATACA CAACTCCCGC GTTGCATAAC T                  50
<200> SEQUENCE CHARACTERISTICS:
<210> SEQ ID NO: 2
<211> LENGTH: 20
<212> TYPE: DNA
<213> ORGANISM: Artificial
<220> FEATURE:
   <221> NAME/KEY: Misc_feature
   <222> LOCATION: 1-20
   <223> OTHER INFORMATION: sequence is
         synthesized
   <400> SEQUENCE: 2
TGGCAAGGG TAAACAGATC                                50
<200> SEQUENCE CHARACTERISTICS:
<210> SEQ ID NO: 3
<211> LENGTH: 22
<212> TYPE: DNA
<213> ORGANISM: Artificial
<220> FEATURE:
   <221> NAME/KEY: Misc_feature
   <222> LOCATION: 1-22
   <223> OTHER INFORMATION: sequence is
         synthesized
   <400> SEQUENCE: 3
AACAATACCA CCGTAGCGAT CA                            50
<200> SEQUENCE CHARACTERISTICS:
<210> SEQ ID NO: 4
<211> LENGTH: 22
<212> TYPE: DNA
<213> ORGANISM: Artificial
<220> FEATURE:
   <221> NAME/KEY: Misc_feature
   <222> LOCATION: 1-22
   <223> OTHER INFORMATION: sequence is
         synthesized
   <400> SEQUENCE: 4
AACAATACCACCGTAGCGATCA                              50
<200> SEQUENCE CHARACTERISTICS:
<210> SEQ ID NO: 5
<211> LENGTH: 59
<212> TYPE: DNA
<213> ORGANISM: Artificial
<220> FEATURE:
   <221> NAME/KEY: Misc_feature
   <222> LOCATION: 1-59
   <223> OTHER INFORMATION: sequence is
         synthesized
   <400> SEQUENCE: 5
ACTTCATACA CAACTCCCGC GTTGCATAAC TAAAAACTGG          50
CAAGGGTAAA CAGATCCCC                                100
<200> SEQUENCE CHARACTERISTICS:
<210> SEQ ID NO: 6
<211> LENGTH: 75
<212> TYPE: DNA
<213> ORGANISM: Artificial
<220> FEATURE:
   <221> NAME/KEY: Misc_feature
   <222> LOCATION: 1-75
   <223> OTHER INFORMATION: sequence is
         synthesized
   <400> SEQUENCE: 6
TTGCCAGACT TCATACACAA CTCCCGCGTT GCATAACTAA          50
```

```
-continued
AAAGTATGAA GTCTGGCAAG GGTAAACAGA TCCCC              100
<200> SEQUENCE CHARACTERISTICS:
<210> SEQ ID NO: 7
<211> LENGTH: 79
<212> TYPE: DNA
<213> ORGANISM: Artificial
<220> FEATURE:
   <221> NAME/KEY: Misc_feature
   <222> LOCATION: 1-79
   <223> OTHER INFORMATION: sequence is
         synthesized
   <400> SEQUENCE: 7
ACCCTTGCCA GACTTCATAC ACAACTCCCG CGTTGCATAA          50
CTAAAAAGTA TGAAGTCTGG CAAGGGTAAA CAGATCCCC           100
<200> SEQUENCE CHARACTERISTICS:
<210> SEQ ID NO: 8
<211> LENGTH: 38
<212> TYPE: DNA
<213> ORGANISM: Artificial
<220> FEATURE:
   <221> NAME/KEY: Misc_feature
   <222> LOCATION: 1-38
   <223> OTHER INFORMATION: sequence is
         synthesized
   <400> SEQUENCE: 8
TTGCCAGACTTCATACACAACTCCCGCGTTGCATAACT              50
<200> SEQUENCE CHARACTERISTICS:
<210> SEQ ID NO: 9
<211> LENGTH: 33
<212> TYPE: DNA
<213> ORGANISM: Artificial
<220> FEATURE:
   <221> NAME/KEY: Misc_feature
   <222> LOCATION: 1-33
   <223> OTHER INFORMATION: sequence is
         synthesized
   <400> SEQUENCE: 9
GTATGAAGTCTGGCAAGGGTAAACAGATCCCC                    50
<200> SEQUENCE CHARACTERISTICS:
<210> SEQ ID NO: 10
<211> LENGTH: 35
<212> TYPE: DNA
<213> ORGANISM: Artificial
<220> FEATURE:
   <221> NAME/KEY: Misc_feature
   <222> LOCATION: 1-35
   <223> OTHER INFORMATION: sequence is
         synthesized
   <400> SEQUENCE: 10
ACCCTTGCCAGACTTCATACCCGCGTTGCATAACT                 50
<200> SEQUENCE CHARACTERISTICS:
<210> SEQ ID NO: 11
<211> LENGTH: 32
<212> TYPE: DNA
<213> ORGANISM: Artificial
<220> FEATURE:
   <221> NAME/KEY: Misc_feature
   <222> LOCATION: 1-32
   <223> OTHER INFORMATION: sequence is
         synthesized
   <400> SEQUENCE: 11
GTATGAAGTCTGGCAAGGGTAAACAGATCCCC                    50
```

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

SEQUENCE LISTING

<160> NUMBER OF SEQ ID NOS: 15

<210> SEQ ID NO 1
<211> LENGTH: 31
<212> TYPE: DNA
<213> ORGANISM: Artificial Sequence
<220> FEATURE:
<223> OTHER INFORMATION: Synthetic sequence

<400> SEQUENCE: 1
acttcataca caactcccgc gttgcataac t                                31

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
tggcaagggt aaacagatc                                              19

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence

<400> SEQUENCE: 3
aacaatacca ccgtagcgat ca                                          22

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence

<400> SEQUENCE: 4
aacaatacca ccgtagcgat ca                                          22

<210> SEQ ID NO 5
<211> LENGTH: 59
<212> TYPE: DNA
<213> ORGANISM: Artificial Sequence
<220> FEATURE:
<223> OTHER INFORMATION: Synthetic sequence

<400> SEQUENCE: 5
acttcataca caactcccgc gttgcataac taaaaactgg caagggtaaa cagatcccc   59

<210> SEQ ID NO 6
<211> LENGTH: 75
<212> TYPE: DNA
<213> ORGANISM: Artificial Sequence
<220> FEATURE:
<223> OTHER INFORMATION: Synthetic sequence

<400> SEQUENCE: 6
ttgccagact tcatacacaa ctcccgcgtt gcataactaa aaagtatgaa gtctggcaag   60
ggtaaacaga tcccc                                                  75

<210> SEQ ID NO 7
<211> LENGTH: 79

<212> TYPE: DNA
<213> ORGANISM: Artificial Sequence
<220> FEATURE:
<223> OTHER INFORMATION: Synthetic sequence

<400> SEQUENCE: 7
acccttgcca gacttcatac acaactcccg cgttgcataa ctaaaaagta tgaagtctgg    60
caagggtaaa cagatcccc                                                 79

<210> SEQ ID NO 8
<211> LENGTH: 38
<212> TYPE: DNA
<213> ORGANISM: Artificial Sequence
<220> FEATURE:
<223> OTHER INFORMATION: Synthetic sequence

<400> SEQUENCE: 8
ttgccagact tcatacacaa ctcccgcgtt gcataact                             38

<210> SEQ ID NO 9
<211> LENGTH: 32
<212> TYPE: DNA
<213> ORGANISM: Artificial Sequence
<220> FEATURE:
<223> OTHER INFORMATION: Synthetic sequence

<400> SEQUENCE: 9
gtatgaagtc tggcaagggt aaacagatcc cc                                  32

<210> SEQ ID NO 10
<211> LENGTH: 35
<212> TYPE: DNA
<213> ORGANISM: Artificial Sequence
<220> FEATURE:
<223> OTHER INFORMATION: Synthetic sequence

<400> SEQUENCE: 10
acccttgcca gacttcatac ccgcgttgca taact                               35

<210> SEQ ID NO 11
<211> LENGTH: 32
<212> TYPE: DNA
<213> ORGANISM: Artificial Sequence
<220> FEATURE:
<223> OTHER INFORMATION: Synthetic sequence

<400> SEQUENCE: 11
gtatgaagtc tggcaagggt aaacagatcc cc                                  32

<210> SEQ ID NO 12
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(32)
<223> OTHER INFORMATION: location of HPEG spacer sequence

<400> SEQUENCE: 12
acttcataca caactcccgc gttgcataac ttggcaaggg taaacagatc c              51

<210> SEQ ID NO 13
<211> LENGTH: 44
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 56-FAM fluorescent species on 5' end
<220> FEATURE:
<221> NAME/KEY: misc_feature
<222> LOCATION: (22)..(23)
<223> OTHER INFORMATION: location of HPEG spacer sequence

<400> SEQUENCE: 13
aacaatacca ccgtagcgat caaacaatac caccgtagcg atca              44

<210> SEQ ID NO 14
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (38)..(39)
<223> OTHER INFORMATION: location of HPEG spacer sequence

<400> SEQUENCE: 14
ttgccagact tcatacacaa ctcccgcgtt gcataactgt atgaagtctg gcaagggtaa    60
acagatcccc                                                           70

<210> SEQ ID NO 15
<211> LENGTH: 67
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (35)..(36)
<223> OTHER INFORMATION: location of HPEG spacer sequence

<400> SEQUENCE: 15
acccttgcca gacttcatac ccgcgttgca taactgtatg aagtctggca agggtaaaca    60
gatcccc                                                              67
```

What is claimed is:

1. An integrated single-use device for performing a nucleic acid analysis, comprising:
   a housing,
   an entry port for accepting a sample suspected of containing a target nucleic acid,
   a first chamber operably connected to the entry port and comprising:
      a reagent for extracting the target nucleic acid,
      magnet beads comprising a coating configured to bind the target nucleic acid, and
      a wax configured to melt and form a contiguous wax layer in a region of egress of the first chamber;
   a means for generating a magnetic field configured to draw the magnet beads through the contiguous wax layer;
   a first conduit permitting passage of extracted nucleic acid from the region of egress of the first chamber into an amplification chamber, said housing containing an amplification reagent that is capable of incorporating a detectable label into an amplified nucleic acid target, the amplification chamber having a heating means and a temperature sensing means for controlling amplification conditions,
   the amplification chamber being operably linked to a second conduit containing a sensing region with an immobilized capture oligonucleotide,
   a means for moving the amplified target to the sensing region to permit binding of said amplified target to said capture oligonucleotide, and
   a holding chamber operably attached to said second conduit and containing a fluid configured to substantially displace uncaptured amplified target from the sensing region and permit sensing of said detectable label retained in said sensing region.

2. The device of claim 1, wherein the label moiety is selected from the group consisting of fluorocein, dinitrophenol, biotin, cholesterol, digoxigenin and estrialdiol.

3. The device of claim 1, wherein the sensing region is interrogated by an optical detector.

4. The device of claim 1, wherein the sensing region is interrogated by an integrated optical detector.

5. The device of claim 1, wherein the sensing region is interrogated by an integrated electrochemical detector.

6. The device of claim 1, wherein amplification reagent is located in said first conduit.

7. The device of claim 1, wherein amplification reagent is located in said amplification chamber.

8. The device of claim 1, wherein amplification reagent is located in a holding chamber operably connected to said amplification chamber.

9. The device of claim 1, wherein amplification reagent is located in a holding chamber operably connected to said first conduit.

10. The device of claim 1, wherein said fluid is a wash fluid and contained in a sealed pouch within the holding chamber.

11. The device of claim 1, wherein said means for moving the amplification target is pneumatic.

12. An integrated single-use device for performing a nucleic acid analysis, comprising:
- a housing,
- an entry port for accepting a sample suspected of containing a target nucleic acid,
- a first chamber operably connected to the entry port and comprising:
  - a reagent for extracting the target nucleic acid onto magnetic beads that are located in the first chamber, and
  - a wax configured to melt and form a substantially contiguous wax layer that covers an egress region of the first chamber into a first conduit,
  - wherein the magnetic beads that are associated with the extracted target nucleic acid are configured to pass through the wax layer into the first conduit by means of an applied magnetic field,
- the first conduit permitting passage of the extracted target nucleic acid and the magnetic beads into an amplification chamber, said housing containing an amplification reagent that is capable of incorporating a detectable label into an amplified nucleic acid target,
- the amplification chamber having a heating means and a temperature sensing means for controlling amplification conditions,
- the amplification chamber being operably linked to a second conduit containing a sensing region with an immobilized capture oligonucleotide,
- said housing containing a means for moving the amplified target to the sensing region to permit binding of said amplified target to said capture oligonucleotide, and
- a holding chamber operably attached to said second conduit and containing a fluid configured to substantially displace uncaptured amplified target from the sensing region and permit optical sensing of the detectable label retained in the sensing region.

13. The device of claim 12, wherein the detectable label is selected from the group consisting of fluorocein, dinitrophenol, biotin, cholesterol, digoxigenin and estrialdiol.

14. The device of claim 12, wherein the sensing region is interrogated by an optical detector.

15. The device of claim 12; wherein the sensing region is interrogated by an integrated optical detector.

16. The device of claim 12, wherein amplification reagent is located in said first conduit.

17. The device of claim 12, wherein amplification reagent is located in said amplification chamber.

18. The device of claim 12, wherein amplification reagent is located in a holding chamber operably connected to said amplification chamber.

19. The device of claim 12, wherein amplification reagent is located in a holding chamber operably connected to said first conduit.

20. The device of claim 12, wherein said fluid is a wash fluid and contained in a sealed pouch within the holding chamber.

21. The device of claim 12, wherein said means for moving the amplification target is pneumatic.

* * * * *